United States Patent
Canan et al.

(10) Patent No.: US 10,420,771 B2
(45) Date of Patent: Sep. 24, 2019

(54) ANIMAL AND HUMAN ANTI-MALARIAL AGENTS

(71) Applicant: Celgene Corporation, Summit, NJ (US)

(72) Inventors: Stacie S. Canan, La Jolla, CA (US); Natalie Anne Hawryluk, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/000,968

(22) Filed: Jun. 6, 2018

(65) Prior Publication Data

US 2018/0280398 A1 Oct. 4, 2018

Related U.S. Application Data

(62) Division of application No. 15/611,108, filed on Jun. 1, 2017, now Pat. No. 10,016,436.

(60) Provisional application No. 62/344,756, filed on Jun. 2, 2016.

(51) Int. Cl.
| | | |
|---|---|---|
| *A61K 31/52* | (2006.01) | |
| *G01N 33/569* | (2006.01) | |
| *C07D 231/02* | (2006.01) | |
| *C07C 211/36* | (2006.01) | |
| *C07C 13/06* | (2006.01) | |
| *C07C 217/02* | (2006.01) | |
| *C07D 473/32* | (2006.01) | |

(52) U.S. Cl.
CPC ............ *A61K 31/52* (2013.01); *C07C 211/36* (2013.01); *C07D 473/32* (2013.01); *C07C 13/06* (2013.01); *C07C 217/02* (2013.01); *C07D 231/02* (2013.01); *G01N 33/56905* (2013.01); *Y02A 50/411* (2018.01)

(58) Field of Classification Search
CPC ....... A61K 31/52; C07C 13/06; C07C 211/36; C07C 217/02; C07D 231/02; C07D 473/32; G01N 33/56905; Y02A 50/411
See application file for complete search history.

(56) References Cited

U.S. PATENT DOCUMENTS

| | | |
|---|---|---|
| 7,521,446 B2 | 4/2009 | Albers et al. |
| 7,723,340 B2 | 5/2010 | Albers et al. |
| 7,759,342 B2 | 7/2010 | Bennett et al. |
| 8,101,588 B2 | 1/2012 | Albers et al. |
| 8,158,635 B2 | 4/2012 | Beauchamps et al. |
| 9,725,450 B2 | 8/2017 | Clareen et al. |
| 2010/0056494 A1 | 3/2010 | Winzeler et al. |

FOREIGN PATENT DOCUMENTS

| | | | | |
|---|---|---|---|---|
| WO | WO 2006/076595 | * | 7/2006 | ........... C07D 473/00 |
| WO | WO 2007/135380 | | 11/2007 | |
| WO | WO 2010/059418 | | 5/2010 | |

OTHER PUBLICATIONS

Wilen et al., (1977) "Strategies in optical resolutions," *Tetrahedron*, 33.21 (1977): 2725-2736.

* cited by examiner

*Primary Examiner* — Erich A Leeser
(74) *Attorney, Agent, or Firm* — Jones Day

(57) ABSTRACT

Provided herein are Purine Compounds of Formula (I)

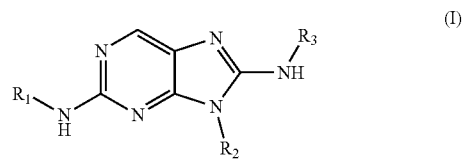

(I)

or pharmaceutically acceptable salts, tautomers, isotopologs, or stereoisomers thereof, wherein $R^1$, $R^2$, and $R^3$ are as defined herein, compositions comprising an effective amount of a Purine Compound, and methods for treating or preventing malaria comprising the administration of an effective amount of a Purine Compound.

22 Claims, No Drawings

ANIMAL AND HUMAN ANTI-MALARIAL AGENTS

This application is a divisional of U.S. patent application Ser. No. 15/611,108, filed Jun. 1, 2017, currently allowed, which claims the benefit of U.S. Provisional Application No. 62/344,756, filed Jun. 2, 2016, the entire contents of which is incorporated herein by reference.

FIELD

Provided herein are certain purine compounds, compositions comprising an effective amount of such compounds, and methods for treating or preventing malaria, comprising administering an effective amount of such purine compounds to a subject in need thereof, as well as the inventive compounds and compositions for use in such methods.

BACKGROUND

Malaria is caused by protozoan parasites of the genus *Plasmodium* (*falciparum, vivax, ovale, malariae* and *knowlesi*) that infect and destroy red blood cells, leading to fever, severe anemia, cerebral malaria and, if untreated, death. *Plasmodium falciparum* is the dominant species in sub-Saharan Africa, and is responsible for the almost 1 million deaths each year. The disease burden is heaviest in African children under 5 years of age and in pregnant women. *Plasmodium vivax* causes 25-40% of the global malaria burden, particularly in South and Southeast Asia, and Central and South America. The other two main species that are known to infect humans are *Plasmodium ovale* and *Plasmodium malariae*. A fifth species *Plasmodium knowlesi*, a species that infects primates, has led to human malaria, but the exact mode of transmission remains unclear.

Malaria is a disease that is prevalent in many developing countries. Approximately 40% of the world's population lives in countries where the disease is endemic; approximately 247 million people suffer from the disease every year.

Various medications are presently used for the treatment of malaria. However, many of these medications are costly and some exhibit significant toxicity and undesirable side effects in humans. The most common drug for treating malaria is chloroquine. Other drugs include quinine, mefloquine, atovaquone, proguanil, doxycycline, artesunate, hydroxychloroquine, halofantrine, pyrimethamine-sulfadoxine, and primaquine.

However, the widespread emergence of drug resistance of malaria parasites in many tropical countries has compromised many of the current chemotherapies and there is a continued need for new chemotherapeutic approaches. Accordingly, provide herein are novel potent anti-malarial agents and methodology of treating malaria using novel potent anti-malarial agents.

Citation or identification of any reference in this application is not to be construed as an admission that the reference is prior art to the present application.

SUMMARY

Provided herein are methods for treating or preventing malaria, comprising administering to a subject in need thereof an effective amount of a Purine Compound of Formula (I)

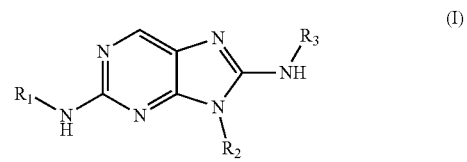

wherein $R^1$, $R^2$, and $R^3$ are as defined herein.

In one aspect, provided herein is a Purine Compound for use as a medicament. In one embodiment provided herein are methods for treating malaria by administering a compound of Formula (I).

A Purine Compound of Formula (I) is useful for treating or preventing malaria. In one aspect, provided herein is a compound of Formula (I) for use in treating malaria.

In one aspect, provided herein are Purine Compounds of Formula (I), as described in the instant disclosure, such as, for example, in Table 1.

In another aspect, provided herein are pharmaceutical compositions comprising an effective amount of a Purine Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing malaria, comprising administering to a subject in need thereof an effective amount of a Purine Compound as described herein, and a pharmaceutically acceptable carrier, excipient or vehicle. In one aspect, provided herein is a Purine Compound for use in a method or treating malaria, the method comprising administering to a subject in need thereof an effective amount of the Purine Compound.

In a further embodiment provided herein are compounds and compositions for use in a method as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1] pentyl, bicyclo[2.1.1]hexyl, bicyclo[2.2.1]heptyl, bicyclo [2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or 6 to 10 carbon atoms, or even 6 to 8 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d] oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo [d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g., 1H-benzo[d][1, 2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4, 5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with at least one hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —$NH_2$.

A "hydroxyl amine" group is a radical of the formula: —N($R^\#$)OH or —NHOH, wherein $R^\#$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N($R^\#$)O-alkyl or —NHO-alkyl, wherein $R^\#$ is as defined above.

An "aryloxyamine" group is a radical of the formula: —N($R^\#$)O-aryl or —NHO-aryl, wherein $R^\#$ is as defined above.

An "aralkoxyamine" group is a radical of the formula: —N($R^\#$)O-aralkyl or —NHO-aralkyl, wherein $R^\#$ is as defined above.

An "alkylamine" group is a radical of the formula: —NH-alkyl or —N(alkyl)$_2$, wherein each alkyl is independently as defined above.

An "aminocarbonyl" group is a radical of the formula: —C(=O)N($R^\#$)$_2$, —C(=O)NH($R^\#$) or —C(=O)$NH_2$, wherein each $R^\#$ is as defined above.

An "acylamino" group is a radical of the formula: —NHC(=O)($R^\#$) or —N(alkyl)C(=O)($R^\#$), wherein each alkyl and $R^\#$ are independently as defined above.

An "O(alkyl)aminocarbonyl" group is a radical of the formula: —O(alkyl)C(=O)N($R^\#$)$_2$, —O(alkyl)C(=O)NH($R^\#$) or —O(alkyl)C(=O)$NH_2$, wherein each $R^\#$ is independently as defined above.

An "N-oxide" group is a radical of the formula: —$N^+$—$O^-$.

A "carboxy" group is a radical of the formula: —C(=O)OH.

A "ketone" group is a radical of the formula: —C(=O)($R^\#$), wherein $R^\#$ is as defined above.

An "aldehyde" group is a radical of the formula: —CH(=O).

An "ester" group is a radical of the formula: —C(=O)O($R^\#$) or —OC(=O)($R^\#$), wherein $R^\#$ is as defined above.

A "urea" group is a radical of the formula: —N(alkyl)C(=O)N($R^\#$)$_2$, —N(alkyl)C(=O)NH($R^\#$), —N(alkyl)C(=O)$NH_2$, —NHC(=O)N($R^\#$)$_2$, —NHC(=O)NH($R^\#$), or —NHC(=O)$NH_2$#, wherein each alkyl and $R^\#$ are independently as defined above.

An "imine" group is a radical of the formula: —N=C($R^\#$)$_2$ or —C($R^\#$)=N($R^\#$), wherein each $R^\#$ is independently as defined above.

An "imide" group is a radical of the formula: —C(=O)N($R^\#$)C(=O)($R^\#$) or —N((C=O)($R^\#$))$_2$, wherein each $R^\#$ is independently as defined above.

A "urethane" group is a radical of the formula: —OC(=O)N($R^\#$)$_2$, —OC(=O)NH($R^\#$), —N($R^\#$)C(=O)O($R^\#$), or —NHC(=O)O($R^\#$), wherein each $R^\#$ is independently as defined above.

An "amidine" group is a radical of the formula: —C(=N($R^\#$))N($R^\#$)$_2$, —C(=N($R^\#$))NH($R^\#$), —C(=N($R^\#$))$NH_2$, —C(=NH)N($R^\#$)$_2$, —C(=NH)NH($R^\#$), —C(=NH)$NH_2$, —N=C($R^\#$)N($R^\#$)$_2$, —N=C($R^\#$)NH($R^\#$), —N=C($R^\#$)$NH_2$, —N($R^\#$)C($R^\#$)=N($R^\#$), —NHC($R^\#$)=N($R^\#$), —N($R^\#$)C($R^\#$)=NH, or —NHC($R^\#$)=NH, wherein each $R^\#$ is independently as defined above.

A "guanidine" group is a radical of the formula: —N($R^\#$)C(=N($R^\#$))N($R^\#$)$_2$, —NHC(=N($R^\#$))N($R^\#$)$_2$, —N($R^\#$)C(=NH)N($R^\#$)$_2$, —N($R^\#$)C(=N($R^\#$))NH($R^\#$), —N($R^\#$)C(=N($R^\#$))$NH_2$, —NHC(=NH)N($R^\#$)$_2$, —NHC(=N($R^\#$))NH($R^\#$), —NHC(=N($R^\#$))$NH_2$, —NHC(=NH)NH($R^\#$), —NHC(=NH)$NH_2$, —N=C(N($R^\#$)$_2$)$_2$, —N=C(NH($R^\#$))$_2$, or —N=C($NH_2$)$_2$, wherein each $R^\#$ is independently as defined above.

An "enamine" group is a radical of the formula: —N($R^\#$)C($R^\#$)=C($R^\#$)$_2$, —NHC($R^\#$)=C($R^\#$)$_2$, —C(N($R^\#$)$_2$)=C($R^\#$)$_2$, —C(NH($R^\#$))=C($R^\#$)$_2$, —C($NH_2$)=C($R^\#$)$_2$, —C(R#)=C(R#)(N(R#)$_2$), —C(R#)=C(R#)(NH(R#)) or —C(R#)=C(R#)(NH$_2$), wherein each R# is independently as defined above.

An "oxime" group is a radical of the formula: —C(=NO(R#))(R#), —C(=NOH)(R#), —CH(=NO(R#)), or —CH(=NOH), wherein each R# is independently as defined above.

A "hydrazide" group is a radical of the formula: —C(=O)N(R#)N(R#)$_2$, —C(=O)NHN(R#)$_2$, —C(=O)N(R#)NH(R#), —C(=O)N(R#)NH$_2$, —C(=O)NHNH(R#)$_2$, or —C(=O)NHNH$_2$, wherein each R# is independently as defined above.

A "hydrazine" group is a radical of the formula: —N(R#)N(R#)$_2$, —NHN(R#)$_2$, —N(R#)NH(R#), —N(R#)NH$_2$, —NHNH(R#)$_2$, or —NHNH$_2$, wherein each R# is independently as defined above.

A "hydrazone" group is a radical of the formula: —C(=N—N(R#)$_2$)(R#)$_2$, —C(=N—NH(R#)(R#)$_2$, —C(=N—NH$_2$)(R#)$_2$, —N(R#)(N=C(R#)$_2$), or —NH(N=C(R#)$_2$), wherein each R# is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula: —S(R#), wherein R# is as defined above.

A "thiocarbonyl" group is a radical of the formula: —C(=S)(R#), wherein R# is as defined above.

A "sulfinyl" group is a radical of the formula: —S(=O)(R#), wherein R# is as defined above.

A "sulfone" group is a radical of the formula: —S(=O)$_2$(R#), wherein R# is as defined above.

A "sulfonylamino" group is a radical of the formula: —NHSO$_2$(R#) or —N(alkyl)SO$_2$(R#), wherein each alkyl and R# are defined above.

A "sulfonamide" group is a radical of the formula: —S(=O)$_2$N(R#)$_2$, or —S(=O)$_2$NH(R#), or —S(=O)$_2$NH$_2$, wherein each R# is independently as defined above.

A "phosphonate" group is a radical of the formula: —P(=O)(O(R#))$_2$, —P(=O)(OH)$_2$, —OP(=O)(O(R#))(R#), or —OP(=O)(OH)(R#), wherein each R# is independently as defined above.

A "phosphine" group is a radical of the formula: —P(R#)$_2$, wherein each R# is independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "Purine Compound" refers to compounds of Formula (I) as well as to further embodiments of compounds of formula (I) provided herein. In one embodiment, an "Purine Compound" is a compound set forth in Table 1. The term "Purine Compound" includes pharmaceutically acceptable salts, tautomers, isotopologues, and stereoisomers of the Purine Compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of Formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a Purine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Purine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Purine Compounds, as well as the use of mixtures of those forms, are encompassed by the embodiments disclosed herein. For example, mixtures comprising equal or unequal amounts of the enantiomers of a particular Purine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Purine Compounds can include E and Z isomers, or a mixture thereof, and cis and trans isomers or a mixture thereof. In certain embodiments, the Purine Compounds are isolated as either the E or Z isomer. In other embodiments, the Purine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

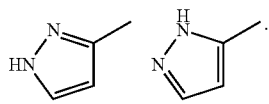

As readily understood by one skilled in the art, a wide variety of functional groups and other structures may exhibit tautomerism and all tautomers of compounds of Formula (I) are within the scope of the present invention.

It should also be noted the Purine Compounds can contain unnatural proportions of atomic isotopes at least one of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Purine Compounds as described herein, whether radioactive or not, are intended to be encompassed within the scope of the embodiments provided herein. In some embodiments, there are provided isotopologues of the Purine Compounds, for example, the isotopologues are deuterium, carbon-13, or nitrogen-15 enriched Purine Compounds.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is malaria.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is malaria, as described herein, or symptoms thereof. In one embodiment, preventing includes prophylaxis.

The term "effective amount" in connection with a Purine Compound means an amount capable of treating or preventing a disorder, disease or condition, or symptoms thereof, disclosed herein. In one embodiment, the disorder is malaria. The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial by malarial parasites, when administered before infection, i.e., before, during and/or after the exposure period to malarial parasites.

The term "prophylaxis" includes causal prophylaxis, i.e., antimalarial activity comprising preventing the pre-erythrocytic development of the parasite, suppressive prophylaxis, i.e., antimalarial activity comprising suppressing the development of the blood stage infection, and, for malaria, terminal prophylaxis, i.e., antimalarial activity comprising suppressing the development of intra-hepatic stage infection. This term includes primary prophylaxis (i.e., preventing initial infection) where the antimalarial compound is administered before, during and/or after the exposure period to malarial parasites and terminal prophylaxis (i.e., to prevent relapses or onset of clinical symptoms of malaria) when the antimalarial compound is administered towards the end of and/or after the exposure period to malarial parasites but before the clinical symptoms. Typically, against *P. falciparum* infections, suppressive prophylaxis is used whereas against *P. vivax* or a combination of *P. falciparum* and *P. vivax*, terminal prophylaxis is used.

Likewise, the term "treatment-effective amount" refers to a concentration of compound that is effective in treating malaria infection, e.g., leads to a reduction in parasite numbers in blood following microscopic examination when administered after infection has occurred.

"Combination" or administration "in combination" includes administration as a mixture, simultaneous administration using separate formulations, and consecutive administration in any order.

"Consecutive" means that more than 10 minutes have passed between the administration of the anti-MIF antibody and the administration of the chemotherapeutic agent. The time period can then be more than 10 minutes, more than 30 minutes, more than 1 hour, more than 3 hours, more than 6 hours or more than 12 hours.

The term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having malaria, or a symptom thereof. In another embodiment, a subject is a non-human mammal.

Purine Compounds

Provided herein are Purine Compounds having the following Formula (I):

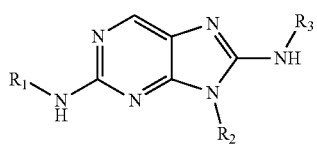

wherein:

$R^1$ is $CR^{1a}R^{1b}R^{1c}$, wherein $R^{1a}$ and $R^{1b}$ are $(C_{1-4})$alkyl and $R^{1c}$ is H or $(C_{1-4})$alkyl; or $R^{1a}$ and $R^{1b}$ form a 3-6 membered cycloalkyl or 3-6 membered heterocyclyl, and $R^{1c}$ is H or $(C_{1-4})$alkyl;

$R^2$ is $L-R^{2a}$ or $L-R^{2b}$,

L is a bond or $(C_{1-2}$ alkyl);

$R^{2a}$ is 3-6 membered N-containing heterocyclyl or heteroaryl, each optionally substituted with one or more $(C_{1-4})$alkyl, or $(C_{1-4})$alkyl-$NR_2$;

$R^{2b}$ is $(C_{1-4}$ branched or unbranched alkyl)-$NR_2$, $R^3$ is phenyl or pyridyl, substituted with at least one halogen, CN, $(C_{1-4})$alkyl, or $O(C_{1-4})$alkyl, wherein the alkyl is optionally fluorinated; and R is H or $(C_{1-4})$ alkyl;

provided the compound is not 4-(2-(isopropylamino)-8-((2,4,6-trifluorophenyl)amino)-9H-purin-9-yl)pyrrolidin-2-one

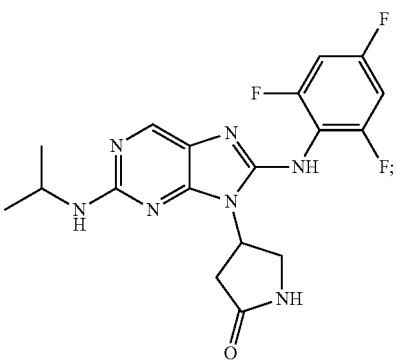 [SMILES: CC(C)Nc1ncc2nc(Nc3c(F)cc(F)cc3F)n(C3CNC(=O)C3)c2n1]

N²-cyclopentyl-N⁸-(2-fluorophenyl)-9-(piperidin-4-yl)-9H-purine-2,8-diamine

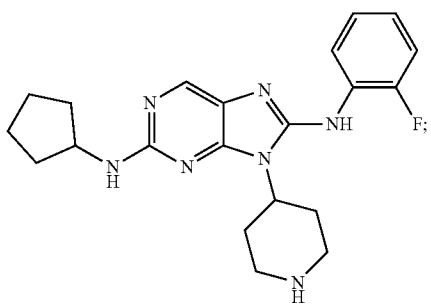 [SMILES: Fc1ccccc1Nc1nc2cnc(NC3CCCC3)nc2n1C1CCNCC1]

or

N²-cyclohexyl-N⁸-(2-fluorophenyl)-9-(piperidin-4-ylmethyl)-9H-purine-2,8-diamine

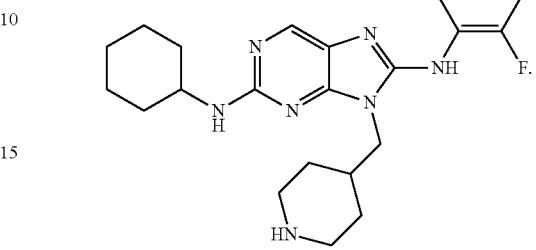

In some embodiments of compounds formula (I), $R^1$ is $CR^{1a}R^{1b}R^{1c}$, and $R^{1a}$ and $R^{1b}$ are $(C_{1-2})$alkyl and $R^{1c}$ is H or $(C_{1-4})$alkyl. For example, $R^1$ is isopropyl or t-butyl. In other embodiment, $R^1$ is isopropyl. In other embodiment, $R^1$ is t-butyl. In other embodiments, $R^1$ is $CR^{1a}R^{1b}R^{1c}$, and $R^{1a}$ and $R^{1b}$ form a 3-6 membered cycloalkyl or 3-6 membered heterocyclyl, and $R^{1c}$ is H or $(C_{1-2})$alkyl. In some embodiments, $R^{1a}$ and $R^{1b}$ form a cyclopropyl, cyclobutyl, cyclopentyl or tetrahydropyranyl. In some such embodiments, $R^{1c}$ is H or $CH_3$. In some embodiments of formula (I), $R^1$ is cyclopropyl, cyclobutyl, cyclopentyl, tetrahydropyranyl, 1-methyl-cyclopropyl, 1-methyl-cyclobutyl, 1-methyl-cylopentyl, 1-methyl-tetrahydropyranyl or 4-methyl-tetrahydropyranyl. In one embodiment, $R^1$ is cyclopropyl. In one embodiment, $R^1$ is cyclobutyl. In one embodiment, $R^1$ is cyclopentyl. In one embodiment, $R^1$ is tetrahydropyranyl. In one embodiment, $R^1$ is 1-methyl-cyclopropyl. In one embodiment, $R^1$ is 1-methyl-cyclobutyl. In one embodiment, $R^1$ is 1-methyl-cyclopentyl. In a specific embodiment, $R^1$ is 1-methyl-tetrahydropyranyl. In a specific embodiment, $R^1$ is 4-methyl-tetrahydropyranyl. In a more specific embodiment, $R^1$ is 4-methyl-tetrahydropyran-4-yl.

In some embodiments of compounds formula (I), $R^2$ is $L-R^{2a}$ and $R^{2a}$ is selected from azetidyl, pyrolidinyl, piperidyl, piperazinyl, imidazolyl, octahydrocyclopenta[c]pyrrolyl, or octahydro-1H-isoindolyl. In some embodiments of compounds formula (I), $R^2$ is $L-R^{2a}$ and $R^{2a}$ is selected from unsubstituted azetidyl, pyrolidinyl, piperidyl, piperazinyl, imidazolyl, octahydrocyclopenta[c]pyrrolyl, or octahydro-1H-isoindolyl. In some such embodiments, L is a bond, —$CH_2$— or —$CH_2CH_2$—. In others, $R^2$ is substituted with $CH_3$, $CH_2CH_3$, or $CH_2CH_2NH_2$. In still other embodiments, $R^2$ is azetidyl, piperidyl, pyrrolidyl, octahydrocyclopenta[c]pyrrolyl, octahydro-1H-isoindolyl, $CH_2$-pyrrolidyl, $CH_2CH_2$-pyrrolidyl, $CH_2$-piperidyl, $CH_2CH_2$-piperidyl, $CH_2CH_2$-imidazolyl, or $CH_2CH_2$-piperazinyl. In one embodiment, $R^2$ is azetidyl. In one embodiment, $R^2$ is piperidyl. In one embodiment, $R^2$ is pyrrolidyl. In one embodiment, $R^2$ is octahydrocyclopenta[c]pyrrolyl. In one embodiment, $R^2$ is octahydro-1H-isoindolyl. In one embodiment, $R^2$ is $CH_2$-pyrrolidyl. In one embodiment, $R^2$ is $CH_2CH_2$-pyrrolidyl. In one embodiment, $R^2$ is $CH_2CH_2$-piperidyl. In one embodiment, $R^2$ is $CH_2CH_2$-piperidyl. In one embodiment, $R^2$ is $CH_2CH_2$-imidazolyl. In one embodiment, $R^2$ is $CH_2CH_2$-piperazinyl.

In yet other embodiments, $R^2$ is $L-R^{2b}$ and $R^{2b}$ is $CH_2NR_2$, $CH_2CH_2NR_2$, $CH(CH_3)NR_2$, or $C(CH_3)_2NR_2$, In some such embodiments, L is a bond, —CH₂— or —CH₂CH₂—. For example, R² is CH₂CH₂NH₂, CH₂CH₂NH(CH₃), CH₂CH₂CH₂NH₂, CH₂CH₂CH₂N (CH₃)₂, CH₂CH(CH₃)NH₂, or CH₂C(CH₃)₂NH₂. In one embodiment, R² is CH₂CH₂NH₂. In one embodiment, R² is CH₂CH₂NH(CH₃), In one embodiment, R² is CH₂CH₂CH₂NH₂. In one embodiment, R² is CH₂CH₂CH₂N (CH₃)₂. In one embodiment, R² is CH₂CH(CH₃)NH₂. In one embodiment, R² is or CH₂C(CH₃)₂NH₂.

In some embodiments of compounds formula (I), R³ is phenyl substituted with at least one halogen, CN, fluorinated (C₁₋₂)alkyl, or O-fluorinated(C₁₋₂)alkyl. In some such embodiments, R³ is substituted with at least one F, Cl, CN, CHF₂, CF₃, or OCF₃.

In some embodiments, R³ is meta-substituted phenyl, for example, R³ is meta-Cl-phenyl, meta-CN-phenyl, meta-CF₃-phenyl, or meta-OCF₃-phenyl. In embodiment, R³ is meta-Cl-phenyl. In embodiment, R³ is meta-CN-phenyl, In embodiment, R³ is meta-CHF₂-phenyl. In embodiment, R³ is meta-CF₃-phenyl. In embodiment, R³ is meta-OCF₃-phenyl.

In still other embodiments, R³ is bis-meta-substituted phenyl, wherein each substituent is independently F, Cl, CN, or CF₃. In one embodiment, R³ is bis-meta-substituted phenyl, wherein each substituent is F. In one embodiment, R³ is bis-meta-substituted phenyl, wherein each substituent is Cl. In one embodiment, R³ is bis-meta-substituted phenyl, wherein each substituent is CF₃. In one embodiment, R³ is bis-meta-substituted phenyl, wherein one substituent is F and one substituent is Cl. In one embodiment, R³ is bis-meta-substituted phenyl, wherein one substituent is CF₃ and one substituent is Cl. In one embodiment, R³ is bis-meta-substituted phenyl, wherein one substituent is CN and one substituent is Cl.

In some embodiments, R³ is para-substituted phenyl, for example, para-OCF₃-phenyl, para-CF₃-phenyl, para-CN-phenyl, or para-Cl-phenyl. In one embodiment, R³ is para-Cl-phenyl. In one embodiment, R³ is para-OCF₃-phenyl. In one embodiment, R³ is para-CF₃-phenyl. In one embodiment, R³ is para-CN-phenyl. In one embodiment, R³ is para-OCF₃-phenyl. In some embodiments, R³ is meta-C₁, meta-CF₃-phenyl, meta-Cl, meta-OCF₃-phenyl, or meta-Cl, meta-F-phenyl. In some embodiments, R³ is meta-Cl, para-CF₃-phenyl, or para-Cl, meta-CF₃-phenyl. In one embodiment, R³ is ortho-F, meta-Cl-phenyl. In one embodiment R³ is meta-Cl, para-Cl-phenyl. In other embodiments, R³ is pyridyl, substituted with at least one halogen, fluorinated (C₁₋₂)alkyl, or O-fluorinated(C₁₋₂)alkyl. In some such embodiments, R³ is substituted with at least one Cl, or CF₃.

In some embodiments of compounds of formula (I), wherein R¹ is CR¹ᵃR¹ᵇR¹ᶜ, R¹ᵃ and R¹ᵇ form a 3-6 membered cycloalkyl or 3-6 membered heterocyclyl, and R¹ᶜ is H or (C₁₋₂)alkyl, R² is piperidyl, pyrrolidyl, CH₂-pyrrolidyl, CH₂CH₂-pyrrolidyl, CH₂-piperidyl, CH₂CH₂-piperidyl, CH₂CH₂-imidazolyl, or CH₂CH₂-piperazinyl. In some such embodiments, R² is substituted with CH₃, CH₂CH₃, or CH₂CH₂NH₂. In some such embodiments, R³ is phenyl substituted with at least one halogen, CN, fluorinated (C₁₋₂)alkyl, or O-fluorinated(C₁₋₂)alkyl. In some such embodiments, R³ is meta-substituted phenyl, or bis-meta-substituted phenyl. In some such embodiments, R¹ is cyclopropyl, cyclobutyl, cyclopentyl, tetrahydropyranyl, 1-methyl-cyclopropyl, 1-methyl-cylopentyl, or 1-methyl-tetrahydropyranyl. In some such embodiments, R³ is meta-substituted phenyl, or bis-meta-substituted phenyl. In others, R³ is meta-Cl-phenyl, meta-CN-phenyl, meta-CF₃-phenyl, or meta-OCF₃-phenyl, or R³ is bis-meta-substituted phenyl, wherein each substituent is independently CN, F, Cl, or CF₃.

Also provided herein are Purine Compounds having the following Formula (I):

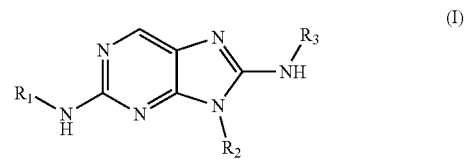

wherein:

R¹ is CR¹ᵃR¹ᵇR¹ᶜ, wherein R¹ᵃ and R¹ᵇ are (C₁₋₄)alkyl and R¹ᶜ is H or (C₁₋₄)alkyl; or R¹ᵃ and R¹ᵇ form a 3-6 membered cycloalkyl or 3-6 membered heterocyclyl, and R¹ᶜ is H or (C₁₋₄)alkyl;

R² is L-R²ᵃ or L-R²ᵇ,

L is a bond or (C₁₋₂ alkyl);

R²ᵃ is 3-6 membered N-containing heterocyclyl or heteroaryl, each optionally substituted with one or more (C₁₋₄)alkyl, or (C₁₋₄)alkyl-NR₂;

R²ᵇ is (C₁₋₂)alkyl-NR₂,

R³ is phenyl or pyridyl, substituted with at least one halogen, CN, (C₁₋₄)alkyl, or O(C₁₋₄)alkyl, wherein the alkyl is optionally fluorinated; and R is H or (C₁₋₄) alkyl;

provided the compound is not 4-(2-(isopropylamino)-8-((2,4,6-trifluorophenyl)amino)-9H-purin-9-yl)pyrrolidin-2-one

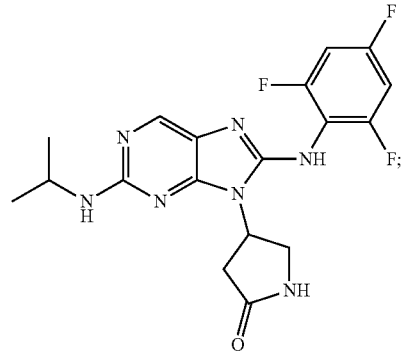 [SMILES: CC(C)Nc1ncc2nc(Nc3c(F)cc(F)cc3F)n(C3CNC(=O)C3)c2n1]

N²-cyclopentyl-N⁸-(2-fluorophenyl)-9-(piperidin-4-yl)-9H-purine-2,8-diamine

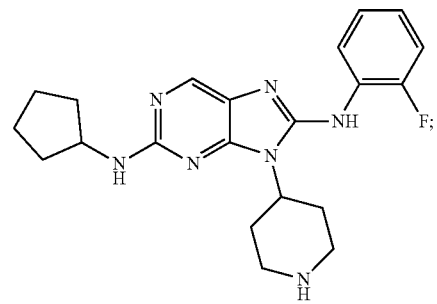 [SMILES: Fc1ccccc1Nc1nc2cnc(NC3CCCC3)nc2n1C1CCNCC1]

or

N²-cyclohexyl-N⁸-(2-fluorophenyl)-9-(piperidin-4-ylmethyl)-9H-purine-2,8-diamine.

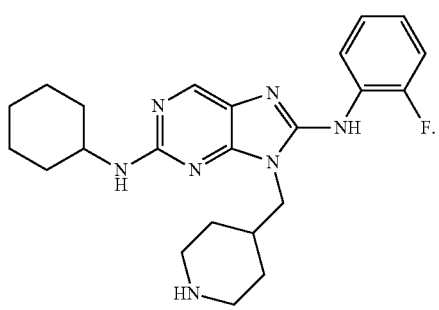 [SMILES: Fc1ccccc1Nc1nc2cnc(NC3CCCCC3)nc2n1CC1CCNCC1]

Also provided herein are Purine Compounds having the following Formula (I):

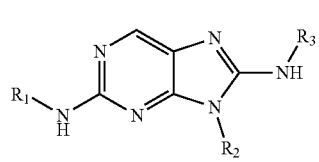

wherein:

$R^1$ is $CR^{1a}R^{1b}R^{1c}$, wherein $R^{1a}$ and $R^{1b}$ are $(C_{1-4})$alkyl and $R^{1c}$ is H or $(C_{1-4})$alkyl; or $R^{1a}$ and $R^{1b}$ form a 3-6 membered cycloalkyl or 3-6 membered heterocyclyl, and $R^{1c}$ is H or $(C_{1-4})$alkyl;

$R^2$ is L-$R^{2a}$ or L-$R^{2b}$,

L is a bond or $(C_{1-2}$ alkyl);

$R^{2a}$ is 3-6 membered N-containing heterocyclyl or heteroaryl, each substituted with at least one $(C_{1-4})$alkyl, or $(C_{1-4})$alkyl-$NR_2$;

$R^{2b}$ is $(C_{1-2})$alkyl-$NR_2$, $R^3$ is phenyl or pyridyl, substituted with at least one halogen, CN, $(C_{1-4})$alkyl, or $O(C_{1-4})$alkyl, wherein the alkyl is optionally fluorinated; and R is H or $(C_{1-4})$ alkyl;

provided the compound is not 4-(2-(isopropylamino)-8-((2,4,6-trifluorophenyl)amino)-9H-purin-9-yl)pyrrolidin-2-one

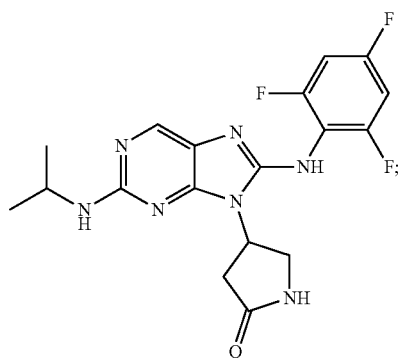 [SMILES: CC(C)Nc1ncc2nc(Nc3c(F)cc(F)cc3F)n(C3CNC(=O)C3)c2n1]

N²-cyclopentyl-N⁸-(2-fluorophenyl)-9-(piperidin-4-yl)-9H-purine-2,8-diamine

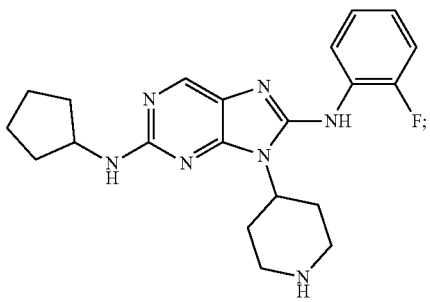 [SMILES: Fc1ccccc1Nc1nc2cnc(NC3CCCC3)nc2n1C1CCNCC1]

or
N²-cyclohexyl-N⁸-(2-fluorophenyl)-9-(piperidin-4-ylmethyl)-9H-purine-2,8-diamine.

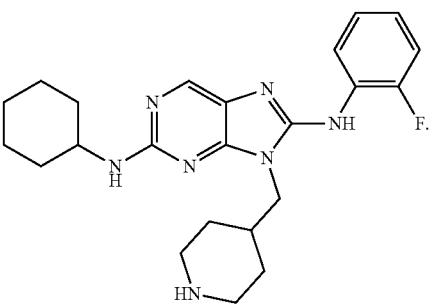 [SMILES: Fc1ccccc1Nc1nc2cnc(NC3CCCCC3)nc2n1CC1CCNCC1]

In some embodiments of compounds formula (I), $R^1$ is $CR^{1a}R^{1b}R^{1c}$, and $R^{1a}$ and $R^{1b}$ are $(C_{1-2})$alkyl and $R^{1c}$ is H or $(C_{1-4})$alkyl. For example, $R^1$ is isopropyl or t-butyl. In other embodiment, $R^1$ is isopropyl. In other embodiment, $R^1$ is t-butyl. In other embodiments, $R^1$ is $CR^{1a}R^{1b}R^{1c}$, and $R^{1a}$ and $R^{1b}$ form a 3-6 membered cycloalkyl or 3-6 membered heterocyclyl, and $R^{1c}$ is H or $(C_{1-2})$alkyl. In some embodiments, $R^{1a}$ and $R^{1b}$ form a cyclopropyl, cyclobutyl, cyclopentyl or tetrahydropyranyl. In some such embodiments, $R^{1c}$ is H or $CH_3$. In some embodiments of formula (I), $R^1$ is cyclopropyl, cyclobutyl, cyclopentyl, tetrahydropyranyl, 1-methyl-cyclopropyl, 1-methyl-cylopentyl, 1-methyl-tetrahydropyranyl or 4-methyl-tetrahydropyranyl. In one embodiment, $R^1$ is cyclopropyl. In one embodiment, $R^1$ is cyclobutyl. In one embodiment, $R^1$ is cyclopentyl. In one embodiment, $R^1$ is tetrahydropyranyl. In a specific embodiment, $R^1$ is 1-methyl-tetrahydropyranyl. In a specific embodiment, $R^1$ is 4-methyl-tetrahydropyranyl. In a more specific embodiment, $R^1$ is 4-methyl-tetrahydropyran-4-yl.

In some embodiments of compounds formula (I), $R^2$ is L-$R^{2a}$ and $R^{2a}$ is selected from pyrolidinyl, piperidyl, piperazinyl, or imidazolyl. In some embodiments of compounds formula (I), $R^2$ is L-$R^{2a}$ and $R^{2a}$ is selected from unsubstituted pyrolidinyl, piperidyl, piperazinyl, or imidazolyl. In some such embodiments, L is a bond, —$CH_2$— or —$CH_2CH_2$—. In others, $R^2$ is substituted with $CH_3$, $CH_2CH_3$, or $CH_2CH_2NH_2$. In still other embodiments, $R^2$ is piperidyl, pyrrolidyl, $CH_2$-pyrrolidyl, $CH_2CH_2$-pyrrolidyl, $CH_2$-piperidyl, $CH_2CH_2$-piperidyl, $CH_2CH_2$-imidazolyl, or $CH_2CH_2$-piperazinyl. In one embodiment, $R^2$ is piperidyl. In one embodiment, $R^2$ is pyrrolidyl. In one embodiment, $R^2$ is $CH_2$-pyrrolidyl. In one embodiment, $R^2$ is $CH_2CH_2$-pyrrolidyl. In one embodiment, $R^2$ is $CH_2$-piperidyl. In one embodiment, $R^2$ is $CH_2CH_2$-piperidyl. In one embodiment, $R^2$ is $CH_2CH_2$-imidazolyl. In one embodiment, $R^2$ is $CH_2CH_2$-piperazinyl.

In yet other embodiments, $R^2$ is L-$R^{2b}$ and $R^{2b}$ is $CH_2NR_2$ or $CH_2CH_2NR_2$. In some such embodiments, L is a bond, —$CH_2$— or —$CH_2CH_2$—. For example, $R^2$ is $CH_2CH_2CH_2NH_2$, or $CH_2CH_2CH_2N(CH_3)_2$. In one embodiment, $R^2$ is $CH_2CH_2CH_2NH_2$. In one embodiment, $R^2$ is $CH_2CH_2CH_2N(CH_3)_2$.

In some embodiments of compounds formula (I), $R^3$ is phenyl substituted with at least one halogen, CN, fluorinated ($C_{1-2}$)alkyl, or O-fluorinated($C_{1-2}$)alkyl. In some such embodiments, $R^3$ is substituted with at least one F, Cl, CN, $CHF_2$, $CF_3$, or $OCF_3$.

In some embodiments, $R^3$ is meta-substituted phenyl, for example, $R^3$ is meta-Cl-phenyl, meta-CN-phenyl, meta-$CF_3$-phenyl, or meta-$OCF_3$-phenyl. In embodiment, $R^3$ is meta-Cl-phenyl. In embodiment, $R^3$ is meta-CN-phenyl, In embodiment, $R^3$ is meta-$CHF_2$-phenyl. In embodiment, $R^3$ is meta-$CF_3$-phenyl. In embodiment, $R^3$ is meta-$OCF_3$-phenyl.

In still other embodiments, $R^3$ is bis-meta-substituted phenyl, wherein each substituent is independently F, Cl, or $CF_3$. In one embodiment, $R^3$ is bis-meta-substituted phenyl, wherein each substituent is F. In one embodiment, $R^3$ is bis-meta-substituted phenyl, wherein each substituent is Cl. In one embodiment, $R^3$ is bis-meta-substituted phenyl, wherein one substituent is F and one substituent is Cl.

In some embodiments, $R^3$ is para-substituted phenyl, for example, para-$OCF_3$-phenyl, para-$CF_3$-phenyl, para-CN-phenyl, or para-Cl-phenyl. In one embodiment, $R^3$ is para-Cl-phenyl. In one embodiment, $R^3$ is para-$OCF_3$-phenyl. In one embodiment, $R^3$ is para-$CF_3$-phenyl. In one embodiment, $R^3$ is para-CN-phenyl. In one embodiment, $R^3$ is para-$OCF_3$-phenyl. In some embodiments, $R^3$ is meta-$C_1$, meta-$CF_3$-phenyl, meta-Cl, meta-$OCF_3$-phenyl, or meta-Cl, meta-F-phenyl. In one embodiment, $R^3$ is ortho-F, meta-Cl-phenyl. In one embodiment, $R^3$ is meta-Cl, para-Cl-phenyl. In other embodiments, $R^3$ is pyridyl, substituted with at least one halogen, fluorinated ($C_{1-2}$)alkyl, or O-fluorinated($C_{1-2}$) alkyl. In some such embodiments, $R^3$ is substituted with at least one Cl, or $CF_3$.

In some embodiments of compounds of formula (I), wherein $R^1$ is $CR^{1a}R^{1b}R^{1c}$, $R^{1a}$ and $R^{1b}$ form a 3-6 membered cycloalkyl or 3-6 membered heterocyclyl, and $R^{1c}$ is H or ($C_{1-2}$)alkyl, $R^2$ is piperidyl, pyrrolidyl, $CH_2$-pyrrolidyl, $CH_2CH_2$-pyrrolidyl, $CH_2$-piperidyl, $CH_2CH_2$-piperidyl, $CH_2CH_2$-imidazolyl, or $CH_2CH_2$-piperazinyl. In some such embodiments, $R^2$ is substituted with $CH_3$, $CH_2CH_3$, or $CH_2CH_2NH_2$. In some such embodiments, $R^3$ is phenyl substituted with at least one halogen, CN, fluorinated ($C_{1-2}$)alkyl, or O-fluorinated($C_{1-2}$)alkyl. In some such embodiments, $R^3$ is meta-substituted phenyl, or bis-meta-substituted phenyl. In some such embodiments, $R^1$ is cyclopropyl, cyclobutyl, cyclopentyl, tetrahydropyranyl, 1-methyl-cyclopropyl, 1-methyl-cylopentyl, or 1-methyl-tetrahydropyranyl. In some such embodiments, $R^3$ is meta-substituted phenyl, or bis-meta-substituted phenyl. In others, $R^3$ is meta-Cl-phenyl, meta-CN-phenyl, meta-$CF_3$-phenyl, or meta-$OCF_3$-phenyl, or $R^3$ is bis-meta-substituted phenyl, wherein each substituent is independently F, Cl, or $CF_3$.

Further embodiments provided herein include combinations of at least one of the particular embodiments set forth above.

Representative compounds of formula (I) are set forth in Table 1.

In one embodiment, the compound is 9-(2-(1H-imidazol-1-yl)ethyl)-N2-tert-butyl-N8-(3-chlorophenyl)-9H-purine-2,8-diamine.

In one embodiment, the compound is N2-tert-butyl-9-(piperidin-4-yl)-N8-(4-(trifluoromethyl)phenyl)-9H-purine-2,8-diamine.

In one embodiment, the compound is N2-tert-butyl-9-(piperidin-4-yl)-N8-(3-(trifluoromethyl)phenyl)-9H-purine-2,8-diamine.

In one embodiment, the compound is 9-(1-(2-aminoethyl)piperidin-4-yl)-N2-tert-butyl-N8-(3-(trifluoromethyl)phenyl)-9H-purine-2,8-diamine.

In one embodiment, the compound is 9-(1-(2-aminoethyl)piperidin-4-yl)-N2-tert-butyl-N8-(4-(trifluoromethyl)phenyl)-9H-purine-2,8-diamine.

In one embodiment, the compound is N2-tert-butyl-N8-(3,4-dichlorophenyl)-9-(piperidin-4-yl)-9H-purine-2,8-diamine.

In one embodiment, the compound is N2-tert-butyl-N8-(4-chlorophenyl)-9-(piperidin-4-yl)-9H-purine-2,8-diamine.

In one embodiment, the compound is N2-tert-butyl-N8-(3,4-dichlorophenyl)-9-(pyrrolidin-3-yl)-9H-purine-2,8-diamine.

In one embodiment, the compound is N2-tert-butyl-9-(pyrrolidin-3-yl)-N8-(4-(trifluoromethyl)phenyl)-9H-purine-2,8-diamine.

In one embodiment, the compound is N2-tert-butyl-9-(pyrrolidin-3-yl)-N8-(3-(trifluoromethyl)phenyl)-9H-purine-2,8-diamine.

In one embodiment, the compound is 9-(3-aminopropyl)-N2-tert-butyl-N8-(3-(trifluoromethyl)phenyl)-9H-purine-2,8-diamine.

In one embodiment, the compound is N2-tert-butyl-N8-(4-chlorophenyl)-9-(pyrrolidin-3-yl)-9H-purine-2,8-diamine.

In one embodiment, the compound is N2-tert-butyl-9-(2-(pyrrolidin-1-yl)ethyl)-N8-(3-(trifluoromethyl)phenyl)-9H-purine-2,8-diamine.

In one embodiment, the compound is 4-(2-(tert-butylamino)-9-(piperidin-4-yl)-9H-purin-8-ylamino)benzonitrile.

In one embodiment, the compound is N2-(4-methyltetrahydro-2H-pyran-4-yl)-9-(piperidin-4-yl)-N8-(4-(trifluoromethyl)phenyl)-9H-purine-2,8-diamine.

In one embodiment, the compound is N8-(3-chlorophenyl)-N2-(4-methyltetrahydro-2H-pyran-4-yl)-9-(2-(piperidin-1-yl)ethyl)-9H-purine-2,8-diamine.

In one embodiment, the compound is N8-(3-chlorophenyl)-N2-(4-methyltetrahydro-2H-pyran-4-yl)-9-(2-(pyrrolidin-1-yl)ethyl)-9H-purine-2,8-diamine.

In one embodiment, the compound is N2-tert-butyl-9-(2-(pyrrolidin-3-yl)ethyl)-N8-(3-(trifluoromethyl)phenyl)-9H-purine-2,8-diamine.

In one embodiment, the compound is N2-tert-butyl-9-(2-(pyrrolidin-2-yl)ethyl)-N8-(3-(trifluoromethyl)phenyl)-9H-purine-2,8-diamine.

In one embodiment, the compound is N2-tert-butyl-N8-(3,5-dichlorophenyl)-9-(piperidin-4-yl)-9H-purine-2,8-diamine.

In one embodiment, the compound is N2-tert-butyl-9-(piperidin-4-yl)-N8-(4-(trifluoromethoxy)phenyl)-9H-purine-2,8-diamine.

In one embodiment, the compound is N2-tert-butyl-9-(2-(piperazin-1-yl)ethyl)-N8-(3-(trifluoromethyl)phenyl)-9H-purine-2,8-diamine.

In one embodiment, the compound is N2-tert-butyl-9-(piperidin-4-ylmethyl)-N8-(3-(trifluoromethyl)phenyl)-9H-purine-2,8-diamine.

In one embodiment, the compound is N2-tert-butyl-9-(pyrrolidin-3-ylmethyl)-N8-(3-(trifluoromethyl)phenyl)-9H-purine-2,8-diamine.

In one embodiment, the compound is N2-(4-methyltetrahydro-2H-pyran-4-yl)-9-(piperidin-4-yl)-N8-(3-(trifluoromethyl)phenyl)-9H-purine-2,8-diamine.

In one embodiment, the compound is N2-tert-butyl-N8-(3-chloro-5-fluorophenyl)-9-(piperidin-4-yl)-9H-purine-2,8-diamine.

In one embodiment, the compound is N2-tert-butyl-N8-(3-chloro-5-(trifluoromethyl)phenyl)-9-(piperidin-4-yl)-9H-purine-2,8-diamine.

In one embodiment, the compound is N2-tert-butyl-N8-(3,5-difluorophenyl)-9-(piperidin-4-yl)-9H-purine-2,8-diamine.

In one embodiment, the compound is N2-tert-butyl-9-(piperidin-4-yl)-N8-(3-(trifluoromethoxy)phenyl)-9H-purine-2,8-diamine.

In one embodiment, the compound is N2-tert-butyl-N8-(5-chloropyridin-3-yl)-9-(piperidin-4-yl)-9H-purine-2,8-diamine.

In one embodiment, the compound is N2-tert-butyl-9-(piperidin-4-yl)-N8-(2-(trifluoromethyl)pyridin-4-yl)-9H-purine-2,8-diamine.

In one embodiment, the compound is N2-tert-butyl-9-(3-(dimethylamino)propyl)-N8-(3-(trifluoromethyl)phenyl)-9H-purine-2,8-diamine.

In one embodiment, the compound is N2-tert-butyl-N8-(3-(difluoromethyl)phenyl)-9-(piperidin-4-yl)-9H-purine-2,8-diamine.

In one embodiment, the compound is N2-cyclopropyl-N8-(3,5-dichlorophenyl)-9-(piperidin-4-yl)-9H-purine-2,8-diamine.

In one embodiment, the compound is 9-(1-(2-aminoethyl)piperidin-4-yl)-N2-tert-butyl-N8-(3,5-dichlorophenyl)-9H-purine-2,8-diamine.

In one embodiment, the compound is N2-tert-butyl-N8-(3,4-dichlorophenyl)-9-(1-methylpiperidin-4-yl)-9H-purine-2,8-diamine.

In one embodiment, the compound is N2-tert-butyl-N8-(3,4-dichlorophenyl)-9-(1-ethylpiperidin-4-yl)-9H-purine-2,8-diamine.

In one embodiment, the compound is N2-tert-butyl-N8-(3,5-dichlorophenyl)-9-(pyrrolidin-3-yl)-9H-purine-2,8-diamine.

In one embodiment, the compound is 9-(1-(2-aminoethyl)piperidin-4-yl)-N2-tert-butyl-N8-(3-chloro-5-(trifluoromethyl)phenyl)-9H-purine-2,8-diamine.

In one embodiment, the compound is N8-(3-chloro-5-(trifluoromethyl)phenyl)-N2-cyclopropyl-9-(piperidin-4-yl)-9H-purine-2,8-diamine.

In one embodiment, the compound is N8-(3,5-dichlorophenyl)-N2-(1-methylcyclopropyl)-9-(piperidin-4-yl)-9H-purine-2,8-diamine.

In one embodiment, the compound is N8-(3-chloro-5-(trifluoromethyl)phenyl)-N2-(1-methylcyclopropyl)-9-(piperidin-4-yl)-9H-purine-2,8-diamine.

In one embodiment, the compound is N8-(3,5-dichlorophenyl)-N2-isopropyl-9-(piperidin-4-yl)-9H-purine-2,8-diamine.

In one embodiment, the compound is N8-(3-chloro-5-(trifluoromethyl)phenyl)-N2-isopropyl-9-(piperidin-4-yl)-9H-purine-2,8-diamine.

In one embodiment, the compound is N2-tert-butyl-N8-(3-chloro-5-(trifluoromethyl)phenyl)-9-(pyrrolidin-3-yl)-9H-purine-2,8-diamine.

In one embodiment, the compound is 9-(piperidin-4-yl)-N2-(tetrahydro-2H-pyran-4-yl)-N8-(3-(trifluoromethyl)phenyl)-9H-purine-2,8-diamine.

In one embodiment, the compound is N2-tert-butyl-N8-(3-chloro-2-fluorophenyl)-9-(piperidin-4-yl)-9H-purine-2,8-diamine.

In one embodiment, the compound is N2-tert-butyl-N8-(3-chloro-5-(trifluoromethoxy)phenyl)-9-(piperidin-4-yl)-9H-purine-2,8-diamine.

In one embodiment, the compound is N8-(3,5-bis(trifluoromethyl)phenyl)-N2-tert-butyl-9-(piperidin-4-yl)-9H-purine-2,8-diamine.

In one embodiment, the compound is 3-(2-(tert-butylamino)-9-(piperidin-4-yl)-9H-purin-8-ylamino)benzonitrile.

In one embodiment, the compound is N8-(3-chloro-5-(trifluoromethyl)phenyl)-9-(piperidin-4-yl)-N2-(tetrahydro-2H-pyran-4-yl)-9H-purine-2,8-diamine.

In one embodiment, the compound is N8-(3-chloro-5-(trifluoromethyl)phenyl)-N2-cyclobutyl-9-(piperidin-4-yl)-9H-purine-2,8-diamine.

In one embodiment, the compound is N8-(3-chloro-5-(trifluoromethyl)phenyl)-N2-cyclopentyl-9-(piperidin-4-yl)-9H-purine-2,8-diamine.

In one embodiment, the compound is N8-(3-chloro-5-(trifluoromethyl)phenyl)-N2-(4-methyltetrahydro-2H-pyran-4-yl)-9-(piperidin-4-yl)-9H-purine-2,8-diamine.

In one embodiment, the compound is N2-(4-methyltetrahydro-2H-pyran-4-yl)-9-(piperidin-4-yl)-N8-(3-(trifluoromethoxy)phenyl)-9H-purine-2,8-diamine.

In one embodiment, the compound is N8-(3-chloro-5-fluorophenyl)-N2-(4-methyltetrahydro-2H-pyran-4-yl)-9-(piperidin-4-yl)-9H-purine-2,8-diamine.

In one embodiment, the compound is N8-(3-(difluoromethyl)phenyl)-N2-(4-methyltetrahydro-2H-pyran-4-yl)-9-(piperidin-4-yl)-9H-purine-2,8-diamine.

In one embodiment, the compound is N2-(4-methyltetrahydro-2H-pyran-4-yl)-9-(2-(pyrrolidin-3-yl)ethyl)-N8-(3-(trifluoromethyl)phenyl)-9H-purine-2,8-diamine.

In one embodiment, the compound is N2-(1-methylcyclopentyl)-9-(piperidin-4-yl)-N8-(3-(trifluoromethyl)phenyl)-9H-purine-2,8-diamine.

In one embodiment, the compound is N8-(3,5-dichlorophenyl)-N2-(4-methyltetrahydro-2H-pyran-4-yl)-9-(piperidin-4-yl)-9H-purine-2,8-diamine.

In one embodiment, the compound is N8-(3-chloro-5-fluorophenyl)-N2-cyclopropyl-9-(piperidin-4-yl)-9H-purine-2,8-diamine.

In one embodiment, the compound is N8-(3-chloro-5-fluorophenyl)-N2-isopropyl-9-(piperidin-4-yl)-9H-purine-2,8-diamine.

In one embodiment, the compound is N8-(3-chloro-5-fluorophenyl)-N2-(1-methylcyclopropyl)-9-(piperidin-4-yl)-9H-purine-2,8-diamine.

In one embodiment, the compound is N8-(3,4-dichlorophenyl)-N2-isopropyl-9-(piperidin-4-yl)-9H-purine-2,8-diamine.

In one embodiment, the compound is N2-isopropyl-9-(piperidin-4-yl)-N8-(3-(trifluoromethyl)phenyl)-9H-purine-2,8-diamine.

In one embodiment, the compound is N8-(3-chloro-5-(trifluoromethyl)phenyl)-N2-(1-methylcyclobutyl)-9-(piperidin-4-yl)-9H-purine-2,8-diamine.

In one embodiment, the compound is (S)—N2-tert-butyl-N8-(3-chloro-5-(trifluoromethyl)phenyl)-9-(pyrrolidin-3-yl)-9H-purine-2,8-diamine.

In one embodiment, the compound is N8-(3-chloro-5-(trifluoromethyl)phenyl)-N2-cyclobutyl-9-(pyrrolidin-3-yl)-9H-purine-2,8-diamine.

In one embodiment, the compound is N8-(3-chloro-5-(trifluoromethyl)phenyl)-N2-cyclobutyl-9-(pyrrolidin-3-yl)-9H-purine-2,8-diamine.

In one embodiment, the compound is N8-(3-chloro-5-(trifluoromethyl)phenyl)-N2-isopropyl-9-(pyrrolidin-3-yl)-9H-purine-2,8-diamine.

In one embodiment, the compound is N8-(3-chloro-5-(trifluoromethyl)phenyl)-N2-(1-methylcyclopentyl)-9-(pyrrolidin-3-yl)-9H-purine-2,8-diamine.

In one embodiment, the compound is N8-(3,5-dichlorophenyl)-N2-(1-methylcyclopentyl)-9-(pyrrolidin-3-yl)-9H-purine-2,8-diamine.

In one embodiment, the compound is N8-(3-chloro-5-(trifluoromethyl)phenyl)-N2-(1-methylcyclopropyl)-9-(pyrrolidin-3-yl)-9H-purine-2,8-diamine.

In one embodiment, the compound is N8-(3,5-dichlorophenyl)-N2-(1-methylcyclopropyl)-9-(pyrrolidin-3-yl)-9H-purine-2,8-diamine.

In one embodiment, the compound is N2-tert-butyl-9-(octahydro-1H-isoindol-5-yl)-N8-(3-(trifluoromethyl)phenyl)-9H-purine-2,8-diamine.

In one embodiment, the compound is N8-(4-chloro-3-(trifluoromethyl)phenyl)-N2-isopropyl-9-(piperidin-4-yl)-9H-purine-2,8-diamine.

In one embodiment, the compound is N8-(4-chloro-3-(trifluoromethyl)phenyl)-N2-cyclopropyl-9-(piperidin-4-yl)-9H-purine-2,8-diamine.

In one embodiment, the compound is N8-(3-chloro-4-(trifluoromethyl)phenyl)-N2-cyclopropyl-9-(piperidin-4-yl)-9H-purine-2,8-diamine.

In one embodiment, the compound is N2-tert-butyl-N8-(3-chloro-4-(trifluoromethyl)phenyl)-9-(piperidin-4-yl)-9H-purine-2,8-diamine.

In one embodiment, the compound is N8-(3-chloro-4-(trifluoromethyl)phenyl)-N2-cyclobutyl-9-(piperidin-4-yl)-9H-purine-2,8-diamine.

In one embodiment, the compound is N8-(3,5-bis(trifluoromethyl)phenyl)-N2-isopropyl-9-(piperidin-4-yl)-9H-purine-2,8-diamine.

In one embodiment, the compound is N8-(3,5-bis(trifluoromethyl)phenyl)-N2-cyclopentyl-9-(piperidin-4-yl)-9H-purine-2,8-diamine.

In one embodiment, the compound is N8-(3,5-bis(trifluoromethyl)phenyl)-N2-cyclobutyl-9-(piperidin-4-yl)-9H-purine-2,8-diamine.

In one embodiment, the compound is N8-(4-chloro-3-(trifluoromethyl)phenyl)-N2-cyclopentyl-9-(piperidin-4-yl)-9H-purine-2,8-diamine.

In one embodiment, the compound is N2-tert-butyl-N8-(4-chloro-3-(trifluoromethyl)phenyl)-9-(piperidin-4-yl)-9H-purine-2,8-diamine.

In one embodiment, the compound is N8-(4-chloro-3-(trifluoromethyl)phenyl)-N2-(1-methylcyclopropyl)-9-(piperidin-4-yl)-9H-purine-2,8-diamine.

In one embodiment, the compound is N8-(4-chloro-3-(trifluoromethyl)phenyl)-N2-(1-methylcyclopentyl)-9-(piperidin-4-yl)-9H-purine-2,8-diamine.

In one embodiment, the compound is N8-(3-chloro-4-(trifluoromethyl)phenyl)-N2-isopropyl-9-(piperidin-4-yl)-9H-purine-2,8-diamine.

In one embodiment, the compound is N8-(3-chloro-4-(trifluoromethyl)phenyl)-N2-cyclopentyl-9-(piperidin-4-yl)-9H-purine-2,8-diamine.

In one embodiment, the compound is N8-(3-chloro-4-(trifluoromethyl)phenyl)-N2-(1-methylcyclopropyl)-9-(piperidin-4-yl)-9H-purine-2,8-diamine.

In one embodiment, the compound is N8-(3-chloro-4-(trifluoromethyl)phenyl)-N2-(1-methylcyclopentyl)-9-(piperidin-4-yl)-9H-purine-2,8-diamine.

In one embodiment, the compound is N2-tert-butyl-9-(octahydrocyclopenta[c]pyrrol-5-yl)-N8-(3-(trifluoromethyl)phenyl)-9H-purine-2,8-diamine.

In one embodiment, the compound is N8-(3,5-bis(trifluoromethyl)phenyl)-N2-cyclopropyl-9-(piperidin-4-yl)-9H-purine-2,8-diamine.

In one embodiment, the compound is 9-(azetidin-3-yl)-N2-tert-butyl-N8-(3-chloro-5-(trifluoromethyl)phenyl)-9H-purine-2,8-diamine.

In one embodiment, the compound is N2-tert-butyl-N8-(3-chloro-5-(trifluoromethyl)phenyl)-9-(pyrrolidin-3-ylmethyl)-9H-purine-2,8-diamine.

Each of the compounds in Table 1 was tested in at least one of the in vitro malaria assays and was found to have activity therein.

Methods for Making Purine Compounds

The Purine Compounds of Formula I can be made using conventional organic syntheses and commercially available starting materials. By way of example and not limitation, Purine Compounds of formula (I) can be prepared as described in U.S. Pat. Nos. 7,723,340, and 8,158,635, or as outlined in Scheme 1, shown below, as well as in the examples set forth herein. It should be noted that one skilled in the art would know how to modify the procedures set forth in the illustrative schemes and examples to arrive at the desired products.

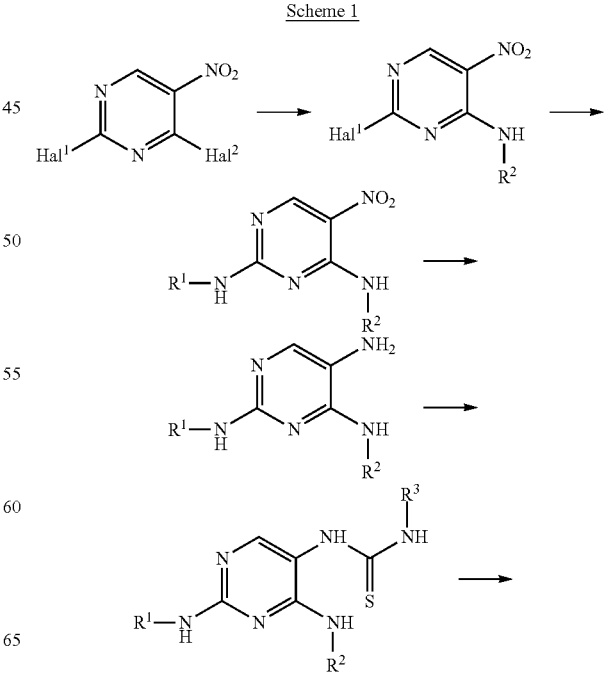

Scheme 1

As shown in Scheme 1, compounds of formula (I), wherein R¹, R² and R³ are as defined herein, can be prepared starting from an appropriately derivatized nitropyrimidine, wherein $Hal^1$ is Cl, and $Hal^2$ is Cl. Treatment of the dihalogenated nitropyrimidine with the appropriate $R^2NH_2$ amine derivative, in the presence of a base, such as, for example, DIEA, TEA, sodium carbonate, sodium bicarbonate or pyridine, in a solvent, such as for example, DCM, DMF, dioxane or THF, at reduced temperature (for example, −78° C.), provided incorporation of the $R^2$ sidechain. Treatment of this product with $R^1NH_2$, in the presence of a base, such as, for example, DIEA, TEA, sodium carbonate, sodium bicarbonate or pyridine, in a solvent, such as for example, DCM, DMF, dioxane or THF, at temperatures ranging from 0-60° C., resulted in incorporation of the $R^1$ sidechain. Reduction of the nitro moiety, using, a reducing agent in a solvent (for example, hydrogen in the presence of a catalyst such as Pd/C, in a solvent, such as MeOH or ethyl acetate, or iron in the presence of ammonium chloride in a solvent, such as for example, EtOH, MeOH or water) provided the aminopyrimidine derivative. The aminopyrimidine derivative was treated with $R^3NCS$, in a solvent, such as THF, DMF, NMP, dioxane, or EtOH, to obtain the (optionally isolated) thiourea derivative, which was cyclized, using for example, EDC or DIC, in a solvent, for example, THF, dioxane, NMP or DMF, optionally at elevated temperature (for example, 40-80° C.), to provide compounds of formula (I).

In one aspect, provided herein are methods for preparing a Purine Compound of formula (I):

the methods comprising contacting a compound of formula (Ia)

with EDC or DIC, in a solvent, under conditions suitable to provide a Purine Compound of formula (I), wherein:
$R^1$ is $CR^{1a}R^{1b}R^{1c}$, wherein $R^{1a}$ and $R^{1b}$ are $(C_{1-4})$alkyl and $R^{1c}$ is H or $(C_{1-4})$alkyl; or $R^{1a}$ and $R^{1b}$ form a 3-6 membered cycloalkyl or 3-6 membered heterocyclyl, and $R^{1c}$ is H or $(C_{1-4})$alkyl;
$R^2$ is $L-R^{2a}$ or $L-R^{2b}$,
L is a bond or $(C_{1-2}$ alkyl);
$R^{2a}$ is 3-6 membered N-containing heterocyclyl or heteroaryl, each optionally substituted with one or more $(C_{1-4})$alkyl, or $(C_{1-4})$alkyl-$NR_2$;
$R^{2b}$ is $(C_{1-4}$ branched or unbranched alkyl)-$NR_2$,
$R^3$ is phenyl or pyridyl, substituted with at least one halogen, CN, $(C_{1-4})$alkyl, or $O(C_{1-4})$alkyl, wherein the alkyl is optionally fluorinated; and
R is H or $(C_{1-4})$ alkyl;
provided the compound is not
4-(2-(isopropylamino)-8-((2,4,6-trifluorophenyl)amino)-9H-purin-9-yl)pyrrolidin-2-one;
$N^2$-cyclopentyl-$N^8$-(2-fluorophenyl)-9-(piperidin-4-yl)-9H-purine-2,8-diamine; or
$N^2$-cyclohexyl-$N^8$-(2-fluorophenyl)-9-(piperidin-4-ylmethyl)-9H-purine-2,8-diamine.

In one embodiment, the solvent is THF, dioxane, NMP or DMF. In some embodiments, the contacting is optionally performed at elevated temperature, for example, from about 40° C. to about 80° C.

In some embodiments, the methods further comprise preparing a compound of formula (Ia):

the methods comprising contacting a compound of formula (Ib)

with $R^3NCS$, in a solvent, under conditions suitable to provide a compound of formula (Ia).

In one embodiment, the solvent is THF, DMF, NMP, dioxane, or EtOH.

In some embodiments, the methods further comprise preparing a compound of formula (Ib):

the methods comprising reducing a compound of formula (Ic)

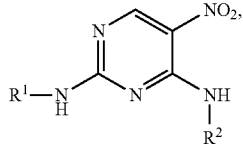
(Ic)

with a reducing agent, in a solvent, under conditions suitable to provide a compound of formula (Ib).

In one embodiment, the reducing agent is H2 in the presence of a catalyst. In some such embodiments, the catalyst Pd/C. In some such embodiments, the solvent is MeOH or ethyl acetate. In other embodiments, the reducing agent is iron in the presence of ammonium chloride. In some such embodiments, the solvent is EtOH, MeOH or water.

In some embodiments, the methods further comprise preparing a compound of formula (Ic):

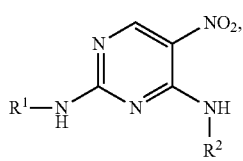
(Ic)

the methods comprising contacting a compound of formula (Id)

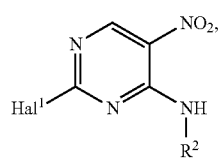
(Id)

with $R^1NH_2$, in the presence of a base, in a solvent, under conditions suitable to provide a compound of formula (Ic), wherein $Hal^1$ is Cl.

In some embodiments, the base is DIEA, TEA, sodium carbonate, sodium bicarbonate, or pyridine. In other embodiments, the solvent is DCM, DMF, dioxane or THF. In some embodiments, the contacting is performed at elevated temperature, for example, from about 0° C. to about 60° C.

In some embodiments, the methods further comprise preparing a compound of formula (Id):

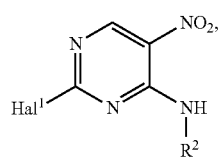
(Id)

the methods comprising contacting a compound of formula (Ie)

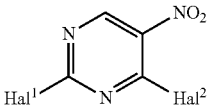
(Ie)

with $R^2NH_2$, in the presence of a base, in a solvent, under conditions suitable to provide a compound of formula (Id), wherein $Hal^2$ is Cl.

In some embodiments, the base is DIEA, TEA, sodium carbonate, sodium bicarbonate, or pyridine. In other embodiments, the solvent is DCM, DMF, dioxane or THF. In some embodiments, the contacting is performed at reduced temperature, for example, about −78° C.

Methods of Use

The Purine Compounds have utility as pharmaceuticals to treat, prevent or improve conditions in animals or humans. The Purine Compounds provided herein are intended for use in the treatment or prevention of all diseases, disorders or conditions disclosed herein. Accordingly, the Purine Compounds provided herein are for use as a medicament. Accordingly, provided herein are the Purine Compounds for use in the treatment or prevention of malaria. The methods provided herein comprise the administration of an effective amount of at least one Purine Compound(s) to a subject in need thereof.

In one aspect provided herein are compounds for use in treating or preventing malaria, comprising administering to a subject in need thereof an effective amount of a Purine Compound, as described herein.

In another aspect provided herein are methods for treating or preventing malaria, comprising administering to a subject in need thereof an effective amount of a Purine Compound, as described herein.

In one embodiment, provided herein are methods for treating or preventing malaria, comprising administering to a subject in need thereof an effective amount of a Purine Compound of Formula (I) as described herein. In one embodiment, provided herein is a Purine Compound of Formula (I) for use in methods for treating or preventing malaria, comprising administering to a subject in need thereof an effective amount of the compound of Formula (I) as described herein. In one embodiment, the Purine Compound of Formula (I) is selected from Table 1. In some embodiments, the malaria is caused by *Plasmodium falciparum, Plasmodium vivax, Plasmodium ovale, Plasmodium knowlesi* or *Plasmodium malariae*. In one embodiment, the malaria is caused by *Plasmodium falciparum*. In some embodiments, the methods additionally comprise administering an effective amount of at least one of chloroquine, quinine, quinidine, mefloquine, atovaquone, proguanil, doxycycline, artesunate, artemether, artemisinin, lumefantrine, amodiaquine, hydroxychloroquine, halofantrine, pyrimethamine, sulfadoxine, or primaquine.

In a further embodiment provided herein is a compound of Formula (I) or for use in a method described herein.

Pharmaceutical Compositions and Routes of Administration

Provided herein are pharmaceutical compositions comprising an effective amount of a Purine Compound as described herein, and a pharmaceutically acceptable carrier, excipient or vehicle.

The Purine Compounds can be administered to a subject enterally (for example, orally, rectally), topically or parenterally (for example, intravenously, intramuscularly, subcutaneously), in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), a cosolvent (e.g., propylene glocyl/glycofurol), a buffer, a copolymer (e.g., poly(lactic-co-glycolic acid, i.e. PLGA), and base wax (e.g., cocoa butter, white petrolatum or polyethylene glycol). The effective amount of the Purine Compounds in the pharmaceutical composition may be at a level that will exercise the desired effect; for example, at about 0.005 mg/kg of a subject's body weight to about 20 mg/kg of a subject's body weight in unit dosage for both oral and parenteral administration.

The dose of a Purine Compound to be administered to a subject is rather widely variable and can be subject to the judgment of a health-care practitioner. In general, the Purine Compounds can be administered one to four times a day in a dose of about 0.005 mg/kg of a subject's body weight to about 20 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, the dose is about 0.01 mg/kg of a subject's body weight to about 5 mg/kg of a subject's body weight. In one embodiment, the dose is about 0.05 mg/kg of a subject's body weight to about 1 mg/kg of a subject's body weight. In one embodiment, the dose is about 0.1 mg/kg of a subject's body weight to about 0.75 mg/kg of a subject's body weight. In one embodiment, the dose is about 0.25 mg/kg of a subject's body weight to about 0.5 mg/kg of a subject's body weight. In one embodiment, one dose is given per day. In any given case, the amount of the Purine Compound administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 1 mg/day to about 1200 mg/day. In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Purine Compound to a subject in need thereof. In one embodiment, the methods for the treatment of a disease or disorder comprise the administration of about 0.375 mg/day to about 750 mg/day of a Purine Compound to a subject in need thereof. In one embodiment, the methods for the treatment of a disease or disorder comprise the administration of about 0.75 mg/day to about 375 mg/day of a Purine Compound to a subject in need thereof. In one embodiment, the methods for the treatment of a disease or disorder comprise the administration of about 3.75 mg/day to about 75 mg/day of a Purine Compound to a subject in need thereof. In one embodiment, the methods for the treatment of a disease or disorder comprise the administration of about 7.5 mg/day to about 55 mg/day of a Purine Compound to a subject in need thereof. In one embodiment, the methods for the treatment of a disease or disorder comprise the administration of about 18 mg/day to about 37 mg/day of a Purine Compound to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Purine Compound to a subject in need thereof. In a particular embodiment, the methods disclosed herein comprise the administration of 400 mg/day, 600 mg/day or 800 mg/day of a Purine Compound to a subject in need thereof. The methods for the treatment of a disease or disorder comprise the administration of about 1 mg/day to about 1200 mg/day of a Purine Compound to a subject in need thereof. The methods for the treatment of a disease or disorder comprise the administration of about 10 mg/day to about 1200 mg/day of a Purine Compound to a subject in need thereof. The methods for the treatment of a disease or disorder comprise the administration of about 100 mg/day to about 1200 mg/day of a Purine Compound to a subject in need thereof. The methods for the treatment of a disease or disorder comprise the administration of about 400 mg/day to about 1200 mg/day of a Purine Compound to a subject in need thereof. The methods for the treatment of a disease or disorder comprise the administration of about 600 mg/day to about 1200 mg/day of a Purine Compound to a subject in need thereof. The methods for the treatment of a disease or disorder comprise the administration of about 400 mg/day to about 800 mg/day of a Purine Compound to a subject in need thereof. The methods for the treatment of a disease or disorder comprise the administration of about 600 mg/day to about 800 mg/day of a Purine Compound to a subject in need thereof. In a particular embodiment, the methods disclosed herein comprise the administration of 400 mg/day of a Purine Compound to a subject in need thereof. In another particular embodiment, the methods disclosed herein comprise the administration of 600 mg/day of a Purine Compound to a subject in need thereof. In another particular embodiment, the methods disclosed herein comprise the administration of 800 mg/day of a Purine Compound to a subject in need thereof. In another embodiment, provided herein are unit dosage formulations that comprise between about 1 mg and 500 mg, or between about 500 mg and about 1000 mg of a Purine Compound. In one embodiment, provided herein is a unit dosage formulation that comprise between about 1 mg and 500 mg of a Purine Compound. In one embodiment, provided herein is a unit dosage formulation that comprise between about 500 mg and about 1000 mg of a Purine Compound.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Purine Compound. In one embodiment, the unit dosage formulations comprises between about 1 mg and 200 mg of a Purine Compound. In one embodiment, the unit dosage formulations comprises between about 35 mg and about 1400 mg of a Purine Compound. In one embodiment, the unit dosage formulations comprises between about 125 mg and about 1000 mg of a Purine Compound. In one embodiment, the unit dosage formulations comprises between about 250 mg and about 1000 mg of a Purine Compound. In one embodiment, the unit dosage formulations comprises between about 500 mg and about 1000 mg of a Purine Compound.

In a particular embodiment, provided herein are unit dosage formulations comprising about 100 mg or 400 mg of a Purine Compound.

In another embodiment, provided herein are unit dosage formulations that comprise 1 mg, 5 mg, 10 mg, 15 mg, 20 mg, 25 mg, 30 mg, 35 mg, 40 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Purine Compound. In one embodiment the unit dosage formulations comprise 1 mg of a Purine Compound. In one embodiment the unit dosage formulations comprise 5 mg of a Purine Compound. In one embodiment the unit dosage formulations comprise 10 mg of a Purine Compound. In one embodiment the unit dosage formulations comprise 15 mg of a Purine Compound. In one embodiment the unit dosage formulations comprise 20 mg of a Purine Compound. In one embodiment the unit dosage formulations comprise 25 mg of a Purine Compound. In one embodiment the unit dosage formulations comprise 30 mg of a Purine Compound. In one embodiment the unit dosage formulations comprise 35 mg of a Purine Compound. In one embodiment the unit dosage formulations comprise 40 mg of a Purine Compound. In one embodiment the unit dosage formulations comprise 50 mg of a Purine Compound. In one embodiment the unit dosage formulations comprise 70 mg of a Purine Compound. In one embodiment the unit dosage formulations comprise 100 mg of a Purine Compound. In one embodiment the unit dosage formulations comprise 125 mg of a Purine Compound. In one embodiment the unit dosage formulations comprise 140 mg of a Purine Compound. In one embodiment the unit dosage formulations comprise 175 mg of a Purine Compound. In one embodiment the unit dosage formulations comprise 200 mg of a Purine Compound. In one embodiment the unit dosage formulations comprise 250 mg of a Purine Compound. In one embodiment the unit dosage formulations comprise 280 mg of a Purine Compound. In one embodiment the unit dosage formulations comprise 350 mg of a Purine Compound. In one embodiment the unit dosage formulations comprise 500 mg of a Purine Compound. In one embodiment the unit dosage formulations comprise 560 mg of a Purine Compound. In one embodiment the unit dosage formulations comprise 700 mg of a Purine Compound. In one embodiment the unit dosage formulations comprise 750 mg of a Purine Compound. In one embodiment the unit dosage formulations comprise 1000 mg of a Purine Compound. In one embodiment the unit dosage formulations comprise 1400 mg of a Purine Compound.

A Purine Compound can be administered once, twice, three, four or more times daily. In a particular embodiment, doses of 600 mg or less are administered as a once daily dose and doses of more than 600 mg are administered twice daily in an amount equal to one half of the total daily dose.

A Purine Compound can be administered orally for reasons of convenience. In one embodiment, when administered orally, a Purine Compound is administered with a meal and water. In another embodiment, the Purine Compound is dispersed in water or juice (e.g., apple juice or orange juice) and administered orally as a suspension.

The Purine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Purine Compound without an additional carrier, excipient or vehicle.

In another embodiment, provided herein are compositions comprising an effective amount of a Purine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories, suspensions, gels, intra-ruminal devices (e.g., for prolonged prophylaxis or controlled release), implants, topical pour-ons, transdermal delivery gels, spot-ons, implants (including devices, gels, liquids (e.g., PLGA)), and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Purine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Purine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Purine Compound can be delayed or prolonged by proper formulation. For example, a slowly soluble pellet of the Purine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Purine Compound in oily or emulsified vehicles, or adding amounts of PLGA, that allow it to disperse slowly in the serum.

In another embodiment, the Purine Compounds can be administered alone or in combination with a co-agent useful in the treatment of malaria, such as substances useful in the treatment of malaria, e.g., a co-agent including, but not limited to, at least one of chloroquine, quinine, quinidine, mefloquine, atovaquone, proguanil, doxycycline, artesunate, artemether, artemisinin, lumefantrine, amodiaquine, hydroxychloroquine, halofantrine, pyrimethamine, sulfadoxine, or primaquine.

In another embodiment, wherein the Purine Compound is administered to a subject prior to, simultaneously or sequentially with other therapeutic regimens or co-agents useful in the treatment of malaria (e.g., multiple drug regimens), in an effective amount the Purine Compounds that are administered simultaneously with said co-agents can be administered in the same or different composition(s) and by the same or different route(s) of administration.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| Boc | t-Butyloxycarbonyl |
|---|---|
| Cbz | Carboxybenzyl |
| CDI | Carbonyldiimidazole |
| DAST | Diethylaminosulfur trifluoride |
| DBU | 1 8-Diazabicyclo 5.4.0 undec-7-ene |
| DCM | Dichloromethane |
| DEA | Diethylamine |
| DIC | Diisopropylcarbodiimide |
| DIEA | Diisopropylethylamine |
| DMA | N,N-Dimethylacetamide |
| DME | 1,2-Dimethoxyethane |
| DMF | N,N-Dimethylformamide |
| DMSO | Dimethylsulfoxide |
| DPPA | Diphenylphosphoryl azide |
| EDC | Ethyl-(N',N'-dimethylamino)propylcarbodiimide hydrochloride |
| ESI | Electrospray ionization |
| EtOH | Ethanol |
| HATU | O-(7-Azabenzotriazol-1-yl)-N,N,N',N'-tetramethyluronium hexafluorophosphate |
| HBTU | O-(Benzotriazol-1-yl)- N,N,N',N'-tetramethyluronium hexafluorophosphate |
| HCl | Hydrochloric acid |
| HMPA | Hexamethylphosphoramide |
| HOBt | 1-Hydroxybenzotriazole |
| HPLC | High performance liquid chromatography |
| HTRF | Homogeneous time resolved fluorescence |
| KOAc | Potassium acetate |
| LCMS | Liquid chromatography mass spectrometry |
| mCPBA | Meta-chloroperoxybenzoic acid |
| MeOH | Methanol |
| MS | Mass spectrometry |
| MTBE | tert-Butyl Methyl ether |
| NaOH | Sodium hydroxide |
| NMM | N-Methylmorpholine |
| NMP | N-methylpyrrolidone |
| NMR | Nuclear magnetic resonance |
| pTSA | p-Toluenesulfonic acid |
| SEM | 2-Trimethylsilylethoxymethoxy |
| SFC | Supercritical fluid chromatography |
| TBTU | O-Benzotriazol-1-yl-N,N,N',N'-tetra-methyluronium tetrafluoroborate |
| t-BuOH | Tert-butanol |
| TEA | Triethylamine |
| TFA | Trifluoroacetic acid |
| THF | Tetrahydrofuran |
| THP | Tetrahydropyran |
| TLC | Thin layer chromatography |
| TMS | Trimethylsilane |

Compound Synthesis

Example 1. N2-(tert-Butyl)-N8-(3-chloro-5-fluorophenyl)-9-(piperidin-4-yl)-9H-purine-2,8-diamine

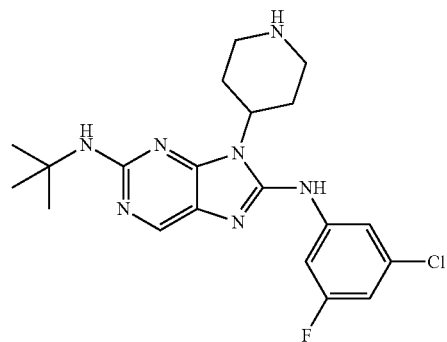

tert-Butyl 4-(2-(tert-butylamino)-8-((3-chloro-5-fluorophenyl)amino)-9H-purin-9-yl) piperidine-1-carboxylate. To a stirred solution of tert-butyl 4-((5-amino-2-(tert-butylamino)pyrimidin-4-yl)amino)piperidine-1-carboxylate (0.7 g, 2 mmol) and 1-chloro-3-fluoro-5-isothiocyanatobenzene (0.36 g, 2 mmol) in THF (10 mL) was added EDCI (0.7 g, 4 mmol) at ambient temperature. The reaction mixture was heated to 60° C. for 4 h. Completion of the reaction was confirmed by UPLC. The product was isolated and purified via standard methods to afford tert-butyl 4-(2-(tert-butylamino)-8-((3-chloro-5-fluorophenyl)amino)-9H-purin-9-yl) piperidine-1-carboxylate (0.35 g, 35%) as an off-white solid. MS (ESI) m/z 518, 519 [M, M+1]$^+$.

N2-(tert-Butyl)-N8-(3-chloro-5-fluorophenyl)-9-(piperidin-4-yl)-9H-purine-2, 8-diamine To a stirred solution of tert-butyl 4-(2-(tert-butylamino)-8-((3-chloro-5-fluorophenyl)amino)-9H-purin-9-yl)piperidine-1-carboxylate (0.35 g, 0.67 mmol) in methanol (10 mL) was added HCl in dioxane (5 mL) at 0° C. The reaction mixture was stirred at ambient temperature for 4 h. Completion of the reaction was confirmed by UPLC. The product was purified by standard methods to afford N2-(tert-butyl)-N8-(3-chloro-5-fluorophenyl)-9-(piperidin-4-yl)-9H-purine-2,8-diamine (250 mg, 82%). MS (ESI) m/z 418, 419 [M, M+1]+. $^1$H NMR (400 MHz, CD$_3$OD): δ 8.24 (s, 1H), 7.43-7.50 (m, 2H), 6.82-6.85 (m, 1H), 4.47-4.54 (m, 1H), 3.37 (s, 2H), 2.81-2.93 (m, 4H), 1.97 (m, 2H), 1.52 (s, 9H).

Example 2. N2-(tert-Butyl)-N8-(4-chlorophenyl)-9-(piperidin-4-yl)-9H-purine-2,8-diamine

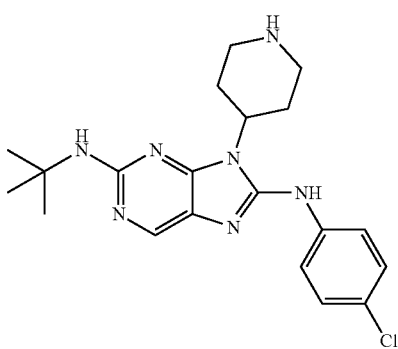 [SMILES: CC(C)(C)Nc1ncc2nc(Nc3ccc(Cl)cc3)n(C3CCNCC3)c2n1]

tert-Butyl 4-((2-chloro-5-nitropyrimidin-4-yl)amino) piperidine-1-carboxylate

To a stirred solution of 2, 4-dichloro-5-nitropyrimidine (2.5 g, 13 mmol) and DIPEA (6.6 mL, 39 mmol) in IPA (40 mL) was added tert-butyl 4-aminopiperidine-1-carboxylate (2.6 g, 13 mmol) portionwise at 0° C. under nitrogen. The reaction mixture was slowly warmed to ambient temperature and stirred for 2 h. Completion of the reaction was confirmed by UPLC. The product was isolated to afford tert-butyl 4-((2-chloro-5-nitropyrimidin-4-yl)amino)piperidine-1-carboxylate (4 g, 89%) as a pale yellow solid. MS (ESI) m/z 358 [M+1]$^+$.

tert-Butyl 4-((2-(tert-butylamino)-5-nitropyrimidin-4-yl)amino)piperidine-1-carboxylate A stirred solution of tert-butyl 4-((2-chloro-5-nitropyrimidin-4-yl)amino)piperidine-1-carboxylate (3.5 g, 10 mmol), tert-butylamine (1.1 g, 15 mmol) and sodium bicarbonate (1.6 g, 20 mmol) in DMF (40 mL) was heated to 60° C. for 4 h. Completion of the reaction was confirmed by UPLC. The product was isolated to afford tert-butyl 4-((2-(tert-butylamino)-5-nitropyrimidin-4-yl)amino)piperidine-1-carboxylate (3.5 g, 92%) as a pale yellow solid. MS (ESI) m/z 395 [M+1]$^+$.

tert-Butyl 4-((5-amino-2-(tert-butylamino)pyrimidin-4-yl)amino)piperidine-1-carboxylate To a stirred solution of tert-butyl 4-((2-(tert-butylamino)-5-nitropyrimidin-4-yl)amino)piperidine-1-carboxylate (1.8 g, 4.6 mmol) in ethanol:water (20 mL, 3:1) was added iron powder (2.6 g, 46 mmol) and ammonium chloride (0.24 g, 4.6 mmol) at ambient temperature. The reaction mixture was heated to 85° C. for 2 h. Completion of the reaction was confirmed by UPLC. The resulting reaction mixture was filtered through a bed of celite, washed with ethyl acetate and concentrated to afford tert-butyl 4-((5-amino-2-(tert-butylamino)pyrimidin-4-yl)amino)piperidine-1-carboxylate (1.6 g) as a brown solid. MS (ESI) m/z 365 [M+1]$^+$.

tert-Butyl 4-(2-(tert-butylamino)-8-((4-chlorophenyl)amino)-9H-purin-9-yl)piperidine-1-carboxylate To a stirred solution of tert-butyl-4-((5-amino-2-(tert-butylamino)pyrimidin-4-yl)amino)piperidine-1-carboxylate (0.8 g, 2.2 mmol) and 1-chloro-4-isothiocyanatobenzene (0.4 g, 2.2 mmol) in THF was added EDCI (0.8 g, 4.4 mmol) at ambient temperature. The reaction mixture was heated to 60° C. for 4 h. Completion of the reaction was confirmed by UPLC. The product was isolated and triturated with petroleum ether to afford tert-butyl 4-(2-(tert-butylamino)-8-((4-chlorophenyl)amino)-9H-purin-9-yl)piperidine-1-carboxylate (0.25 g) as a brown solid. MS (ESI) m/z 500 [M+1]$^+$.

N2-(tert-Butyl)-N8-(4-chlorophenyl)-9-(piperidin-4-yl)-9H-purine-2,8-diamine

To a stirred solution tert-butyl 4-(2-(tert-butylamino)-8-((4-chlorophenyl)amino)-9H-purin-9-yl) piperidine-1-carboxylate (0.25 g, 0.5 mmol) in methanol (5 mL) was added HCl in dioxane (3 mL) at 0° C. The reaction mixture was stirred at ambient temperature for 4 h. Completion of the reaction was confirmed by UPLC. The product was isolated and purified via standard methods to afford N2-(tert-butyl)-N8-(4-chlorophenyl)-9-(piperidin-4-yl)-9H-purine-2, 8-diamine (0.19 g, 92%). MS (ESI) m/z 400 [M+1]+. $^1$H NMR (400 MHz, CD$_3$OD): δ 8.14 (s, 1H), 7.56 (d, J=8.6 Hz, 2H), 7.32-7.36 (m, 2H), 4.45-4.47 (m, 1H), 3.27-3.33 (m, 2H), 2.76-2.86 (m, 4H), 1.91-1.93 (m, 2H), 1.52 (s, 9H).

Example 3. N2-(tert-Butyl)-N8-(3,4-dichlorophenyl)-9-(pyrrolidin-3-yl)-9H-purine-2,8-diamine

Example 4. N2-(tert-Butyl)-9-(pyrrolidin-3-yl)-N8-(3-(trifluoromethyl)phenyl)-9H-purine-2,8-diamine

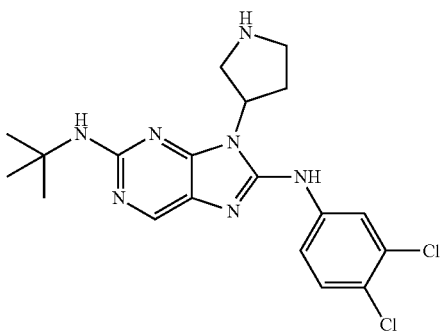 [SMILES: CC(C)(C)Nc1ncc2nc(Nc3ccc(Cl)c(Cl)c3)n(C3CCNC3)c2n1]

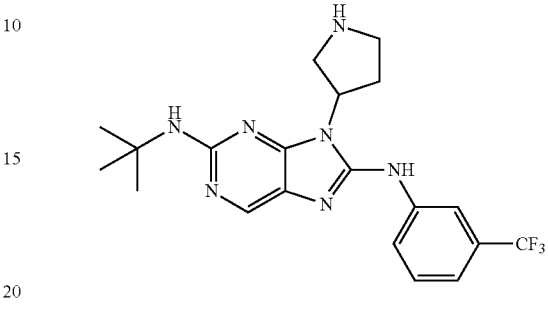

tert-Butyl 3-(2-(tert-butylamino)-8-((3,4-dichlorophenyl)amino)-9H-purin-9-yl)pyrolidine-1-carboxylate To a stirred solution of tert-butyl 3-((5-amino-2-(tert-butylamino)pyrimidin-4-yl)amino)pyrrolidine-1-carboxylate (0.6 g, 1.7 mmol) and 1,2-dichloro-4-isothiocyanatobenzene (0.35 g, 1.7 mmol) in THF was added EDCI (0.65 g, 3.4 mmol) at ambient temperature. The reaction mixture was heated to 60° C. for 4 h. Completion of the reaction was confirmed by UPLC. The product was isolated. The isolated product was triturated with petroleum ether to afford tert-butyl 3-(2-(tert-butylamino)-8-((3,4-dichlorophenyl)amino)-9H-purin-9-yl)pyrrolidine-1-carboxylate (0.5 g) as a brown solid. MS (ESI) m/z 520 [M+1]+.

N2-(tert-Butyl)-N8-(3,4-dichlorophenyl)-9-(pyrrolidin-3-yl)-9H-purine-2,8-diamine To a stirred solution of tert-butyl 3-(2-(tert-butylamino)-8-((3,4-dichlorophenyl)amino)-9H-purin-9-yl)pyrrolidine-1-carboxylate (0.5 g, 0.5 mmol) in methanol (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(tert-butyl)-N8-(3,4-dichlorophenyl)-9-(pyrrolidin-3-yl)-9H-purine-2,8-diamine (0.1 g, 23%). MS (ESI) m/z 420 [M+1]+. $^1$H NMR (400 MHz, CD$_3$OD): δ 8.17 (s, 1H), 8.07 (brs, 1H), 7.49 (d, J=8.8 Hz, 1H), 7.44 (d, J=8.8 Hz, 1H), 5.33-5.38 (m, 1H), 3.40-3.50 (m, 1H), 3.35-3.40 (m, 1H), 3.20-3.30 (m, 1H), 2.92-2.99 (m, 1H), 2.50-2.56 (m, 1H), 2.02-2.08 (m, 1H), 1.55 (s, 9H).

tert-Butyl 3-(2-(tert-butylamino)-8-((3-(trifluoromethyl)phenyl)amino)-9H-purin-9-yl) pyrrolidine-1-carboxylate To a stirred solution of tert-butyl 3-((5-amino-2-(tert-butylamino) pyrimidin-4-yl)amino)pyrrolidine-1-carboxylate (0.6 g, 1.7 mmol) and 1-isothiocyanato-3-(trifluoromethyl)benzene (0.34 g, 1.7 mmol) in THF was added EDCI (0.65 g, 3.2 mmol) at ambient temperature. The reaction mixture was heated to 60° C. for 4 h. Completion of the reaction was confirmed by UPLC. The product was isolated. The resulting isolated product was triturated with petroleum ether to afford tert-butyl 3-(2-(tert-butylamino)-8-((3-(trifluoromethyl)phenyl)amino)-9H-purin-9-yl)pyrrolidine-1-carboxylate (0.45 g) as brown solid. MS (ESI) m/z 520 [M+1]+.

N2-(tert-Butyl)-9-(pyrrolidin-3-yl)-N8-(3-(trifluoromethyl)phenyl)-9H-purine-2, 8-diamine To a stirred solution of tert-butyl 3-(2-(tert-butylamino)-8-((3-(trifluoromethyl)phenyl)amino)-9H-purin-9-yl)pyrrolidine-carboxylate (0.45 g, 0.5 mmol) in methanol (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(tert-butyl)-9-(pyrrolidin-3-yl)-N8-(3-(trifluoromethyl)phenyl)-9H-purine-2,8-diamine (0.08 g, 30%). MS (ESI) m/z 420 [M+1]+. $^1$H NMR (400 MHz, CD$_3$OD): δ 8.19 (s, 1H), 8.09 (s, 1H), 7.84 (d, J=8.4 Hz, 1H), 7.49-7.53 (m, 1H), 7.30 (d, J=8 Hz, 1H), 5.35-5.40 (m, 1H), 3.38-3.53 (m, 2H), 3.23-3.32 (m, 1H), 2.95-3.05 (m, 1H), 2.50-2.57 (m, 1H), 2.07-2.13 (m, 1H), 1.51 (s, 9H).

Example 5. 9-(3-Aminopropyl)-N2-(tert-butyl)-N8-(3-(trifluoromethyl) phenyl)-9H-purine-2,8-diamine

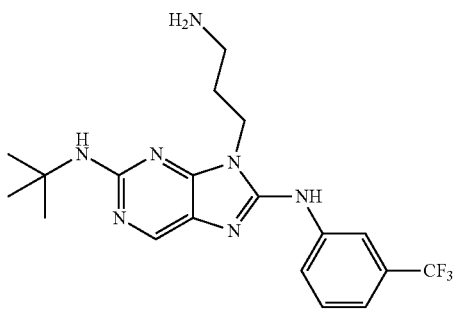 [SMILES: CC(C)(C)Nc1ncc2nc(Nc3cccc(C(F)(F)F)c3)n(CCCN)c2n1]

tert-Butyl (3-((2-chloro-5-nitropyrimidin-4-yl)amino)propyl)carbamate

To a stirred solution of 2, 4-dichloro-5-nitropyrimidine (0.7 g, 3.6 mmol) and DIPEA (1.9 mL, 10.8 mmol) in IPA (10 mL) was added portion tert-butyl (3-aminopropyl)carbamate (0.6 g, 3.6 mmol) at 0° C. under nitrogen. The reaction mixture was slowly warmed to ambient temperature and stirred for 1 h. Completion of the reaction was confirmed by UPLC. The product was isolated to afford tert-butyl (3-((2-chloro-5-nitropyrimidin-4-yl)amino)propyl) carbamate (1.4 g). MS (ESI) m/z 330, 331 [M−1,M]+.

tert-Butyl (3-((2-(tert-butylamino)-5-nitropyrimidin-4-yl)amino)propyl)carbamate To a stirred solution of tert-butyl (3-((2-chloro-5-nitropyrimidin-4-yl)amino)propyl)carbamate (1.3 g, 3.1 mmol), tert butylamine (0.6 g, 7.8 mmol) and sodium bicarbonate (0.5 g, 5.9 mmol) in DMF (12 mL) was heated to 60° C. for 4 h. Completion of the reaction was confirmed by UPLC. The product was isolated to afford tert-butyl(3-((2-(tert-butylamino)-5-nitropyrimidin-4-yl) amino)propyl)carbamate (1.4 g, 97%) as a pale yellow solid. MS (ESI) m/z 369 [M+1]+.

tert-Butyl (3-((5-amino-2-(tert-butylamino)pyrimidin-4-yl)amino)propyl)carbamate To a stirred solution of tert-butyl(3-((2-(tert-butylamino)-5-nitropyrimidin-4-yl)amino)propyl) carbamate (0.9 g, 2.4 mmol) in ethanol:water (15 mL, 3:1) was added iron powder (1.4 g, 24 mmol) and ammonium chloride (0.13 g, 2.4 mmol) at ambient temperature. Completion of the reaction was confirmed by UPLC. The resulting reaction mixture was filtered through a bed of celite, washed with ethyl acetate and concentrated to afford tert-butyl (3-((5-amino-2-(tert-butylamino)pyrimidin-4-yl)amino)propyl)carbamate (0.8 g) as a brown solid. MS (ESI) m/z 339 [M+1]+.

tert-Butyl (3-(2-(tert-butylamino)-8-((3-(trifluoromethyl)phenyl)amino)-9H-purin-9-yl)propylcarbamate To a stirred solution of tert-butyl(3-((5-amino-2-(tert-butylamino)pyrimidin-4-yl)amino)propyl)carbamate (0.8 g, 2.4 mmol) and 1-isothiocyanato-3-(trifluoromethyl)benzene (0.5 g, 2.4 mmol) in THF was added EDCI (0.9 g, 4.7 mmol) at ambient temperature. The reaction mixture was heated to 60° C. for 4 h. Completion of the reaction was confirmed by UPLC. The product was isolated and purified via standard methods to afford tert-butyl(3-(2-(tert-butylamino)-8-((3-(trifluoromethyl)phenyl)amino)-9H-purin-9-yl)propyl)carbamate (0.3 g, 25%) as brown solid. MS (ESI) m/z 508 [M+1]+.

9-(3-Aminopropyl)-N2-(tert-butyl)-N8-(3-(trifluoromethyl)phenyl)-9H-purine-2,8-diamine To a stirred solution of tert-butyl(3-(2-(tert-butylamino)-8-((3-(trifluoromethyl) phenyl)amino)-9H-purin-9-yl)propyl)carbamate (0.3 g, 0.6 mmol) in methanol (10 mL) was added HCl in dioxane (3 mL) at 0° C. The reaction mixture was stirred at ambient temperature for 4 h. Completion of the reaction was confirmed by UPLC. The product was isolated and purified via standard methods to afford 9-(3-aminopropyl)-N2-(tert-butyl)-N8-(3-(trifluoromethyl)phenyl)-9H-purine-2,8-diamine (0.12 g, 50%). MS (ESI) m/z 408 [M+1]+. 1H NMR (400 MHz, CD3OD): δ 8.18 (s, 1H), 8.06 (brs, 1H), 7.89 (d, J=7.6 Hz, 1H), 7.50-7.54 (m, 1H), 7.31 (d, J=8 Hz, 1H), 4.27 (t, J=6.4 Hz, 2H), 2.75 (t, J=6.4 Hz, 2H), 2.00-2.07 (m, 2H), 1.50 (s, 9H).

Example 6. N2-(tert-Butyl)-N8-(3-chloro-5-(trifluoromethyl) phenyl)-9-(piperidin-4-yl)-9H-purine-2,8-diamine

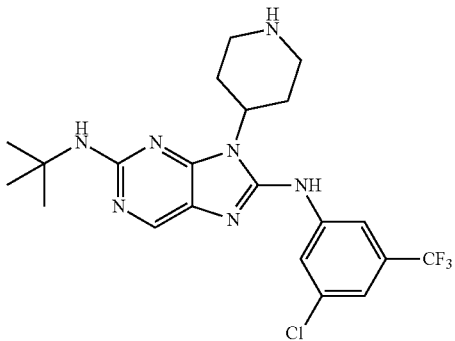 [SMILES: CC(C)(C)Nc1ncc2nc(Nc3cc(Cl)cc(C(F)(F)F)c3)n(C3CCNCC3)c2n1]

tert-Butyl 4-(2-(tert-butylamino)-8-((3-chloro-5-(trifluoromethyl)phenyl)amino)-9H-purin-9-yl)piperidine-1-carboxylate To a stirred solution of tert-butyl 4-((5-amino-2-(tert-butylamino)pyrimidin-4-yl)amino)piperidine-1-carboxylate (0.7 g, 2 mmol) and 1-chloro-3-isothiocyanato-5-(trifluoromethyl)benzene (0.5 g, 2 mmol) in THF (10 mL) was added EDCI (0.7 g, 4 mmol) at ambient temperature. The reaction mixture was heated to 60° C. for 4 h. Completion of the reaction was confirmed by UPLC. The product was isolated and purified via standard methods to afford tert-butyl 4-(2-(tert-butylamino)-8-((3-chloro-5-(trifluoromethyl) phenyl)amino)-9H-purin-9-yl)piperidine-1-carboxylate (0.5 g, 46%) as an off-white solid. MS (ESI) m/z 568, 569 [M, M+1]+.

N2-(tert-Butyl)-N8-(3-chloro-5-(trifluoromethyl) phenyl)-9-(piperidin-4-yl)-9H-purine-2,8-diamine To a stirred solution of tert-butyl 4-(2-(tert-butylamino)-8-((3-chloro-5-(trifluoromethyl)phenyl)amino)-9H-purin-9- yl)piperidine-1-carboxylate (0.3 g, 0.5 mmol) in methanol (10 mL) was added HCl in dioxane (5 mL) at 0° C. The reaction mixture was stirred at ambient temperature for 4 h. Completion of the reaction was confirmed by UPLC. The product was purified by standard methods to afford N2-(tert-butyl)-N8-(3-chloro-5-(trifluoromethyl)phenyl)-9-(piperidin-4-yl)-9H-purine-2,8-diamine (230 mg, 93%). MS (ESI) m/z 468, 469 [M, M+1]+. $^1$H NMR (400 MHz, CD$_3$OD): δ 8.27 (brs, 1H), 8.07 (brs, 1H), 7.89 (brs, 1H), 7.32 (s, 1H), 4.56-4.62 (m, 1H), 3.47 (m, 2H), 2.96-3.06 (m, 2H), 2.87-2.93 (m, 2H), 2.07 (m, 2H), 1.52 (s, 9H).

Example 7. N2-(tert-Butyl)-N8-(3, 4-dichlorophenyl)-9-(piperidin-4-yl)-9H-purine-2,8-diamine

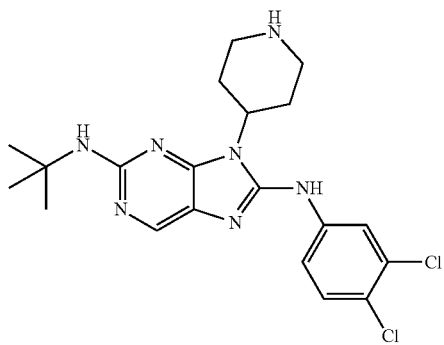 [SMILES: CC(C)(C)Nc1ncc2nc(Nc3ccc(Cl)c(Cl)c3)n(C3CCNCC3)c2n1]

tert-Butyl-4-(2-(tert-butylamino)-8-((3,4-dichlorophenyl)amino)-9H-purin-9-yl)piperidine-1-carboxylate To a stirred solution of tert-butyl-4-((5-amino-2-(tert-butylamino) pyrimidin-4-yl)amino)piperidine-1-carboxylate (0.8 g, 2.2 mmol) and 1,2-dichloro-4-isothiocyanatobenzene (0.5 g, 2.2 mmol) in THF was added EDCI (0.8 g, 4.4 mmol) at ambient temperature. The reaction mixture was heated to 60° C. for 4 h. Completion of the reaction was confirmed by UPLC. The product was triturated with petroleum ether to afford tert-butyl-4-(2-(tert-butylamino)-8-((3,4-dichlorophenyl)amino)-9H-purin-9-yl)piperidine-carboxylate (0.8 g) as brown solid. MS (ESI) m/z 534, 535 [M, M+1]+.

N2-(tert-Butyl)-N8-(3,4-dichlorophenyl)-9-(piperidin-4-yl)-9H-purine-2,8-diamine To a stirred solution tert-butyl-4-(2-(tert-butylamino)-8-((3,4-dichlorophenyl)amino)-9H-purin-9-yl)piperidine-1-carboxylate (0.8 g, 1.5 mmol) in methanol (15 mL) was added HCl in dioxane (8 mL) at 0° C. The reaction mixture was stirred at ambient temperature for 4 h. The product was isolated and purified via standard methods to afford N2-(tert-butyl)-N8-(3,4-dichlorophenyl)-9-(piperidin-4-yl)-9H-purine-2,8-diamine (0.4 g, 60%). MS (ESI) m/z 434, 435 [M, M+1]+. $^1$H NMR (400 MHz, CD$_3$OD): δ 8.20 (s, 1H), 7.91 (s, 1H), 7.45-7.49 (m, 2H), 4.46-4.47 (m, 1H), 3.27-3.33 (m, 2H), 2.76-2.86 (m, 4H), 1.90-1.95 (m, 2H), 1.52 (s, 9H).

Example 8. N2-(4-Methyltetrahydro-2H-pyran-4-yl)-9-(piperidin-4-yl)-N8-(3-(trifluoromethyl) phenyl)-9H-purine-2,8-diamine

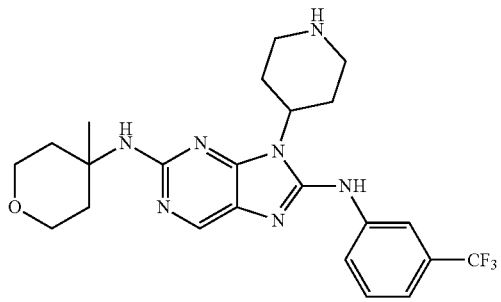 [SMILES: CC1(Nc2ncc3nc(Nc4cccc(C(F)(F)F)c4)n(C4CCNCC4)c3n2)CCOCC1]

tert-Butyl 4-((2-chloro-5-nitropyrimidin-4-yl)amino) piperidine-1-carboxylate

To a stirred solution of 2, 4-dichloro-5-nitropyrimidine (1 g, 5.73 mmol) and DIPEA (3 mL, 17.18 mmol) in IPA (10 mL) was added tertbutyl 4-aminopiperidine-1-carboxylate (1.3 g, 6.30 mmol) portion wise at 0° C. under nitrogen. The reaction mixture was slowly warmed to ambient temperature and stirred for 1 h. Completion of the reaction was confirmed by UPLC. The product was isolated to afford tert-butyl-4-((2-chloro-5-nitropyrimidin-4-yl)amino)piperidine-1-carboxylate (1 g) as yellow solid. MS (ESI) m/z 358, 360 [M, M+2]+.

tert-Butyl 4-((2-((4-methyltetrahydro-2H-pyran-4-yl)amino)-5-nitropyrimidin-4-yl)amino)piperidine-1-carboxylate To a stirred solution of tert-butyl 4-((2-chloro-5-nitropyrimidin-4-yl)amino)piperidine-1-carboxylate (1 g, 2.79 mmol) in DMF (10 mL) was added 4-methyltetrahydro-2H-pyran-4-amine hydrochloride (0.47 g, 3.07 mmol) and sodium bicarbonate (0.47 g, 5.59 mmol) at ambient temperature. The reaction mixture was heated to 60° C. for 4 h. Completion of the reaction was confirmed by UPLC. The product was isolated and triturated with petroleum ether to afford tert-butyl 4-((2-((4-methyltetrahydro-2H-pyran-4-yl)amino)-5-nitropyrimidin-4-yl)amino)piperidine-1-carboxylate (0.6 g, 50%) as pale yellow solid. MS (ESI) m/z 437 [M+1]+.

tert-Butyl-4-((5-amino-2-((4-methyltetrahydro-2H-pyran-4-yl)amino)pyrimidin-4-yl)amino)piperidine-1-carboxylate To a stirred solution of tert-butyl 4-((2-((4-methyl tetrahydro-2H-pyran-4-yl)amino)-5-nitropyrimidin-4-yl)amino) piperidine-1-carboxylate (0.6 g, 1.37 mmol) in ethanol: water (12 mL, 3:1) was added iron powder (0.8 g, 13.75 mmol) and ammonium chloride (0.08 g, 1.51 mmol) at ambient temperature. The reaction mixture was heated to 85° C. for 10 h. Completion of the reaction was confirmed by UPLC. The resulting reaction mixture was filtered through bed of celite, washed with ethyl acetate and concentrated to afford tert-butyl-4-((5-amino-2-((4-methyltetrahydro-2H-pyran-4-yl)amino)pyrimidin-4-yl)amino)piperidine-1-carboxylate (0.4 g, 72%) as a brown solid. MS (ESI) m/z 407 [M+1]+.

tert-Butyl-4-(2-((4-methyltetrahydro-2H-pyran-4-yl) amino)-8-((3-(trifluoromethyl)phenyl)amino)-9H-purin-9-yl)piperidine-1-carboxylate To a stirred solution of tert-butyl 4-((5-amino-2-(tert-butylamino)pyrimidin-4-yl)amino)piperidine-1-carboxylate (0.4 g, 0.98 mmol) and 1-isothiocyanato-3-(trifluoromethyl) benzene (0.22 g, 1.08 mmol) in THF was added EDCI (0.38 g, 1.97 mmol) at ambient temperature. The reaction mixture was heated to 60° C. for 4 h. Completion of the reaction was confirmed by UPLC. The product was isolated and purified via standard methods to afford tert-butyl 4-(2-((4-methyltetrahydro-2H-pyran-4-yl)amino)-8-((3-(trifluoromethyl)phenyl)amino)-9H-purin-9-yl)piperidine-1-carboxylate (0.15 g, 27%) as an off-white solid. MS (ESI) m/z 576, 578 [M, M+2]⁺.

N2-(4-Methyltetrahydro-2H-pyran-4-yl)-9-(piperidin-4-yl)-N8-(3-(trifluoromethyl) phenyl)-9H-purine-2,8-diamine To a stirred solution of tert-butyl 4-(2-((4-methyltetrahydro-2H-pyran-4-yl)amino)-8-((3-(trifluoromethyl)phenyl)amino)-9H-purin-9-yl)piperidine-1-carboxylate (0.15 g, 0.26 mmol) in MeOH (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(4-methyltetrahydro-2H-pyran-4-yl)-9-(piperidin-4-yl)-N8-(3-(trifluoromethyl)phenyl)-9H-purine-2,8-diamine (10 mg, 9%). MS (ESI) m/z 476.2, 477.2 [M,M+1]+. ¹H NMR (400 MHz, CD₃OD): δ 8.24 (s, 1H), 7.97 (s, 1H), 7.87 (d, J=8.4 Hz, 1H), 7.52-7.56 (m, 1H), 7.33 (d, J=7.6 Hz, 1H), 4.50-4.60 (m, 1H), 3.76-3.81 (m, 5H), 3.35-3.40 (m, 1H), 2.80-2.90 (m, 4H), 2.39-2.43 (m, 2H), 1.97-2.01 (m, 2H), 1.74-1.81 (m, 2H), 1.58 (s, 3H).

Example 9. N2-(tert-Butyl)-9-(2-(pyrrolidin-2-yl)ethyl)-N8-(3-(trifluoromethyl)phenyl)-9H-purine-2,8-diamine

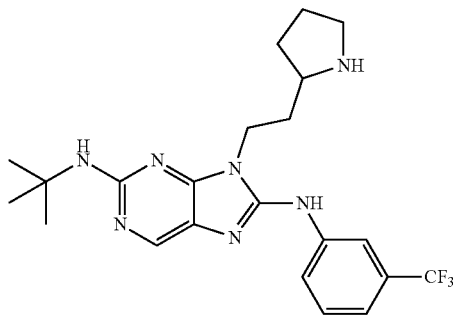 [SMILES: CC(C)(C)Nc1ncc2nc(Nc3cccc(C(F)(F)F)c3)n(CCC3CCCN3)c2n1]

tert-Butyl 2-(2-((2-chloro-5-nitropyrimidin-4-yl)amino)ethyl)pyrrolidine-1-carboxylate To a stirred solution of 2, 4-dichloro-5-nitropyrimidine (0.75 g, 3.9 mmol) and DIPEA (2.1 mL, 11.6 mmol) in IPA (10 mL) was added portionwise tert-butyl 2-(2-aminoethyl) pyrrolidine-1-carboxylate (0.8 g, 3.9 mmol) at 0° C. under nitrogen. The reaction mixture was slowly warmed to ambient temperature and stirred for 1 h. Completion of the reaction was confirmed by UPLC. The product was isolated to afford tert-butyl2-(2-((2-chloro-5-nitropyrimidin-4-yl)amino)ethyl)pyrrolidine-1-carboxylate (1.5 g) as yellow solid. MS (ESI) m/z 372, 373 [M, M+1]⁺.

tert-Butyl 2-(2-((2-(tert-butylamino)-5-nitropyrimidin-4-yl)amino)ethyl)pyrrolidine-1-carboxylate To a stirred solution of tert-butyl 2(2-((2-chloro-5-nitropyrimidin-4-yl)amino) ethyl)pyrrolidine-1-carboxylate (1.5 g, 4 mmol) in DMF (10 mL) was added to tert-butylamine (0.6 g, 8 mmol) and sodium bicarbonate (0.5 g, 6 mmol). The reaction mixture was heated to 60° C. for 4 h. Completion of the reaction was confirmed by UPLC. The product was isolated and purified via standard methods to afford tert-butyl2-(2-((2-(tert-butylamino)-5-nitropyrimidin-4-yl)amino)ethyl)pyrrolidine-1-carboxylate (1 g, 61%) as a pale yellow solid. MS (ESI) m/z 409 [M+1]⁺.

tert-Butyl 2-(2-((5-amino-2-(tert-butylamino)pyrimidin-4-yl)amino)ethyl)pyrrolidine-1-carboxylate To a stirred solution of tert-butyl 2-(2-((2-(tert-butylamino)-5-nitropyrimidin-4-yl)amino)ethyl)pyrrolidine-1-carboxylate (1 g, 2.5 mmol) in ethanol:water (15 mL, 3:1) was added iron powder (1.4 g, 25 mmol) and ammonium chloride (0.13 g, 2.5 mmol) at ambient temperature. The reaction mixture was heated to 85° C. for 2 h. Completion of the reaction was confirmed by UPLC. The resulting reaction mixture was filtered through bed of celite, washed with ethyl acetate and concentrated to afford tert-butyl 2-(2-((5-amino-2-(tert-butylamino) pyrimidin-4-yl)amino) ethyl)pyrrolidine-1-carboxylate (0.8 g, 86%) as a brown solid. MS (ESI) m/z 379 [M+1]⁺.

tert-Butyl 2-(2-(2-(tert-butylamino)-8-((3-(trifluoromethyl)phenyl)amino)-9H-purin-9-yl) ethyl)pyrrolidine-1-carboxylate To a stirred solution of tert-butyl 2-(2-((5-amino-2-(tert-butylamino)pyrimidin-4-yl)amino)ethyl)pyrrolidine-1-carboxylate (0.7 g, 1.9 mmol) and 1-isothiocyanato-3-(trifluoromethyl)benzene (0.4 g, 1.9 mmol) in THF was added EDCI (0.7 g, 3.7 mmol) at ambient temperature. The reaction mixture was heated to 60° C. for 4 h. Completion of the reaction was confirmed by UPLC. The product was isolated and purified via standard methods to afford tert-butyl 2-(2-(2-(tert-butylamino)-8-((3-(trifluoromethyl) phenyl) amino)-9H-purin-9-yl)ethyl)pyrrolidine-1-carboxylate (0.5 g, 49%) as of white solid. MS (ESI) m/z 548 [M+1]⁺.

N2-(tert-Butyl)-9-(2-(pyrrolidin-2-yl)ethyl)-N8-(3-(trifluoromethyl)phenyl)-9H-purine-2,8-diamine To a stirred solution of tert-butyl 2-(2-(2-(tert-butylamino)-8-((3-(trifluoromethyl)phenyl)amino)-9H-purin-9-yl)propyl)carbamate (0.45 g, 0.8 mmol) in methanol (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(tert-butyl)-9-(2-(pyrrolidin-2-yl) ethyl)-N8-(3-(trifluoromethyl) phenyl)-9H-purine-2,8-diamine (345 mg, 96%). MS (ESI) m/z 448 [M+1]⁺. ¹H NMR (400 MHz, CD₃OD): δ 8.19 (s, 1H), 8.00 (s, 1H), 7.88 (d, J=7.6 Hz, 1H), 7.49-7.53 (m, 1H), 7.30 (d, J=7.6 Hz, 1H), 4.23-4.32 (m, 2H), 3.11-3.19 (m, 2H), 2.94-2.98 (m, 1H), 2.17-2.20 (m, 1H), 2.01-2.08 (m, 2H), 1.85-1.95 (m, 2H), 1.53 (s, 10H).

Example 10. N2-(tert-Butyl)-N8-(3,5-dichlorophenyl)-9-(piperidin-4-yl)-9H-purine-2,8-diamine

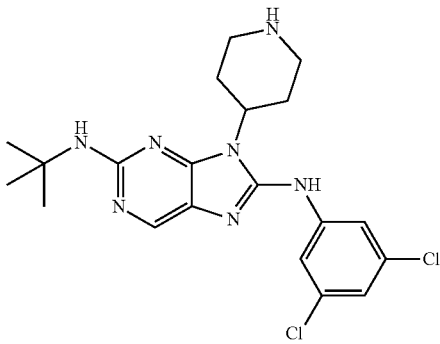 [SMILES: CC(C)(C)Nc1ncc2nc(Nc3cc(Cl)cc(Cl)c3)n(C3CCNCC3)c2n1]

tert-Butyl 4-((2-chloro-5-nitropyrimidin-4-yl)amino) piperidine-1-carboxylate

To a stirred solution of 2, 4-dichloro-5-nitropyrimidine (7.5 g, 39 mmol) and DIPEA (20.6 mL, 116 mmol) in IPA (100 mL) was added tert-butyl 4-aminopiperidine-1-carboxylate (7.73 g, 38.6 mmol) portionwise at 0° C. under nitrogen. The reaction mixture was slowly warmed to ambient temperature and stirred for 1 h. Completion of the reaction was confirmed by UPLC. The product was isolated to afford tert-butyl 4-((2-chloro-5-nitropyrimidin-4-yl) amino)piperidine-1-carboxylate (15 g) as yellow solid. MS (ESI) m/z 358, 359 [M, M+1]+.

tert-Butyl 4-((2-(tert-butylamino)-5-nitropyrimidin-4-yl)amino)piperidine-1 carboxylate To a stirred solution of tert-butyl 4-((2-chloro-5-nitropyrimidin-4-yl)amino)piperidine-1-carboxylate (15 g, 42 mmol) in DMF (80 mL) was added tert-butylamine (6 g, 84 mmol) and sodium bicarbonate (5 g, 63 mmol) at ambient temperature. The reaction mixture was heated at 60° C. for 4 h. Completion of the reaction was confirmed by UPLC. The product was isolated and triturated with petroleum ether to afford tert-butyl 4-((2-(tert-butylamino)-5-nitropyrimidin-4-yl)amino)piperidine-1-carboxylate (14 g, 73%) as yellow solid. MS (ESI) m/z 395 [M+1]+.

tert-Butyl4-((5-amino-2-(tert-butylamino)pyrimidin-4-yl)amino)piperidine-1 carboxylate To a stirred solution of tert-butyl 4-((2-(tert-butylamino)-5-nitropyrimidin-4-yl)amino)piperidine-1-carboxylate (10 g, 25 mmol) in ethanol:water (120 mL, 3:1) was added iron powder (14 g, 253 mmol) and ammonium chloride (1.34 g, 25 mmol) at ambient temperature. The reaction mixture was heated to 85° C. for 10 h. Completion of the reaction was confirmed by UPLC. The resulting reaction mixture was filtered through a bed of celite, washed with ethyl acetate and concentrated to afford tert-butyl 4-((5-amino-2-(tert-butylamino)pyrimidin-4-yl)amino)piperidine-1-carboxylate (9 g, 97%) as a brown solid. MS (ESI) m/z 365 [M+1]+.

tert-Butyl4-(2-(tert-butylamino)-8-((3,5-dichlorophenyl)amino)-9H-purin-9-yl)piperidine-1-carboxylate To a stirred solution of tert-butyl 4-((5-amino-2-(tert-butylamino)pyrimidin-4-yl)amino)piperidine-1-carboxylate (0.6 g, 2 mmol) and 1,3-dichloro-5-isothiocyanatobenzene (0.34 g, 2 mmol) in THF was added EDCI (0.63 g, 3 mmol) at ambient temperature. The reaction mixture was heated to 60° C. for 4 h. Completion of the reaction was confirmed by UPLC. The product was isolated and purified via standard methods to afford tert-butyl 4-(2-(tert-butylamino)-8-((3,5-dichlorophenyl)amino)-9H-purin-9-yl)piperidine-1-carboxylate (0.4 g, 46%) as an off-white solid. MS (ESI) m/z 534, 535 [M, M+1]+.

N2-(tert-Butyl)-N8-(3,5-dichlorophenyl)-9-(piperidin-4-yl)-9H-purine-2,8-diamine To a stirred solution of tert-butyl 4-(2-(tert-butylamino)-8-((3,5-dichlorophenyl)amino)-9H-purin-9-yl)piperidine-1-carboxylate (0.4 g, 0.75 mmol) in MeOH (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(tert-butyl)-N8-(3,5-dichlorophenyl)-9-(piperidin-4-yl)-9H-purine-2,8-diamine (120 mg, 37%). MS (ESI) m/z 434, 435, 436, 437 [M,M+1,M+2, M+3]+. $^1$H NMR (400 MHz, CD$_3$OD): δ 8.24 (brs, 1H), 7.65 (brs, 2H), 7.07-7.08 (m, 1H), 4.46-4.54 (m, 1H), 3.37 (s, 2H), 2.80-2.92 (m, 4H), 1.95-1.98 (m, 2H), 1.52 (s, 9H).

Example 11. N2-(tert-Butyl)-9-(piperidin-4-yl)-N8-(4-(trifluoromethoxy)phenyl)-9H-purine-2,8-diamine

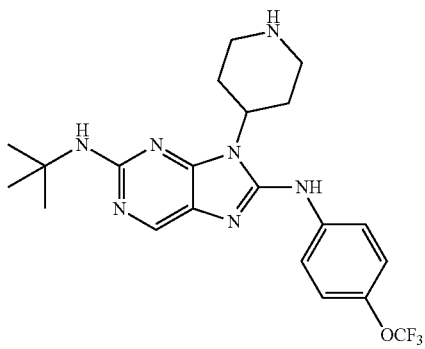 [SMILES: CC(C)(C)Nc1ncc2nc(Nc3ccc(OC(F)(F)F)cc3)n(C3CCNCC3)c2n1]

tert-Butyl 4-(2-(tert-butylamino)-8-((4-(trifluoromethoxy)phenyl)amino)-9H-purin-9-yl) piperidine-1-carboxylate To a stirred solution of tert-butyl 4-((5-amino-2-(tert-butylamino)pyrimidin-4-yl)amino)piperidine-1-carboxylate (0.6 g, 1.6 mmol) and 1-isothiocyanato-4-(trifluoromethoxy)benzene (0.36 g, 1.6 mmol) in THF (10 mL) was added EDCI (0.6 g, 3.3 mmol) ambient temperature. The reaction mixture was heated to 60° C. for 4 h. Completion of reaction was confirmed by TLC. The product was isolated and purified via standard methods to afford tert-butyl 4-(2-(tert-butylamino)-8-((4-(trifluoromethoxy)phenyl)amino)-9H-purin-9-yl)-piperidine-1-carboxylate (0.4 g, 40%) as an off-white solid. MS (ESI) m/z 550 [M+1]+.

N2-(tert-Butyl)-9-(piperidin-4-yl)-N8-(4-(trifluoromethoxy)phenyl)-9H-purine-2,8-diamine To a stirred solution of tert-butyl 4-(2-(tert-butylamino)-8-((4-(trifluoromethoxy)phenyl)amino)-9H-purin-9-yl)piperidine-1-carboxylate (0.4 g, 0.7 mmol) in methanol (10 mL) was added HCl in dioxane (5 mL) at 0° C. The reaction mixture was stirred in at ambient temperature for 16 h. Completion of the reaction was confirmed by UPLC. The product was purified by standard methods to afford N2-(tert-butyl)-9-(piperidin-4-yl)-N8-(4-(trifluoromethoxy)phenyl)-9H-purine-2,8-diamine (260 mg, 80%). MS (ESI) m/z 450 [M+1]+. $^1$H NMR (400 MHz, CD$_3$OD): δ 8.15 (s, 1H), 7.65 (d, J=8.5 Hz, 2H), 7.27 (d, J=8.5 Hz, 2H), 4.47-4.52 (m, 1H), 3.31 (m, 2H), 2.75-2.89 (m, 4H), 1.95 (m, 2H), 1.52 (s, 9H).

Example 12. N2-(tert-Butyl)-9-(piperidin-4-ylmethyl)-N8-(3-(trifluoromethyl)phenyl)-9H-purine-2,8-diamine

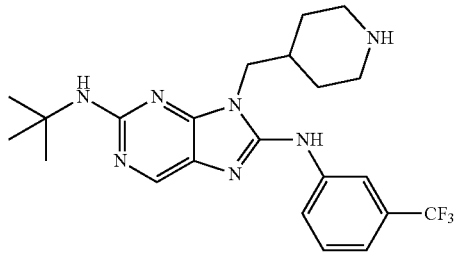 [SMILES: CC(C)(C)Nc1ncc2nc(Nc3cccc(C(F)(F)F)c3)n(CC3CCNCC3)c2n1]

tert-Butyl 4-(((2-chloro-5-nitropyrimidin-4-yl)amino)methyl)piperidine-1-carboxylate To a stirred solution of 2, 4-dichloro-5-nitropyrimidine (0.7 mg, 3.4 mmol) and DIPEA (1.92 mL, 10.80 mmol) in IPA (10 mL) was added tert-butyl-4-(aminomethyl)piperidine-1-carboxylate (770 mg, 3.4 mmol) portionwise at 0° C. under nitrogen. The reaction mixture was slowly warmed to ambient temperature and stirred for 1 h. Completion of the reaction was confirmed by UPLC. The product was isolated to afford tert-butyl 4-(((2-chloro-5-nitropyrimidin-4-yl)amino)methyl)piperidine-1-carboxylate (1.5 g) as yellow solid. MS (ESI) m/z 372 [M+1]+.

tert-Butyl 4-(((2-(tert-butylamino)-5-nitropyrimidin-4-yl)amino)methyl)piperidine-1-carboxylate To a stirred solution of tert-butyl 4-(((2-chloro-5-nitropyrimidin-4-yl)amino)methyl)piperidine-1-carboxylate (1.5 g, 4 mmol) in DMF (15 mL) was added tert-butylamine (0.6 g, 8 mmol) and sodium bicarbonate (0.5 g, 6 mmol) at ambient temperature. The reaction mixture was heated to 60° C. for 4 h. Completion of the reaction was confirmed by UPLC. The product was isolated and purified via standard methods to afford tert-butyl 4-(((2-(tert-butylamino)-5-nitropyrimidin-4-yl)amino)methyl)piperidine-1-carboxylate (1 g, 61%) as yellow solid. MS (ESI) m/z 409 [M+1]+.

tert-Butyl 4-(((5-amino-2-(tert-butylamino)pyrimidin-4-yl)amino)methyl)piperidine-1-carboxylate To a stirred solution of tert-butyl 4-(((2-(tert-butylamino)-5-nitropyrimidin-4-yl) amino)methyl)piperidine-1-carboxylate (1 g, 2.5 mmol) in ethanol:water (15 mL, 3:1) was added iron powder (1.4 g, 25 mmol) and ammonium chloride (0.13 g, 2.5 mmol) at ambient temperature. The reaction mixture was heated to 85° C. for 4 h. Completion of the reaction was confirmed by UPLC. The resulting reaction mixture was filtered through a bed of celite, washed with ethyl acetate and concentrated to afford tert-butyl 4-(((5-amino-2-(tert-butylamino)pyrimidin-4-yl)amino)methyl)piperidine-1-carboxylate (0.8 g, 86%) as a brown solid. MS (ESI) m/z 379 [M+1]+.

tert-Butyl 4-((2-(tert-butylamino)-8-((3-(trifluoromethyl)phenyl)amino)-9H-purin-9-yl)methyl)piperidine-1-carboxylate To a stirred solution of tert-butyl 4-(((5-amino-2-(tert-butylamino)pyrimidin-4-yl)amino)methyl)piperidine-1-carboxylate (0.7 g, 1.9 mmol) and 1-isothiocyanato-3-(trifluoromethyl)benzene (0.4 g, 1.9 mmol) in THF was added EDCI (0.7 g, 3.7 mmol) at ambient temperature. The reaction mixture was heated to 60° C. for 4 h. Completion of the reaction was confirmed by UPLC. The product was isolated and purified via standard methods to afford tert-butyl 4-((2-(tert-butylamino)-8-((3-(trifluoromethyl)phenyl) amino)-9H-purin-9-yl)methyl)piperidine-1-carboxylate (0.4 g, 39%) as an off-white solid. MS (ESI) m/z 548 [M+1]+.

N2-(tert-Butyl)-9-(piperidin-4-ylmethyl)-N8-(3-(trifluoromethyl)phenyl)-9H-purine-2,8-diamine To a stirred solution of tert-butyl 4-((2-(tert-butylamino)-8-((3-(trifluoromethyl) phenyl)amino)-9H-purin-9-yl)methyl)piperidine-1-carboxylate (0.4 g, 0.7 mmol) in methanol (10 mL) was added HCl in dioxane (4 mL) at 0° C. The reaction mixture was stirred at ambient temperature for 4 h. Completion of the reaction was confirmed by UPLC. The product was purified by standard methods to afford N2-(tert-butyl)-9-(piperidin-4-ylmethyl)-N8-(3-(trifluoromethyl) phenyl)-9H-purine-2,8-diamine (0.3 g, 92%). MS (ESI) m/z 448 [M+1]+. $^1$H NMR (400 MHz, CD$_3$OD): δ 8.19 (s, 1H), 8.05 (s, 1H), 7.95 (d, J=8.1 Hz, 1H), 7.53-7.57 (m, 1H), 7.34 (d, J=7.7 Hz, 1H), 4.13 (d, J=7.4 Hz, 2H), 3.13-3.16 (m, 2H), 2.62-2.68 (m, 2H), 2.16-2.23 (m, 1H), 1.72 (m, 2H), 1.52 (s, 9H), 1.40-1.47 (m, 2H).

Example 13. N2-(tert-Butyl)-9-(pyrrolidin-3-ylmethyl)-N8-(3-(trifluoromethyl)phenyl)-9H-purine-2,8-diamine

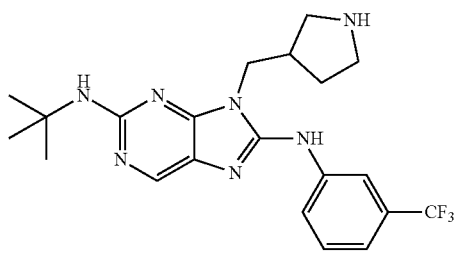 [SMILES: CC(C)(C)Nc1ncc2nc(Nc3cccc(C(F)(F)F)c3)n(CC3CCNC3)c2n1]

tert-Butyl 3-(((2-chloro-5-nitropyrimidin-4-yl)amino)methyl)pyrrolidine-1-carboxylate To a stirred solution of 2, 4-dichloro-5-nitropyrimidine (0.7 g, 3.4 mmol) and DIPEA (1.9 mL, 11 mmol) in IPA (10 mL) was added tert-butyl 3-(amino methyl)pyrrolidine-1-carboxylate (0.72 g, 3.4 mmol) portionwise at 0° C. under nitrogen. The reaction mixture was slowly warmed to ambient temperature and stirred for 1 h. Completion of the reaction was confirmed by UPLC. The product was isolated to afford tert-butyl 3-(((2-chloro-5-nitropyrimidin-4-yl) amino) methyl)pyrrolidine-1-carboxylate (1.4 g) as a yellow solid. MS (ESI) m/z 358, 359 [M, M+1]$^+$.

tert-Butyl 3-(((2-(tert-butylamino)-5-nitropyrimidin-4-yl)amino)methyl)pyrrolidine-1-carboxylate To a stirred solution of tert-butyl 3-(((2-chloro-5-nitropyrimidin-4-yl)amino)methyl)pyrrolidine-1-carboxylate (1.4 g, 3.9 mmol) in DMF (12 mL) was added tert-butylamine (0.6 g, 7.8 mmol) and sodium bicarbonate (0.5 g, 5.9 mmol) at ambient temperature. The reaction mixture was heated to 60° C. for 4 h. Completion of the reaction was confirmed by UPLC. The product was isolated and purified via standard methods to afford tert-butyl 3-(((2-(tert-butylamino)-5-nitropyrimidin-4-yl)amino)methyl)pyrrolidine-1-carboxylate (0.9 g, 58%) as yellow solid. MS (ESI) m/z 395 [M+1]$^+$.

tert-Butyl 3-(((5-amino-2-(tert-butylamino)pyrimidin-4-yl)amino)methyl)pyrrolidine-1-carboxylate To a stirred solution of tert-butyl 3-(((2-(tert-butylamino)-5-nitropyrimidin-4-yl)amino)methyl)pyrrolidine-1-carboxylate (0.9 g, 2.3 mmol) in ethanol:water (12 mL, 3:1) was added iron powder (1.28 g, 23 mmol) and ammonium chloride (0.12 g, 2.3 mmol) at ambient temperature. The reaction mixture was heated to 85° C. for 4 h. Completion of the reaction was confirmed by UPLC. The resulting reaction mixture was filtered through a bed of celite, washed with ethyl acetate and concentrated to tert-butyl 3-(((5-amino-2-(tert-butyl amino)pyrimidin-4-yl)amino)methyl) pyrrolidine-1-carboxylate (0.8 g, 90%) as a brown solid. MS (ESI) m/z 365 [M+1]$^+$.

tert-Butyl 3-((2-(tert-butylamino)-8-((3-(trifluoromethyl)phenyl)amino)-9H-purin-9-yl) methyl)pyrrolidine-1-carboxylate To a stirred solution of tert-butyl 3-(((5-amino-2-(tert-butylamino)pyrimidin-4-yl)amino)methyl)pyrrolidine-1-carboxylate (0.7 g, 1.9 mmol) and 1-isothiocyanato-3-(trifluoromethyl)benzene (0.4 g, 1.9 mmol) in THF was added EDCI (0.73 g, 3.8 mmol) at ambient temperature. The reaction mixture was heated to 60° C. for 4 h. Completion of the reaction was confirmed by UPLC. The product was isolated and purified via standard methods to afford tert-butyl 3-((2-(tert-butylamino)-8-((3-(trifluoromethyl)phenyl) amino)-9H-purin-9-yl)methyl)pyrrolidine-1-carboxylate (0.4 g, 39%) as an off-white solid. MS (ESI) m/z 534 [M+1]$^+$.

N2-(tert-Butyl)-9-(pyrrolidin-3-ylmethyl)-N8-(3-(trifluoromethyl)phenyl)-9H-purine-2,8-diamine To a stirred solution of tert-butyl 3-((2-(tert-butylamino)-8-((3-(trifluoromethyl) phenyl)amino)-9H-purin-9-yl) methyl)pyrrolidine-1-carboxylate (0.4 g, 0.8 mmol) in methanol (10 mL) was added HCl in dioxane (5 mL) at 0° C. The reaction mixture was stirred at ambient temperature for 4 h. Completion of the reaction was confirmed by UPLC. The product purified by standard methods to afford N2-(tert-butyl)-9-(pyrrolidin-3-ylmethyl)-N8-(3-(trifluoromethyl) phenyl)-9H-purine-2,8-diamine (0.31 g, 95%). MS (ESI) m/z 434 [M+1]+. $^1$H NMR (400 MHz, CD$_3$OD): δ 8.20 (s, 1H), 8.08 (s, 1H), 7.96 (d, J=8.1 Hz, 1H), 7.52-7.56 (m, 1H), 7.35 (d, J=7.8 Hz, 1H), 4.22-4.34 (m, 2H), 3.19-3.32 (m, 2H), 3.06-3.13 (m, 1H), 2.86-2.95 (m, 2H), 2.04-2.08 (m, 1H), 1.77-1.85 (m, 1H), 1.51 (s, 9H).

Example 14. N2-(tert-Butyl)-N8-(4-chlorophenyl)-9-(pyrrolidin-3-yl)-9H-purine-2,8-diamine

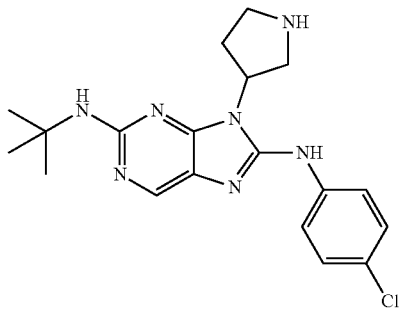 [SMILES: CC(C)(C)Nc1ncc2nc(Nc3ccc(Cl)cc3)n(C3CCNC3)c2n1]

tert-Butyl 3-((2-chloro-5-nitropyrimidin-4-yl)amino) pyrrolidine-1-carboxylate

To a stirred solution of 2, 4-dichloro-5-nitropyrimidine (1.5 g, 7.7 mmol) and DIPEA (2.8 mL, 15.5 mmol) in IPA (25 mL) was added tert-butyl 3-aminopyrrolidine-1-carboxylate (1.4 g, 7.7 mmol) portionwise at 0° C. under nitrogen. The reaction mixture was slowly warmed to ambient temperature and stirred for 1 h. Completion of the reaction was confirmed by UPLC. The product was isolated to afford tert-butyl 3-((2-chloro-5-nitropyrimidin-4-yl) amino)pyrrolidine-1-carboxylate (3.0 g). MS (ESI) m/z 342, 343 [M−1, M]$^+$.

tert-Butyl 3-((2-(tert-butylamino)-5-nitropyrimidin-4-yl)amino)pyrrolidine-1-carboxylate A stirred solution of tert-butyl3-((2-chloro-5-nitropyrimidin-4-yl)amino)pyrrolidine-1-carboxylate (2.8 g, 8.2 mmol), tert-butylamine (1.2 g, 16.3 mmol) and sodium bicarbonate (1.0 g, 12.2 mmol) in DMF (30 mL) was heated to 60° C. for 4 h. Completion of the reaction was confirmed by UPLC. The product was isolated to afford tert-butyl 3-((2-(tert-butylamino)-5-nitropyrimidin-4-yl)amino)pyrrolidine-1-carboxylate (3.0 g) as a pale yellow solid. MS (ESI) m/z 381 [M+1]$^+$.

tert-Butyl 3-((5-amino-2-(tert-butylamino)pyrimidin-4-yl)amino)pyrrolidine-1-carboxylate To a stirred solution of tert-butyl 3-((2-(tert-butylamino)-5-nitropyrimidin-4-yl) amino)pyrrolidine-1-carboxylate (3 g, 7.9 mmol) in ethanol:water (40 mL, 3:1) was added iron powder (4.4 g, 79 mmol) and ammonium chloride (0.48 g, 7.9 mmol) at ambient temperature. The reaction mixture was heated to 85° C. for 2 h. Completion of the reaction was confirmed by UPLC. The resulting reaction mixture was filtered through a bed of celite, washed with ethyl acetate and concentrated to afford tert-butyl3-((5-amino-2-(tert-butylamino)pyrimidin-4-yl)amino)pyrrolidine-1-carboxylate (3.2 g) as a brown solid. MS (ESI) m/z 351 [M+1]$^+$.

tert-Butyl 3-(2-(tert-butylamino)-8-((4-chlorophenyl)amino)-9H-purin-9-yl)pyrrolidine-1-carboxylate To a stirred solution of tert-butyl 3-((5-amino-2-(tert-butylamino)pyrimidin-4-yl)amino)pyrrolidine-1-carboxylate (0.6 g, 1.7 mmol) and 1-chloro-4-isothiocyanatobenzene (0.3 g, 1.7 mmol) in THF (10 mL) was added EDCI (0.65 g, 3.4 mmol) at ambient temperature. The reaction mixture was heated to 60° C. for 4 h. Completion of the reaction was confirmed by UPLC. The product was isolated and triturated with petroleum ether to afford tert-butyl 3-(2-(tert-butylamino)-8-((4-chlorophenyl)amino)-9H-purin-9-yl)pyrrolidine-1-carboxylate (0.5 g) as a brown solid. MS (ESI) m/z 486, 487 [M, M+1]$^+$.

N2-(tert-Butyl)-N8-(4-chlorophenyl)-9-(pyrrolidin-3-yl)-9H-purine-2,8-diamine To a stirred solution of tert-butyl 3-(2-(tert-butylamino)-8-((4-chlorophenyl) amino)-9H-purin-9-yl) pyrrolidine-1-carboxylate (0.5 g, 0.5 mmol) in methanol (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(tert-butyl)-N8-(4-chlorophenyl)-9-(pyrrolidin-3-yl)-9H-purine-2,8-diamine (0.1 g, 25%). MS (ESI) m/z 386, 387 [M, M+1]$^+$. $^1$H NMR (400 MHz, CD$_3$OD): δ 8.12 (s, 1H), 7.64 (d, J=8.8 Hz, 2H), 7.32 (d, J=8.8 Hz, 2H), 5.35 (m, 1H), 3.37-3.49 (m, 2H), 3.20-3.25 (m, 1H), 2.92-2.99 (m, 1H), 2.48-2.55 (m, 1H), 2.05-2.11 (m, 1H), 1.50 (s, 9H).

Example 15. N8-(3-Chloro-2-fluorophenyl)-9-(piperidin-4-yl)-N2-(tetrahydro-2H-pyran-4-yl)-9H-purine-2,8-diamine

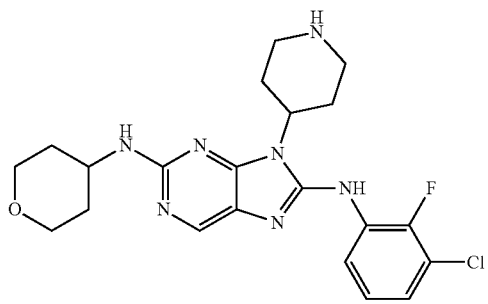 [SMILES: Fc1c(Cl)cccc1Nc1nc2cnc(NC3CCOCC3)nc2n1C1CCNCC1]

tert-Butyl 4-((2-chloro-5-nitropyrimidin-4-yl)amino)piperidine-1-carboxylate To a stirred solution of 2, 4-dichloro-5-nitropyrimidine (1 g, 5.73 mmol) and DIPEA (3 mL, 17.18 mmol) in IPA (10 mL) was added portionwise tert-butyl 4-aminopiperidine-1-carboxylate (1.3 g, 6.30 mmol) at 0° C. under nitrogen. The reaction mixture was slowly warmed to ambient temperature and stirred for 1 h. Completion of the reaction was confirmed by UPLC. The product was isolated to afford tert-butyl 4-((2-chloro-5-nitropyrimidin-4-yl)amino)piperidine-1-carboxylate (1 g) as yellow solid. MS (ESI) m/z 358, 360 [M, M+2]$^+$.

tert-Butyl 4-((5-nitro-2-((tetrahydro-2H-pyran-4-yl)amino)pyrimidin-4-yl)amino)piperidine-1-carboxylate To a stirred solution of tert-butyl 4-((2-chloro-5-nitropyrimidin-4-yl)amino)piperidine-1-carboxylate (1 g, 2.79 mmol) in DMF (10 mL) was added tetrahydro-2H-pyran-4-amine (0.31 g, 3.07 mmol) and sodium bicarbonate (0.47 g, 5.59 mmol) at ambient temperature. The reaction mixture was heated to 60° C. for 4 h. Completion of the reaction was confirmed by UPLC. The product was isolated and triturated with petroleum ether to afford tert-butyl 4-((5-nitro-2-((tetrahydro-2H-pyran-4-yl)amino)pyrimidin-4-yl)amino)piperidine-1-carboxylate (0.6 g, 51%) as pale brown solid. MS (ESI) m/z 443 [M+1]$^+$.

tert-Butyl 4-((5-amino-2-((tetrahydro-2H-pyran-4-yl)amino)pyrimidin-4-yl)amino)piperidine-1-carboxylate To a stirred solution of tert-butyl 4-((5-nitro-2-((tetrahydro-2H-pyran-4-yl)amino)pyrimidin-4-yl)amino)piperidine-1-carboxylate (0.6 g, 1.42 mmol) in ethanol:water (12 mL, 3:1) was added iron powder (0.8 g, 14.20 mmol) and ammonium chloride (0.08 g, 1.56 mmol) at ambient temperature. The reaction mixture was heated to 85° C. for 10 h. Completion of the reaction was confirmed by UPLC. The resulting reaction mixture was filtered through bed of celite, washed with ethyl acetate and concentrated to afford tert butyl 4-((5-amino-2-((tetrahydro-2H-pyran-4-yl)amino)pyrimidin-4-yl)amino)piperidine-1-carboxylate (0.4 g, 73%) as a brown solid. MS (ESI) m/z 394 [M+1]$^+$.

tert-Butyl 4-(8-((3-chloro-2-fluorophenyl)amino)-2-((tetrahydro-2H-pyran-4-yl)amino)-9H-purin-9-yl)piperidine-1-carboxylate To a stirred solution of tert-butyl 4-((5-amino-2-((tetrahydro-2H-pyran-4-yl)amino)pyrimidin-4-yl)amino)piperidine-1-carboxylate (0.4 g, 1.02 mmol) and 1-chloro-2-fluoro-3-isothiocyanatobenzene (0.21 g, 1.12 mmol) in THF was added EDCI (0.39 g, 2.04 mmol) at ambient temperature. The reaction mixture was heated to 60° C. for 4 h. Completion of the reaction was confirmed by UPLC. The product was isolated and purified via standard methods to afford tert-butyl 4-(8-((3-chloro-2-fluorophenyl) amino)-2-((tetrahydro-2H-pyran-4-yl)amino)-9H-purin-9-yl)piperidine-1-carboxylate (0.2 g, 36%) as an off-white solid. MS (ESI) m/z 546, 547 [M, M+1]$^+$.

N8-(3-Chloro-2-fluorophenyl)-9-(piperidin-4-yl)-N2-(tetrahydro-2H-pyran-4-yl)-9H-purine-2,8-diamine To a stirred solution of tert-butyl 4-(8-((3-chloro-2-fluorophenyl)amino)-2-((tetrahydro-2H-pyran-4-yl)amino)-9H-purin-9-yl)piperidine-1-carboxylate (0.2 g, 0.37 mmol) in MeOH (10 mL) was added HCl in dioxane (5 mL) at 0° C. The reaction mixture was stirred at ambient temperature for 4 h. Completion of the reaction was confirmed by UPLC. The product was isolated and purified via standard methods to afford N8-(3-chloro-2-fluorophenyl)-9-(piperidin-4-yl)-N2-(tetrahydro-2H-pyran-4-yl)-9H-purine-2,8-diamine (70 mg, 43%). MS (ESI) m/z 446, 447 [M,M+1]+. $^1$H NMR (400 MHz, CD$_3$OD): δ 8.58, 8.05 (brs, 1H), 7.44 (brs, 1H), 7.22-7.24 (m, 1H), 7.14-7.18 (m, 1H), 4.61 (brs, 1H), 3.98-4.08 (m, 3H), 3.60-3.65 (m, 2H), 3.46-3.49 (m, 2H), 2.90-3.02 (m, 4H), 2.01-2.08 (m, 4H), 1.55-1.65 (m, 2H).

Example 16. N2-(tert-Butyl)-N8-(3-(difluoromethyl)phenyl)-9-(piperidin-4-yl)-9H-purine-2,8-diamine

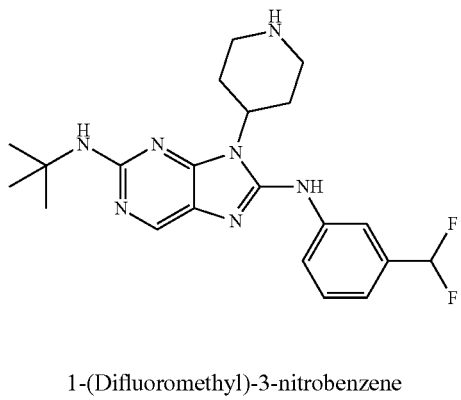

1-(Difluoromethyl)-3-nitrobenzene

To a stirred solution of 3-nitrobenzaldehyde (1.0 g, 7 mmol) dichloromethane (30 mL) was added DAST (2.5 mL, 13 mmol) dropwise at −78 OC. The mixture was stirred for 15 min and then allowed to warm to ambient temperature and stirred for 16 h. Completion of the reaction was monitored by TLC. The product was isolated and purified via standard methods to afford 1-(difluoromethyl)-3-nitrobenzene (0.95 g, 83%) as a brown gummy solid.

3-(Difluoromethyl) aniline

To a stirred solution of 1-(difluoromethyl)-3-nitrobenzene (0.9 g, 5 mmol) in ethanol:water (15:3 mL) was added iron powder (3.0 g, 52 mmol) and ammoniumchloride (0.3 g, 5 mmol) at ambient temperature. The reaction mixture was refluxed at 80° C. for 4 h. Completion of the reaction was confirmed by TLC. The reaction mixture was filtered through bed of celite and the filtrate was concentrated under vacuum to afford 3-(difluoromethyl) aniline (0.85 g) as brown gummy solid. MS (ESI) m/z 144 [M+1]$^+$.

1-(Difluoromethyl)-3-isothiocyanatobenzene

To a stirred solution of 3-(difluoromethyl) aniline (0.85 g, 6 mmol) in DCM (30 mL) was added triethylamine (1.2 g, 12 mmol) and cesium chloride (1 g, 9 mmol) at 0° C. under $N_2$. The reaction mixture was slowly warmed to ambient temperature and stirred for 1 h. Completion of the reaction was confirmed by UPLC. The product was isolated and purified via standard methods to afford 1-(difluoromethyl)-3-isothiocyanatobenzene (0.42 g, 39%) as brown liquid. $^1$H NMR (400 MHz, CDCl$_3$): δ7.33-7.49 (m, 3H), 7.27 (s, 1H), 6.50-6.78 (m, 1H).

tert-Butyl 4-(2-(tert-butylamino)-8-((3-(difluoromethyl)phenyl)amino)-9H-purin-9-yl) piperidine-1-carboxylate To a stirred solution of tert-butyl 4-((5-amino-2-(tert-butylamino)pyrimidin-4-yl)amino)piperidine-1-carboxylate (0.4 g, 1.1 mmol) and 1-(difluoromethyl)-3-isothiocyanatobenzene (0.2 g, 1.1 mmol) in THF was added EDCI (0.42 g, 2.2 mmol) at ambient temperature. The reaction mixture was heated to 60° C. for 4 h. Completion of the reaction was confirmed by TLC. The product was isolated and purified via standard methods to afford tert-butyl 4-(2-(tert-butylamino)-8-((3-(difluoromethyl)phenyl)amino)-9H-purin-9-yl)piperidine-1-carboxylate (0.18 g; 32%) as an pale yellow solid. MS (ESI) m/z 516, 517 [M+1, M+2]$^+$.

N2-(tert-Butyl)-N8-(3-(difluoromethyl) phenyl)-9-(piperidin-4-yl)-9H-purine-2,8-diamine To a stirred solution of tert-butyl 4-(2-(tert-butylamino)-8-((3-(difluoromethyl) phenyl) amino)-9H-purin-9-yl) piperidine-1-carboxylate (0.17 g, 0.3 mmol) in methanol (5 mL) was added HCl in dioxane (2 mL) at 0° C. and slowly brought to ambient temperature. Completion of the reaction was monitored by UPLC. The product was purified by standard methods to afford N2-(tert-Butyl)-N8-(3-(difluoromethyl)phenyl)-9-(piperidin-4-yl)-9H-purine-2, 8-diamine (110 mg, 52%). $^1$H NMR (400 MHz, DMSO-d$_6$): δ 8.54 (d, J=5.2 Hz, 1H), 8.26 (d, J=8.0 Hz, 2H), 7.83 (d, J=8.0 Hz, 2H), 7.54-7.57 (m, 2H), 7.49 (d, J=8.8 Hz, 2H), 7.40 (d, J=5.2 Hz, 1H), 4.74 (d, J=3.6 Hz, 1H), 3.60-3.68 (m, 5H), 3.50-3.55 (m, 1H), 3.36 (d, J=11.2 Hz, 1H), 1.94-2.01 (m, 1H), 1.81-1.86 (m, 1H).

Example 17. N2-(tert-Butyl)-N8-(3,5-difluorophenyl)-9-(piperidin-4-yl)-9H-purine-2,8-diamine

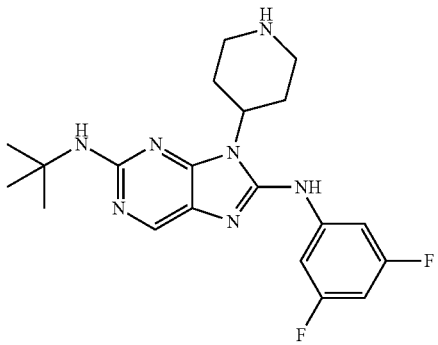 [SMILES: CC(C)(C)Nc1ncc2nc(Nc3cc(F)cc(F)c3)n(C3CCNCC3)c2n1]

tert-Butyl4-(2-(tert-butylamino)-8-((3,5-difluorophenyl)amino)-9H-purin-9-yl)piperidine-1-carboxylate To a stirred solution of tert-butyl 4-((5-amino-2-(tert-butylamino)pyrimidin-4-yl)amino)piperidine-1-carboxylate (0.7 g, 2 mmol) and 1,3-difluoro-5-isothiocyanatobenzene (0.3 g, 2 mmol) in THF (10 mL) was added EDCI (0.7 g, 4 mmol) at ambient temperature. The reaction mixture was heated to 60° C. for 4 h. Completion of the reaction was confirmed by UPLC. The product was isolated and purified via standard methods to afford tert-butyl 4-(2-(tert-butylamino)-8-((3,5-difluorophenyl)amino)-9H-purin-9-yl)piperidine-1 carboxylate (0.35 g, 36%) as an off-white solid. MS (ESI) m/z 502 [M+1]$^+$.

N2-(tert-Butyl)-N8-(3,5-difluorophenyl)-9-(piperidin-4-yl)-9H-purine-2,8-diamine To a stirred solution of tert-butyl 4-(2-(tert-butylamino)-8-((3,5-difluorophenyl)amino)-9H-purin-9-yl)piperidine-1-carboxylate (0.35 g, 0.7 mmol) in methanol (10 mL) was added HCl in dioxane (5 mL) at 0° C. The reaction mixture was stirred at ambient temperature for 16 h. Completion of the reaction was confirmed by UPLC. The product was purified by standard methods to afford N2-(tert-butyl)-N8-

(3,5-difluorophenyl)-9-(piperidin-4-yl)-9H-purine-2,8-diamine (250 mg, 89%). MS (ESI) m/z 402 [M+1]+. ¹H NMR (400 MHz, CD₃OD): δ 8.22 (s, 1H), 7.30 (s, 1H), 7.26 (s, 1H), 6.54-6.60 (m, 1H), 4.44-4.51 (m, 1H), 3.31-3.32 (m, 2H), 2.74-2.88 (m, 4H), 1.91-1.94 (m, 2H), 1.51 (s, 9H).

Example 18. N2-(tert-Butyl)-9-(piperidin-4-yl)-N8-(3-(trifluoromethoxy)phenyl)-9H-purine-2,8-diamine

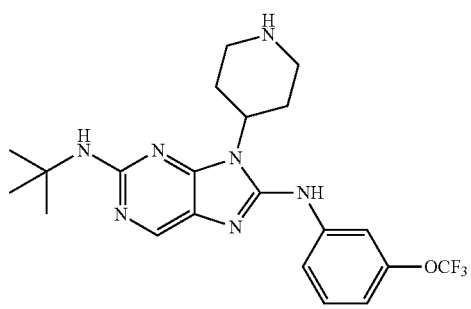 [SMILES: CC(C)(C)Nc1ncc2nc(Nc3cccc(OC(F)(F)F)c3)n(C3CCNCC3)c2n1]

tert-Butyl 4-(2-(tert-butylamino)-8-((3-(trifluoromethoxy)phenyl)amino)-9H-purin-9-yl) piperidine-1-carboxylate To a stirred solution of tert-butyl 4-((5-amino-2-(tert-butyl amino)pyrimidin-4-yl)amino)piperidine-1-carboxylate (0.6 g, 1.6 mmol) and 1-isothiocyanato-3-(trifluoromethoxy)benzene (0.36 g, 1.6 mmol) in THF (10 mL) was added EDCI (0.63 g, 3.3 mmol) at ambient temperature. The reaction mixture was heated to 60° C. for 4 h. Completion of the reaction was confirmed by UPLC. The product was isolated and purified via standard methods to afford tert-butyl 4-(2-(tert-butylamino)-8-((3-(trifluoromethoxy)phenyl)amino)-9H-purin-9-yl)piperidine-1-carboxylate (0.4 g, 40%) as an off-white solid. MS (ESI) m/z 550 [M+1]⁺.

N2-(tert-Butyl)-9-(piperidin-4-yl)-N8-(3-(trifluoromethoxy)phenyl)-9H-purine-2,8-diamine To a stirred solution of tert-butyl 4-(2-(tert-butylamino)-8-((3-(trifluoromethoxy)phenyl)amino)-9H-purin-9-yl)piperidine-1-carboxylate (0.4 g, 0.7 mmol) in methanol (10 mL) was added HCl in dioxane (5 mL) at 0° C. The reaction mixture was stirred at ambient temperature for 16 h. Completion of the reaction was confirmed by UPLC. The product was purified by standard methods to afford N2-(tert-butyl)-9-(piperidin-4-yl)-N8-(3-(trifluoromethoxy)phenyl)-9H-purine-2,8-diamine (280 mg, 86%). MS (ESI) m/z 450 [M+1]+. ¹H NMR (400 MHz, CD₃OD): δ 8.21 (brs, 1H), 7.63 (brs, 1H), 7.58 (d, J=8.0 Hz, 1H), 7.40-7.42 (m, 1H), 6.95 (d, J=8.0 Hz, 1H), 4.50-4.56 (m, 1H), 3.38 (d, 2H), 2.83-2.96 (m, 4H), 1.99-2.02 (m, 2H), 1.52 (s, 9H).

Example 19. N2-(tert-Butyl)-9-(piperidin-4-yl)-N8-(3-(trifluoromethyl) phenyl)-9H-purine-2,8-diamine

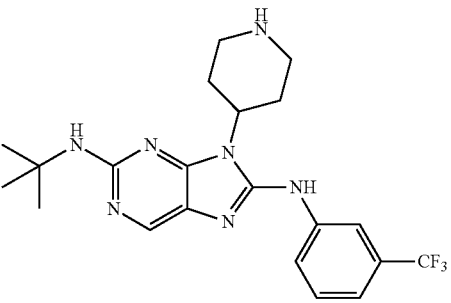 [SMILES: CC(C)(C)Nc1ncc2nc(Nc3cccc(C(F)(F)F)c3)n(C3CCNCC3)c2n1]

tert-Butyl 4-((2-chloro-5-nitropyrimidin-4-yl)amino)piperidine-1-carboxylate

To a stirred solution of 2, 4-dichloro-5-nitropyrimidine (1 g, 5.73 mmol) and DIPEA (3 mL, 17.18 mmol) in IPA (10 mL) was added portionwise tert-butyl 4-aminopiperidine-1-carboxylate (1.3 g, 6.30 mmol) at 0° C. under nitrogen. The reaction mixture was slowly warmed to ambient temperature and stirred for 1 h. Completion of the reaction was confirmed by UPLC. The product was isolated to afford tert-butyl-4-((2-chloro-5-nitropyrimidin-4-yl)amino)piperidine-1-carboxylate (1 g) as yellow solid. MS (ESI) m/z 358, 360 [M, M+2]⁺.

tert-Butyl4-((2-(tert-butylamino)-5-nitropyrimidin-4-yl)amino)piperidine-1carboxylate To a stirred solution of tert-butyl-4-((2-chloro-5-nitropyrimidin-4-yl)amino)piperidine-1-carboxylate (1 g, 2.79 mmol) in DMF (10 mL) was added tert-butylamine (0.22 g, 3.07 mmol) and sodium bicarbonate (0.47 g, 5.59 mmol) at ambient temperature. The reaction mixture was heated to 60° C. for 4 h. Completion of the reaction was confirmed by UPLC. The product was isolated and triturated with petroleum ether to afford tert-butyl 4-((2-(tert-butylamino)-5-nitropyrimidin-4-yl)amino)piperidine-1-carboxylate (0.7 g, 64%) as yellow solid. MS (ESI) m/z 395 [M+1]⁺.

tert-Butyl-4-((5-amino-2-(tert-butylamino)pyrimidin-4-yl)amino)piperidine-1-carboxylate To a stirred solution of tert-butyl-4-((2-(tert-butylamino)-5-nitropyrimidin-4-yl)amino)piperidine-1-carboxylate (0.7 g, 1.77 mmol) in ethanol:water (12 mL, 3:1) was added iron powder (1 g, 18 mmol) and ammonium chloride (0.1 g, 1.8 mmol) at ambient temperature. The reaction mixture was heated to 85° C. for 10 h. Completion of the reaction was confirmed by UPLC. The resulting reaction mixture was filtered through bed of celite, washed with ethyl acetate and concentrated to afford tert-butyl-4-((5-amino-2-(tert-butylamino)pyrimidin-4-yl)amino)piperidine-1-carboxylate (0.5 g, 83%) as a brown solid. MS (ESI) m/z 365 [M+1]⁺.

tert-Butyl-4-(2-(tert-butylamino)-8-((3-(trifluoromethyl)phenyl)amino)-9H-purin-9-yl)piperidine-1-carboxylate. To a stirred solution of tert-butyl 4-((5-amino-2-(tert-butylamino)pyrimidin-4-yl)amino)piperidine-1-carboxylate (0.5 g, 1.37 mmol) and 1-isothiocyanato-3-(trifluoromethyl)benzene (0.31 g, 1.50 mmol) in tetrahydrofuran was added EDCI (0.53 g, 2.74 mmol) at ambient temperature. The reaction mixture was heated to 60° C. for 4 h. Completion of the reaction was confirmed by UPLC. The product was isolated and purified via standard methods to afford tert-butyl 4-(2-(tert-butylamino)-8-((3-(trifluoromethyl)phenyl) amino)-9H-purin-9-yl)piperidine-1-carboxylate (0.25 g; 34%) as an off-white solid. MS (ESI) m/z 534, 536 [M, M+2]$^+$.

N2-(tert-Butyl)-9-(piperidin-4-yl)-N8-(3-(trifluoromethyl)phenyl)-9H-purine-2,8-diamine To a stirred solution of tert-butyl-4-(2-(tert-butylamino)-8-((3-(trifluoromethyl)phenyl) amino)-9H-purin-9-yl)piperidine-1-carboxylate (0.25 g, 0.46 mmol) in MeOH (10 mL) was added HCl in dioxane (5 mL) at 0° C. The reaction mixture was stirred at ambient temperature for 4 h. Completion of the reaction was confirmed by UPLC. The product was isolated and purified via standard methods to afford N2-(tert-butyl)-9-(piperidin-4-yl)-N8-(3-(trifluoromethyl) phenyl)-9H-purine-2,8-diamine (55 mg, 37%). MS (ESI) m/z 434.2, 435.2 [M,M+1]+. $^1$H NMR (400 MHz, CD$_3$OD): δ 8.54, 8.23 (s, 1H), 7.95 (s, 1H), 7.86 (brs, 1H), 7.51-7.56 (m, 1H), 7.34 (d, J=7.6 Hz, 1H), 4.59 (brs, 1H), 3.36-3.56 (m, 2H), 3.01-3.14 (m, 2H), 2.91-2.97 (m, 2H), 2.11-2.14 (m, 2H), 1.51 (s, 9H).

Example 20. N2-(tert-Butyl)-N8-(3-chloro-2-fluorophenyl)-9-(piperidin-4-yl)-9H-purine-2, 8-diamine

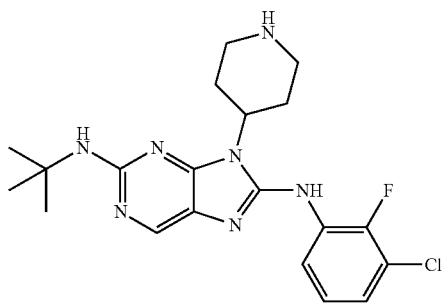 [SMILES: CC(C)(C)Nc1ncc2nc(Nc3cccc(Cl)c3F)n(C3CCNCC3)c2n1]

tert-Butyl 4-((2-chloro-5-nitropyrimidin-4-yl)amino) piperidine-1-carboxylate

To a stirred solution of 2, 4-dichloro-5-nitropyrimidine (4.0 g, 21 mmol) and DIPEA (6 mL, 41 mmol) in IPA (50 mL) was added tert-butyl 4-aminopiperidine-1-carboxylate (4.5 g, 22 mmol) portionwise at 0° C. under nitrogen. The reaction mixture was slowly warmed to ambient temperature and stirred for 5 h. Completion of the reaction was confirmed by UPLC. The product was isolated to afford tert-butyl(4-((2-chloro-5-nitropyrimidin-4-yl)amino)piperidine-1-carboxylate (6.5 g, 82%) as yellow solid. MS (ESI) m/z 358.2 [M+1]$^+$.

tert-Butyl4-((2-(tert-butylamino)-5-nitropyrimidin-4-yl)amino)piperidine-1-carboxylate To a stirred solution of tert-butyl 4-((2-chloro-5-nitropyrimidin-4-yl)amino)piperidine-1-carboxylate (2 g, 6 mmol) in DMF (20 mL) was added 2-methylpropan-2-amine (0.45 g, 6 mmol) and sodium carbonate (1.8 g, 16 mmol) at ambient temperature. The reaction mixture was stirred for 16 h. Completion of the reaction was confirmed by UPLC. The product was isolated via standard method and triturated with petroleum ether to afford tert-butyl4-((2-(tert-butylamino)-5-nitropyrimidin-4-yl)amino)piperidine-1-carboxylate (1.5 g, 68%) as yellow solid. MS (ESI) m/z 395.2 [M+1]$^+$.

tert-Butyl4-((5-amino-2-(tert-butylamino)pyrimidin-4-yl)amino)piperidine-1-carboxylate To a stirred solution of tert-butyl 4-((2-(tert-butylamino)-5-nitropyrimidin-4-yl)amino)piperidine-1-carboxylate (1.3 g, 3 mmol) in ethanol:water (50 mL, 3:1) was added iron powder (1.85 g, 33 mmol) and ammonium chloride (0.18 g, 3 mmol) at ambient temperature. The reaction mixture was heated to 85° C. for 5 h. Completion of the reaction was confirmed by UPLC. The resulting reaction mixture was filtered through a bed of celite, washed with ethyl acetate and concentrated to afford tert-butyl 4-((5-amino-2-(tert-butylamino)pyrimidin-4-yl)amino)piperidine-1-carboxylate (1.0 g) as a brown solid. MS (ESI) m/z 365.4 [M+1]$^+$.

tert-Butyl4-(2-(tert-butylamino)-8-((3-chloro-2-fluorophenyl)amino)-9H-purin-9-yl)piperidine-1-carboxylate To a stirred solution of tert-butyl 4-((5-amino-2-(tert-butylamino)pyrimidin-4-yl)amino)piperidine-1-carboxylate (1 g, 3 mmol) and 1-chloro-2-fluoro-3-isothiocyanatobenzene (0.57 g, 3 mmol) in THF (15 mL) was added EDCI (1 g, 5 mmol) at ambient temperature. The reaction mixture was heated to 50° C. for 6 h. Completion of the reaction was confirmed by UPLC. The product was isolated and purified via standard methods to afford tert-butyl4-(2-(tert-butylamino)-8-((3-chloro-2-fluorophenyl)amino)-9H-purin-9-yl) piperidine-1-carboxylate (0.3 g, 22%) as an off-white solid. MS (ESI) m/z 517, 518 [M, M+1]$^+$.

N2-(tert-Butyl)-N8-(3-chloro-2-fluorophenyl)-9-(piperidin-4-yl)-9H-purine-2,8-diamine To a stirred solution of tert-butyl-4-(2-(tert-butylamino)-8-((3-chloro-2-fluorophenyl)amino)-9H-purin-9-yl)piperidine-1-carboxylate (0.3 g, 0.6 mmol) in DCM (10 mL) was added HCl in dioxane (2 mL) at 0° C. The reaction mixture was stirred at ambient temperature for 2 h. Completion of the reaction was confirmed by UPLC. The product was isolated and purified via standard methods to afford N2-(tert-butyl)-N8-(3-chloro-2-fluorophenyl)-9-(piperidin-4-yl)-9H-purine-2,8-diamine (80 mg, 38%). MS (ESI) m/z 418.2, 419.2 [M, M+1]+. $^1$H NMR (400 MHz, CD$_3$OD): δ 8.19 (brs, 1H), 7.55 (brs, 1H), 7.15-7.23 (m, 2H), 4.63-4.75 (m, 1H), 3.63 (d, J=12.8 Hz, 2H), 3.18-3.25 (m, 2H), 2.96-3.07 (m, 2H), 2.21-2.23 (m, 2H), 1.48 (s, 9H).

Example 21. N8-(3-Chloro-5-(trifluoromethyl)phenyl)-N2-(1-methylcyclobutyl)-9-(piperidin-4-yl)-9H-purine-2,8-diamine

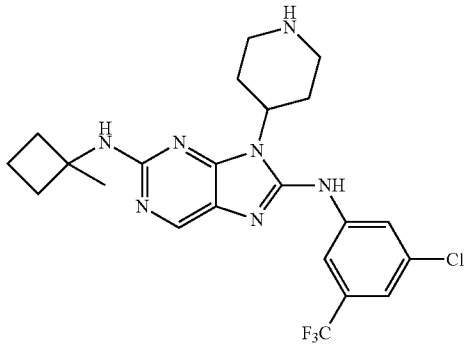 [SMILES: CC1(Nc2ncc3nc(Nc4cc(Cl)cc(C(F)(F)F)c4)n(C4CCNCC4)c3n2)CCC1]

tert-Butyl 4-((2-chloro-5-nitropyrimidin-4-yl)amino)piperidine-1-carboxylate To a stirred solution of 2, 4-dichloro-5-nitropyrimidine (2.00 g, 10 mmol) and DIPEA (3.70 mL, 20 mmol) in IPA (30 mL) was added tert-butyl 4-aminopiperidine-1-carboxylate (2.10 g, 10 mmol) portionwise at 0° C. under nitrogen. The reaction mixture was slowly warmed to ambient temperature and stirred for 1 h. Completion of the reaction was confirmed by UPLC. The product was isolated to afford tert-butyl 4-((2-chloro-5-nitropyrimidin-4-yl)amino)piperidine-1-carboxylate (3.40 g) as pale yellow solid. MS (ESI) m/z 358, 359[M, M+1]+.

tert-Butyl 4-((2-((1-methylcyclobutyl)amino)-5-nitropyrimidin-4-yl)amino)piperidine-1-carboxylate To a stirred solution of tert-butyl 4-((2-chloro-5-nitropyrimidin-4-yl)amino) piperidine-1-carboxylate (0.80 g, 2.24 mmol) in DMF (8 mL) was added 1-methylcyclobutan-1-amine (0.23 g, 2.68 mmol) and sodium carbonate (0.48 g, 4.50 mmol) at ambient temperature. The reaction mixture was stirred at same temperature for 4 h. Completion of the reaction was confirmed by UPLC. The product was isolated and purified via standard methods to afford tert-butyl 4-((2-((1-methylcyclobutyl)amino)-5-nitropyrimidin-4-yl)amino)piperidine-1-carboxy late. (0.55 g, 61%) as an off white solid. MS (ESI) m/z 407[M+1]+.

tert-Butyl 4-((5-amino-2-((1-methylcyclobutyl)amino)pyrimidin-4-yl)amino)piperidine-1-carboxylate To a stirred solution of tert-butyl 4-((2-((1-methylcyclobutyl)amino)-5-nitropyrimidin-4-yl)amino)piperidine-1-carboxy late (0.55 g, 1.35 mmol) in ethanol and water (10 mL, 3:1) was added iron powder (0.76 g, 14 mmol) and ammonium chloride (0.07 g, 1.35 mmol) at ambient temperature. The reaction mixture was heated to 85° C. for 4 h. Completion of the reaction was confirmed by UPLC. The resulting reaction mixture was filtered through a bed of celite, washed with ethyl acetate and concentrated to afford tert-butyl 4-((5-amino-2-((1-methylcyclobutyl)amino)pyrimidin-4-yl)amino)piperidine-1-carboxylate (0.50 g) as a brown solid. MS (ESI) m/z 377[M+1]+ tert-Butyl 4-(8-((3-chloro-5-(trifluoromethyl)phenyl)amino)-2-((1-methylcyclobutyl) amino)-9H-purin-9-yl)piperidine-1-carboxylate To a stirred solution of tert-butyl 4-((5-amino-2-((1-methylcyclobutyl)amino)pyrimidin-4-yl)amino)piperidine-1-carboxylate (0.45 g, 1.20 mmol) and 1-chloro-3-isothiocyanato-5-(trifluoromethyl)benzene (0.28 g, 1.20 mmol) in THF was added EDCI (0.45 g, 2.40 mmol) at ambient temperature. The reaction mixture was heated to 60° C. for 4 h. Completion of the reaction was confirmed by UPLC. The product was isolated and purified via standard methods to afford tert-butyl 4-(8-((3-chloro-5-(trifluoromethyl)phenyl)amino)-2-((1-methylcyclobutyl)amino)-9H-purin-9-yl)piperidine-1-carboxylate (0.21 g, 30%) as an off white solid. MS (ESI) m/z 580, 581[M, M+1]+.

N8-(3-Chloro-5-(trifluoromethyl)phenyl)-N2-(1-methylcyclobutyl)-9-(piperidin-4-yl)-9H-purine-2,8-diamine To a stirred solution of tert-butyl 4-(8-((3-chloro-5-(trifluoromethyl)phenyl)amino)-2-((1-methylcyclobutyl) amino)-9H-purin-9-yl)piperidine-1-carboxylate (0.20 g, 0.34 mmol) in MeOH (5 mL) was added HCl in dioxane (2 mL) at 0° C. The reaction mixture was stirred at ambient temperature for 4 h. Completion of the reaction was confirmed by UPLC. The product was isolated and purified via standard methods to afford N8-(3-chloro-5-(trifluoromethyl)phenyl)-N2-(1-methylcyclobutyl)-9-(piperidin-4-yl)-9H-purine-2, 8-diamine (0.16 g, 97%) as an off white solid. MS (ESI) m/z 480.2, 481.2[M, M+1]+; $^1$H NMR (400 MHz, CD$_3$OD) δ 8.24 (brs, 1H), 8.05 (brs, 1H), 7.87 (brs, 1H), 7.29 (s, 1H), 4.56-4.62 (m, 1H), 3.51-3.54 (m, 2H), 3.05-3.12 (m, 2H), 2.89-2.98 (m, 2H), 2.31-2.39 (m, 2H), 2.17-2.23 (m, 2H), 2.07-2.10 (m, 2H), 1.89-1.97 (m, 2H), 1.60 (s, 3H).

Example 22. N8-(3,5-Bis(trifluoromethyl)phenyl)-N2-(tert-butyl)-9-(piperidin-4-yl)-9H-purine-2,8-diamine

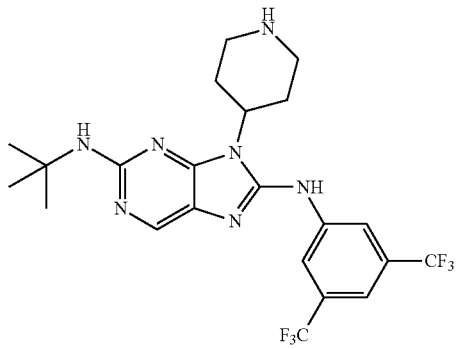 [SMILES: CC(C)(C)Nc1ncc2nc(Nc3cc(C(F)(F)F)cc(C(F)(F)F)c3)n(C3CCNCC3)c2n1]

tert-Butyl 4-((2-chloro-5-nitropyrimidin-4-yl)amino)piperidine-1-carboxylate To a stirred solution of 2, 4-dichloro-5-nitropyrimidine (3.0 g, 15 mmol) and DIPEA (6.9 mL, 39 mmol) in IPA (40 mL) was added tert-butyl 4-aminopiperidine-1-carboxylate (3.1 g, 15 mmol) portionwise at 0° C. under nitrogen. The reaction mixture was slowly warmed to ambient temperature and stirred for 1 h. Completion of the reaction was confirmed by UPLC. The product was isolated to afford tert-butyl 4-((2-chloro-5-nitropyrimidin-4-yl)amino)piperidine-1-carboxylate (3.4 g) as yellow solid. MS (ESI) m/z 358, 359[M, M+1]⁺.

tert-Butyl 4-((2-(tert-butylamino)-5-nitropyrimidin-4-yl)amino)piperidine-1 carboxylate To a stirred solution of tert-butyl 4-((2-chloro-5-nitropyrimidin-4-yl)amino)piperidine-1-carboxylate (2.5 g, 7 mmol) in DMF (30 mL) was added tert-butylamine (1 g, 14 mmol) and sodium bicarbonate (0.9 g, 10.4 mmol) at ambient temperature. The reaction mixture was heated at 60° C. for 4 h. Completion of the reaction was confirmed by UPLC. The product was isolated and purified via standard methods to afford tert-butyl 4-((2-(tert-butylamino)-5-nitropyrimidin-4-yl)amino)piperidine-1-carboxylate (2.1 g, 76%) as yellow solid. MS (ESI) m/z 395[M+1]⁺.

tert-Butyl 4-((5-amino-2-(tert-butylamino)pyrimidin-4-yl)amino)piperidine-1carboxylate To a stirred solution of tert-butyl 4-((2-(tert-butylamino)-5-nitropyrimidin-4-yl)amino) piperidine-1-carboxylate (2.1 g, 5.30 mmol) in ethanol and water (40 mL, 3:1) was added iron powder (3 g, 53 mmol) and ammonium chloride (0.28 g, 5.30 mmol) at ambient temperature. The reaction mixture was heated to 85° C. for 3 h. Completion of the reaction was confirmed by UPLC. The resulting reaction mixture was filtered through a bed of celite, washed with ethyl acetate and concentrated to afford tert-butyl 4-((5-amino-2-(tert-butylamino)pyrimidin-4-yl)amino)piperidine-1-carboxylate (2 g) as a brown solid. MS (ESI) m/z 365[M+1]⁺.

tert-Butyl 4-(8-((3,5-bis(trifluoromethyl)phenyl)amino)-2-(tert-butylamino)-9H-purin-9-yl)piperidine-1-carboxylate To a stirred solution of tert-butyl 4-((5-amino-2-(tert-butyl amino)pyrimidin-4-yl)amino)piperidine-1-carboxylate (0.45 g, 1.20 mmol) and 1-isothio cyanato-3,5-bis (trifluoromethyl)benzene (0.34 g, 1.20 mmol) in THF was added EDCI (0.5 g, 2.50 mmol) at ambient temperature. The reaction mixture was heated to 60° C. for 4 h. Completion of the reaction was confirmed by UPLC. The product was isolated and purified via standard methods to afford tert-butyl 4-(8-((3,5-bis(trifluoromethyl)phenyl)amino)-2-(tert-butylamino)-9H-purin-9-yl)piperidine-1-carboxylate (0.7 g, 64%) as a white solid. MS (ESI) m/z 602[M+1]⁺.

N8-(3,5-Bis(trifluoromethyl)phenyl)-N2-(tert-butyl)-9-(piperidin-4-yl)-9H-purine-2,8-diamine To a stirred solution of tert-butyl 4-(8-((3,5-bis(trifluoromethyl)phenyl)amino)-2-(tert-butylamino)-9H-purin-9-yl)piperidine-1 carboxylate (0.25 g, 0.40 mmol) in methanol (5 mL) was added HCl in dioxane (3 mL) at 0° C. The reaction mixture was stirred in at ambient temperature for 3 h. Completion of the reaction was confirmed by UPLC. The product was isolated and purified via standard methods to afford N8-(3,5-bis(trifluoromethyl)phenyl)-N2-(tert-butyl)-9-(piperidin-4-yl)-9H-purine-2,8-diamine (0.197 g, 95%) as an off white solid. MS (ESI) m/z 502.2[M+1]+: ¹H NMR (400 MHz, CD₃OD) δ 8.33 (brs, 2H), 8.28 (brs, 1H), 7.55 (s, 1H), 4.45-4.55 (m, 1H), 3.32-3.33 (m, 2H), 2.77-2.86 (m, 4H), 1.92-1.94 (m, 2H), 1.53 (s, 9H).

Example 23. N2-(tert-Butyl)-N8-(3-chloro-5-(trifluoromethyl)phenyl)-9-(pyrrolidin-3-ylmethyl)-9H-purine-2,8-diamine

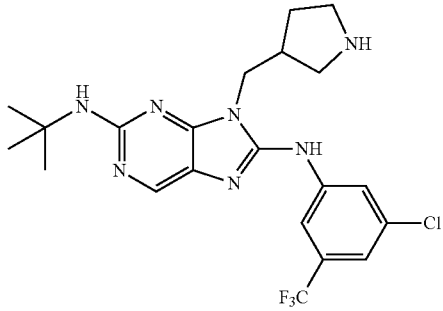 [SMILES: CC(C)(C)Nc1ncc2nc(Nc3cc(Cl)cc(C(F)(F)F)c3)n(CC3CCNC3)c2n1]

tert-Butyl 3-(((2-chloro-5-nitropyrimidin-4-yl)amino)methyl)pyrrolidine-1-carboxylate To a stirred solution of 2, 4-dichloro-5-nitropyrimidine (0.70 g, 3.61 mmol) and DIPEA (1.23 mL, 7.21 mmol) in IPA (10 mL) was added portionwise tert-butyl 3-(aminomethyl) pyrrolidine-1-carboxylate (0.72 g, 3.61 mmol) at 0° C. under nitrogen. The reaction mixture was slowly warm to ambient temperature and stirred for 1 h. Completion of the reaction was confirmed by UPLC. The product was isolated via standard methods to afford tert-butyl 3-(((2-chloro-5-nitropyrimidin-4-yl)amino)methyl)pyrrolidine-1-carboxylate (0.90 g) as pale yellow solid. MS (ESI) m/z 358.0, 359.0[M, M−1]+.

tert-Butyl 3-(((2-(tert-butylamino)-5-nitropyrimidin-4-yl)amino)methyl)pyrrolidine-1-carboxylate To a stirred solution of tert-butyl 3-(((2-chloro-5-nitropyrimidin-4-yl) amino)methyl)pyrrolidine-1-carboxylate (0.90 g, 2.51 mmol) and 2-methylpropan-2-amine (0.37 g, 5.02 mmol) in DMF (10 mL) was added sodium carbonate (0.40 g, 3.78 mmol) at ambient temperature. The reaction mixture was stirred at same temperature for 3 h. Completion of the reaction was confirmed by UPLC. The product was isolated purified via standard methods to afford tert-butyl 3-(((2-(tert-butylamino)-5-nitropyrimidin-4-yl)amino)methyl) pyrrolidine-1-carboxylate (0.50 g, 50%) as a pale yellow solid. MS (ESI) m/z 395.2[M+1]⁺.

tert-Butyl 3-(((5-amino-2-(tert-butylamino)pyrimidin-4-yl)amino)methyl)pyrrolidine-1-carboxylate To a stirred solution of tert-butyl 3-(((2-(tert-butylamino)-5-nitropyrimidin-4-yl) amino)methyl)pyrrolidine-1-carboxylate (0.50 g, 1.27 mmol) in ethanol and water (10 mL, 4:1) was added iron powder (0.71 g, 12.70 mmol) and ammonium chloride (0.07 g, 1.27 mmol) at ambient temperature. The reaction mixture was heated to 80° C. for 16 h. Completion of the reaction was confirmed by LCMS. The resulting reaction mixture was filtered through a bed of celite, washed with ethyl acetate and concentrated to afford tert-butyl 3-(((5-amino-2-(tert-butylamino)pyrimidin-4-yl)

amino)methyl)pyrrolidine-1-carboxylate (0.50 g) as a brown solid. MS (ESI) m/z 365.4[M+1]+ tert-Butyl 3-((2-(tert-butylamino)-8-((3-chloro-5-(trifluoromethyl)phenyl)amino)-9H-purin-9-yl)methyl)pyrrolidine-1-carboxylate To a stirred solution of tert-butyl 3-((((5-amino-2-(tert-butylamino)pyrimidin-4-yl)amino)methyl)pyrrolidine-1-carboxylate (0.50 g, 1.37 mmol) and 1-chloro-3-isothiocyanato-5-(trifluoromethyl)benzene (0.33 g, 1.37 mmol) in THF (10 mL) was added EDCI (0.52 g, 2.74 mmol) at ambient temperature. The reaction mixture was heated to 50° C. for 4 h. Completion of the reaction was confirmed by LCMS. The product was isolated and purified via standard methods to afford tert-butyl 3-((2-(tert-butylamino)-8-((3-chloro-5-(trifluoromethyl)phenyl)amino)-9H-purin-9-yl)methyl) pyrrolidine-1-carboxylate (0.21 g, 27%) as an off white solid. MS (ESI) m/z 568.2, 569.2[M, M+1]+.

N2-(tert-Butyl)-N8-(3-chloro-5-(trifluoromethyl)phenyl)-9-(pyrrolidin-3-ylmethyl)-9H-purine-2,8-diamine To a stirred solution of tert-butyl 3-((2-(tert-butylamino)-8-((3-chloro-5-(trifluoromethyl)phenyl)amino)-9H-purin-9-yl)methyl)pyrrolidine-1-carboxylate (0.21 g, 0.37 mmol) in methanol (2 mL) was added HCl in dioxane (2 mL) at 0° C. The reaction mixture was stirred at ambient temperature for 6 h. Completion of the reaction was confirmed by LCMS. The product was isolated and purified via standard methods to afford N2-(tert-butyl)-N8-(3-chloro-5-(trifluoromethyl)phenyl)-9-(pyrrolidin-3-ylmethyl)-9H-purine-2,8-diamine (0.15 g, 87%) as an off white solid. MS (ESI) m/z 468.2, 469.2[M, M+1]+; $^1$H NMR (400 MHz, CD$_3$OD) δ 8.26 (s, 1H), 8.17 (s, 1H), 7.99 (s, 1H), 7.34 (s, 1H), 4.25-4.38 (m, 2H), 3.33-3.41 (m, 2H), 3.19-3.25 (m, 1H), 3.06-3.11 (m, 1H), 2.92-2.98 (m, 1H), 2.12-2.17 (m, 1H), 1.86-1.91 (m, 1H), 1.57 (s, 9H).

Example 24. N8-(3-Chloro-5-(trifluoromethyl)phenyl)-N2-cyclobutyl-9-(pyrrolidin-3-yl)-9H-purine-2,8-diamine

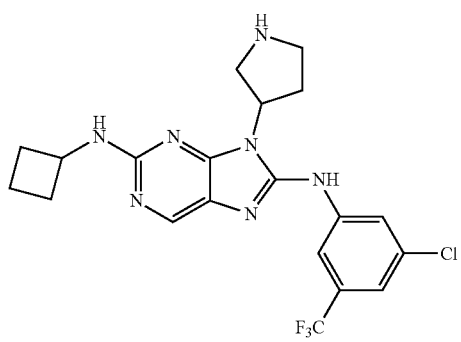 [SMILES: FC(F)(F)c1cc(Cl)cc(Nc2nc3cnc(NC4CCC4)nc3n2C2CCNC2)c1]

tert-Butyl 3-((2-(cyclobutylamino)-5-nitropyrimidin-4-yl)amino)pyrrolidine-1-carboxylate To a stirred solution of tert-butyl 3-((2-chloro-5-nitropyrimidin-4-yl)amino) pyrrolidine-1-carboxylate (1.90 g, 5.50 mmol), cyclobutylamine (0.78 g, 11 mmol) in DMF (15 mL) was added sodium carbonate (0.88 g, 8.30 mmol) at ambient temperature. The reaction mixture was stirred at same temperature for 3 h. Completion of the reaction was confirmed by UPLC. The product was isolated and purified via standard methods to afford tert-butyl 3-((2-(cyclobutylamino)-5-nitro pyrimidin-4-yl)amino)pyrrolidine-1-carboxylate (0.90 g, 43%) as a pale yellow solid. MS (ESI) m/z 379.7 [M+1]+.

tert-Butyl 3-((5-amino-2-(cyclobutylamino)pyrimidin-4-yl)amino)pyrrolidine-1-carboxylate To a stirred solution of tert-butyl 3-((2-(cyclobutylamino)-5-nitropyrimidin-4-yl)amino) pyrrolidine-1-carboxylate (0.90 g, 2.40 mmol) in ethanol and water (20 mL, 4:1) was added iron powder (1.33 g, 24 mmol) and ammonium chloride (0.13 g, 2.40 mmol) at ambient temperature. The reaction mixture was heated to 80° C. for 16 h. Completion of the reaction was confirmed by LCMS. The resulting reaction mixture was filtered through a bed of celite, washed with ethyl acetate and concentrated to afford tert-butyl 3-((5-amino-2-(cyclobutylamino)pyrimidin-4-yl)amino)pyrrolidine-1-carboxylate (0.90 g) as a brown solid. MS (ESI) m/z 349.7[M+1]+.

tert-Butyl 3-(8-((3-chloro-5-(trifluoromethyl)phenyl)amino)-2-(cyclobutylamino)-9H-purin-9-yl)pyrrolidine-1-carboxylate To a stirred solution of tert-butyl 3-((5-amino-2-(cyclobutylamino)pyrimidin-4-yl)amino)pyrrolidine-1-carboxylate (0.40 g, 1.14 mmol) and 1-chloro-3-isothiocyanato-5-(trifluoromethyl)benzene (0.27 g, 1.14 mmol) in THF (10 mL) was added EDCI (0.44 g, 2.30 mmol) at ambient temperature. The reaction mixture was heated to 60° C. for 4 h. Completion of the reaction was confirmed by LCMS. The product was isolated and purified via standard methods to afford tert-butyl 3-(8-((3-chloro-5-(trifluoromethyl)phenyl)amino)-2-(cyclobutylamino)-9H-purin-9-yl)pyrrolidine-1-carboxylate (0.16 g, 25%) as a pale yellow solid. MS (ESI) m/z 552, 553[M, M+1]+

N8-(3-Chloro-5-(trifluoromethyl)phenyl)-N2-cyclobutyl-9-(pyrrolidin-3-yl)-9H-purine-2,8-diamine To a stirred solution of tert-butyl 3-(8-((3-chloro-5-(trifluoromethyl) phenyl)amino)-2-(cyclobutylamino)-9H-purin-9-yl)pyrrolidine-1-carboxylate (0.16 g, 0.29 mmol) in methanol (3 mL) was added HCl in 1, 4-dioxane (2 mL) at 0° C. The reaction mixture was stirred at ambient temperature for 16 h. Completion of the reaction was confirmed by LCMS. The product was isolated and purified via standard methods to afford N8-(3-chloro-5-(trifluoromethyl)phenyl)-N2-cyclobutyl-9-(pyrrolidin-3-yl)-9H-purine-2,8-diamine (0.10 g, 77%) as an off white solid. MS (ESI) m/z 452.2, 453.2[M, M+1]+; $^1$H NMR (400 MHz, CD$_3$OD) δ 8.20 (s, 1H), 8.02 (s, 1H), 7.88 (s, 1H), 7.24 (s, 1H), 5.31-5.42 (m, 1H), 4.41-4.47 (m, 2H), 3.49-3.54 (m, 2H), 2.99-3.03 (m, 1H), 2.5-2.57 (m, 1H), 2.41-2.46 (m, 2H), 2.07-2.09 (m, 1H), 1.93-2.03 (m, 2H), 1.74-1.83 (m, 2H).

Example 25. N8-(3,5-Bis(trifluoromethyl) phenyl)-N2-cyclopentyl-9-(piperidin-4-yl)-9H-purine-2,8-diamine

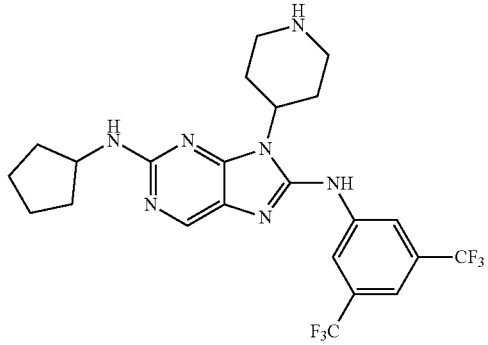 [SMILES: FC(F)(F)c1cc(Nc2nc3cnc(NC4CCCC4)nc3n2C2CCNCC2)cc(C(F)(F)F)c1]

tert-Butyl 4-(8-((3,5-bis(trifluoromethyl)phenyl)amino)-2-(cyclopentylamino)-9H-purin-9-yl)piperidine-1-carboxylate To a stirred solution of tert-butyl 4-((5-amino-2-(cyclopentylamino) pyrimidin-4-yl)amino)piperidine-1-carboxylate (0.6 g, 1.59 mmol) and 1-isothiocyanato-3,5-bis(trifluoromethyl)benzene (0.43 g, 1.59 mmol) in THF (6 mL) and ethanol (2 mL) was added EDCI (0.61 g, 3.18 mmol) at ambient temperature. The reaction mixture was heated to 50° C. for 4 h. Completion of the reaction was confirmed by LCMS. The product was isolated and purified via standard methods to afford tert-butyl 4-(8-((3, 5-bis(trifluoromethyl)phenyl)amino)-2-(cyclopentylamino)-9H-purin-9-yl)piperidine-1-carboxylate (0.35 g, 36%) as an off white solid. MS (ESI) m/z 613.6, 614.4[M, M+1]+.

N8-(3,5-Bis(trifluoromethyl)phenyl)-N2-cyclopentyl-9-(piperidin-4-yl)-9H-purine-2,8-diamine To a stirred solution of tert-butyl 4-(8-((3,5-bis (trifluoromethyl)phenyl)amino)-2-(cyclopentylamino)-9H-purin-9-yl) piperidine-1-carboxylate (0.35 g, 0.57 mmol) in methanol (4 mL) was added HCl in 1, 4-dioxane (4 mL) at 0° C. The reaction mixture was stirred at ambient temperature for 16 h. Completion of the reaction was confirmed by LCMS. The product was isolated and purified via standard methods to afford N8-(3,5-bis (trifluoromethyl) phenyl)-N2-cyclopentyl-9-(piperidin-4-yl)-9H-purine-2,8-diamine (0.24 g, 82%) as an off white solid. MS (ESI) m/z 514.2, 515.2[M=1, M+2]+; $^1$H NMR (400 MHz, CD$_3$OD) δ 8.28-8.33 (m, 3H), 7.57 (s, 1H), 4.61-4.63 (m, 1H), 4.33-4.38 (m, 1H), 3.49-3.56 (m, 2H), 2.99-3.15 (m, 4H), 2.06-2.12 (m, 4H), 1.78-1.84 (m, 2H), 1.68-1.76 (m, 2H), 1.52-1.59 (m, 2H).

Example 26. 9-(2-Amino-2-methylpropyl)-N2-(tert-butyl)-N8-(3-chloro-5-(trifluoromethyl)phenyl)-9H-purine-2,8-diamine

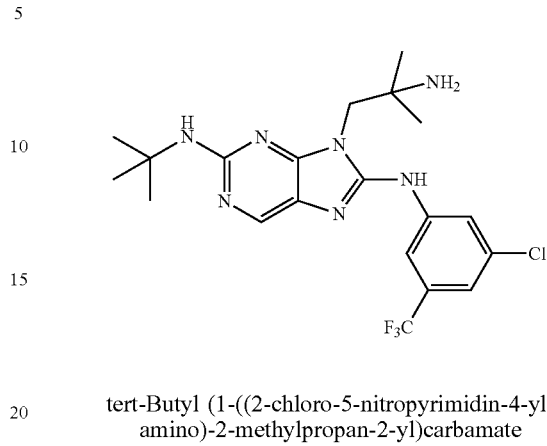

tert-Butyl (1-((2-chloro-5-nitropyrimidin-4-yl)amino)-2-methylpropan-2-yl)carbamate To a stirred solution of 2, 4-dichloro-5-nitropyrimidine (1 g, 5.13 mmol) and DIPEA (1.76 mL, 10.6 mmol) in IPA (10 mL) was added portion wise tert-butyl (1-amino-2-methylpropan-2-yl) carbamate (0.96 g, 5.15 mmol) at 0° C. under N2. The reaction mixture was slowly warm to ambient temperature and stirred for 1 h. Completion of the reaction was confirmed by LCMS. The product was isolated to afford tert-butyl (1-((2-chloro-5-nitropyrimidin-4-yl) amino)-2-methylpropan-2-yl)carbamate (1.8 g) as pale yellow solid. MS (ESI) m/z 346, 347 [M, M+1]+.

tert-Butyl (1-((2-(tert-butylamino)-5-nitropyrimidin-4-yl)amino)-2-methylpropan-2-yl) carbamate To a stirred solution of tert-butyl (1-((2-chloro-5-nitropyrimidin-4-yl)amino)-2-methylpropan-2-yl)carbamate (0.9 g, 2.6 mmol), 2-methylpropan-2-amine (0.38 g, 5.2 mmol) in DMF (10 mL) was added sodium carbonate (0.44 g, 4.16 mmol) at 0° C. The reaction mixture was stirred for ambient temperature for 3 h. Completion of the reaction was confirmed by UPLC. The product was isolated and purified via standard methods to afford tert-butyl (1-((2-(tert-butylamino)-5-nitropyrimidin-4-yl)amino)-2-methylpropan-2-yl)carbamate (0.6 g, 78%) as a pale yellow solid. MS (ESI) m/z 383.4 [M+1]+.

tert-Butyl (1-((5-amino-2-(tert-butylamino)pyrimidin-4-yl)amino)-2-methylpropan-2-yl) carbamate To a stirred solution of tert-butyl (1-((2-(tert-butylamino)-5-nitropyrimidin-4-yl) amino)-2-methylpropan-2-yl)carbamate (0.6 g, 1.57 mmol) in ethanol and water (15 mL, 4:1) was added Iron powder (0.89 g, 15.7 mmol) and ammonium chloride (0.8, 1.57 mmol) at ambient temperature. The reaction mixture was heated to 80° C. for 6 h. Completion of the reaction was confirmed by LCMS. The resulting reaction mixture was filtered through a bed of celite, washed with ethyl acetate and concentrated to afford tert-butyl (1-((5-amino-2-(tert-butylamino)pyrimidin-4-yl)amino)-2-methylpropan-2-yl) carbamate (0.53 g) as a brown solid. MS (ESI) m/z 353.3 [M+1]+ tert-Butyl (1-(2-(tert-butylamino)-8-((3-chloro-5-(trifluoromethyl)phenyl)amino)-9H-purin-9-yl)-2-methylpropan-2-yl)carbamate To a stirred solution of tert-butyl (1-((5-amino-2-(tert-butylamino)pyrimidin-4-yl)amino)-2-methylpropan-2-yl)

carbamate (0.5 g, 1.42 mmol) and 1-chloro-3-isothiocyanato-5-(trifluoromethyl)benzene (0.34 g, 1.42 mmol) in THF (10 mL) was added EDCI (0.54 g, 2.82 mmol) at ambient temperature. The reaction mixture was heated to 50° C. for 4 h. Completion of the reaction was confirmed by LCMS. The product was isolated and purified via standard methods to afford tert-butyl (1-(2-(tert-butylamino)-8-((3-chloro-5-(trifluoromethyl)phenyl)amino)-9H-purin-9-yl)-2-methylpropan-2-yl)carbamate (0.35 g, 44%) as an off white solid. MS (ESI) m/z 556, 557[M, M+1]$^+$.

9-(2-Amino-2-methylpropyl)-N2-(tert-butyl)-N8-chloro-5-(trifluoromethyl)phenyl)-9H-purine-2,8-diamine To a stirred solution of tert-butyl (1-(2-(tert-butylamino)-8-((3-chloro-5-(trifluoromethyl)phenyl)amino)-9H-purin-9-yl)-2-methylpropan-2-yl)carbamate (0.35 g, 0.63 mmol) in methanol (5 mL) was added HCl in dioxane (3 mL) at 0° C. The reaction mixture was stirred at ambient temperature for 16 h. Completion of the reaction was confirmed by LCMS. The product was isolated and purified via standard methods to afford 9-(2-amino-2-methylpropyl)-N2-(tert-butyl)-N8-(3-chloro-5-(trifluoromethyl)phenyl)-9H-purine-2,8-diamine (0.26 g, 90%) as an off white solid. MS (ESI) m/z 456.2, 457.2[M, M+1]+; $^1$H NMR (400 MHz, CD$_3$OD) δ 8.24 (s, 1H), 8.01 (s, 1H), 7.84 (s, 1H), 7.26 (s, 1H), 4.09 (s, 2H), 1.51 (s, 9H), 1.29 (s, 6H).

Example 27. 9-(2-Aminopropyl)-N8-(3-chloro-5-(trifluoromethyl)phenyl)-N2-cyclopentyl 9H-purine-2,8-diamine

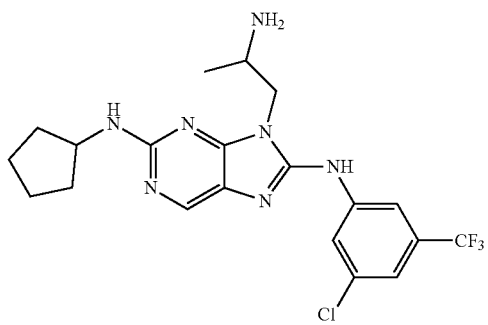 [SMILES: CC(N)Cn1c(Nc2cc(Cl)cc(C(F)(F)F)c2)nc2cnc(NC3CCCC3)nc21]

tert-Butyl (1-((2-chloro-5-nitropyrimidin-4-yl)amino)propan-2-yl)carbamate

To a stirred solution of 2, 4-dichloro-5-nitropyrimidine (1.00 g, 5.15 mmol) and DIPEA (1.76 mL, 10.30 mmol) in IPA (10 mL) was added portionwise tert-butyl (1-aminopropan-2-yl) carbamate (0.90 g, 5.15 mmol) at 0° C. under nitrogen. The reaction mixture was slowly warm to ambient temperature and stirred for 1 h. Completion of the reaction was confirmed by LCMS. The product was isolated to afford tert-butyl (1-((2-chloro-5-nitropyrimidin-4-yl) amino)propan-2-yl)carbamate (2.10 g) as brown gummy solid. MS (ESI) m/z 332.3, 333.3 [M, M+1]$^+$.

tert-Butyl (1-((2-(cyclopentylamino)-5-nitropyrimidin-4-yl)amino)propan-2-yl) carbamate To a stirred solution of tert-butyl (1-((2-chloro-5-nitropyrimidin-4-yl) amino) propan-2-yl)carbamate (1.00 g, 3.01 mmol), cyclopentanamine (0.51 g, 6.02 mmol) in DMF (10 mL) was added sodium carbonate (0.48 g, 4.51 mmol) at ambient temperature. The reaction mixture was stirred at same temperature for 3 h. Completion of the reaction was confirmed by UPLC. The product was isolated purified via standard methods to afford tert-butyl (1-((2-(cyclopentylamino)-5-nitropyrimidin-4-yl)amino)propan-2-yl)carbamate (0.70 g, 78%) as a pale yellow solid. MS (ESI) m/z 351.2[M+1]+.

tert-Butyl (1-((5-amino-2-(cyclopentylamino)pyrimidin-4-yl)amino)propan-2-yl) carbamate To a stirred solution of tert-butyl (1-((2-(cyclopentylamino)-5-nitropyrimidin-4-yl)amino)propan-2-yl)carbamate (0.70 g, 2 mmol) in ethanol and water (10 mL, 4:1) was added iron powder (1.12 g, 20 mmol) and ammonium chloride (0.11 g, 2 mmol) at ambient temperature. The reaction mixture was heated to 80° C. for 16 h. Completion of the reaction was confirmed by LCMS. The resulting reaction mixture was filtered through a bed of celite, washed with ethyl acetate and concentrated to afford tert-butyl (1-((5-amino-2-(cyclopentylamino)pyrimidin-4-yl)amino) propan-2-yl)carbamate (0.70 g) as a brown solid. MS (ESI) m/z 321.4[M+1]$^+$.

tert-Butyl (1-(8-((3-chloro-5-(trifluoromethyl)phenyl)amino)-2-(cyclopentylamino)-9H-purin-9-yl) propan-2-yl)carbamate To a stirred solution of tert-butyl (1-((5-amino-2-(cyclopentylamino)pyrimidin-4-yl)amino)propan-2-yl)carbamate (0.70 g, 2.18 mmol) and 3-chloro-5-isothiocyanatobenzonitrile (0.25 g, 2.18 mmol) in THF (10 mL) was added EDCI (0.83 g, 4.36 mmol) at ambient temperature. The reaction mixture was heated to 60° C. for 4 h. Completion of the reaction was confirmed by LCMS. The product was isolated and purified via standard methods to afford tert-butyl (1-(8-((3-chloro-5-(trifluoromethyl)phenyl)amino)-2-(cyclopentylamino)-9H-purin-9-yl)propan-2-yl)carbamate (0.46 g, 38%) as an off white solid. MS (ESI) m/z 554.2, 555.2[M, M+1]$^+$

9-(2-Aminopropyl)-N8-(3-chloro-5-(trifluoromethyl) phenyl)-N2-cyclopentyl-9H-purine-2,8-diamine To a stirred solution of tert-butyl (1-(8-((3-chloro-5-(trifluoromethyl) phenyl)amino)-2-(cyclopentylamino)-9H-purin-9-yl)propan-2-yl)carbamate (0.45 g, 0.81 mmol) in methanol (2 mL) was added HCl in dioxane (5 mL) at 0° C. The reaction mixture was stirred at ambient temperature for 6 h. Completion of the reaction was confirmed by LCMS. The product was isolated and purified via standard methods to afford 9-(2-aminopropyl)-N8-(3-chloro-5-(trifluoromethyl)phenyl)-N2-cyclopentyl-9H-purine-2,8-diamine (0.34 g, 92%) as an off white solid. MS (ESI) m/z 454.1, 456.1[M, M+1]$^+$; $^1$H NMR (400 MHz, CD$_3$OD) δ 8.18 (s, 1H), 7.99 (s, 1H), 7.85 (s, 1H), 7.31 (s, 1H), 4.27-4.37 (m, 3H), 3.81-3.86 (m, 1H), 2.04-2.09 (m, 2H), 1.75-1.80 (m, 2H), 1.65-1.72 (m, 2H), 1.53-1.59 (m, 2H), 1.40 (d, J=6.7 Hz, 3H).

Example 28. N8-(3-Chloro-5-(trifluoromethyl)phenyl)-N2-cyclopentyl-9-(2-(methylamino)ethyl)-9H-purine-2,8-diamine

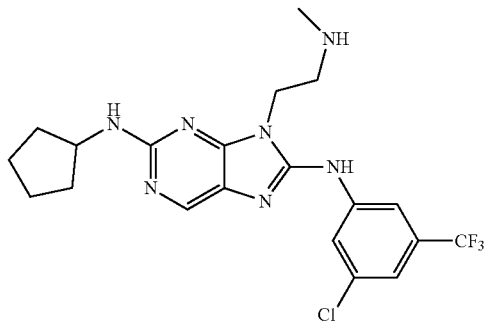 [SMILES: CNCCn1c(Nc2cc(Cl)cc(C(F)(F)F)c2)nc2cnc(NC3CCCC3)nc21]

tert-Butyl (2-((2-chloro-5-nitropyrimidin-4-yl)amino)ethyl)(methyl)carbamate

To a stirred solution of 2, 4-dichloro-5-nitropyrimidine (1.00 g, 5.15 mmol) and DIPEA (1.76 mL, 10.30 mmol) in IPA (10 mL) was added portion wise tert-butyl (2-aminoethyl)(methyl) carbamate (0.89 g, 5.15 mmol) at 0° C. under nitrogen. The reaction mixture was slowly warm to ambient temperature and stirred for 1 h. Completion of the reaction was confirmed by LCMS. The product was isolated to afford tert-butyl (2-((2-chloro-5-nitropyrimidin-4-yl) amino)ethyl)(methyl)carbamate (1.80 g) as brown gummy solid. MS (ESI) m/z 332.4, 333.4 [M, M+1]+.

tert-Butyl (2-((2-(cyclopentylamino)-5-nitropyrimidin-4-yl)amino)ethyl)(methyl) carbamate To a stirred solution of tert-butyl (2-((2-chloro-5-nitropyrimidin-4-yl)amino) ethyl)(methyl)carbamate (0.90 g, 2.71 mmol), cyclopentanamine (0.46 g, 5.42 mmol) in DMF (10 mL) was added sodium carbonate (0.43 g, 4.06 mmol) at ambient temperature. The reaction mixture was stirred at same temperature for 3 h. Completion of the reaction was confirmed by UPLC. The product was isolated purified via standard methods to afford tert-butyl (2-((2-(cyclopentylamino)-5-nitropyrimidin-4-yl)amino)ethyl)(methyl)carbamate (0.80 g, 78%) as a pale yellow solid. MS (ESI) m/z 381.4 [M+1]+.

tert-Butyl (2-((5-amino-2-(cyclopentylamino)pyrimidin-4-yl)amino)ethyl)(methyl) carbamate To a stirred solution of tert-butyl (2-((2-(cyclopentylamino)-5-nitropyrimidin-4-yl)amino)ethyl)(methyl) carbamate (0.80 g, 2.10 mmol) in ethanol and water (10 mL, 4:1) was added iron powder (1.18 g, 21 mmol) and ammonium chloride (0.11 g, 2.10 mmol) at ambient temperature. The reaction mixture was heated to 80° C. for 6 h. Completion of the reaction was confirmed by LCMS. The resulting reaction mixture was filtered through a bed of celite, washed with ethyl acetate and concentrated to afford tert-butyl (2-((5-amino-2-(cyclopentylamino)pyrimidin-4-yl)amino) ethyl)(methyl) carbamate (0.81 g) as a brown solid. MS (ESI) m/z 351.2[M+1]+.

tert-Butyl (2-(8-((3-chloro-5-(trifluoromethyl)phenyl)amino)-2-(cyclopentylamino)-9H-purin-9-yl)ethyl)(methyl)carbamate To a stirred solution of tert-butyl (2-((5-amino-2-(cyclopentylamino)pyrimidin-4-yl)amino)ethyl)(methyl) carbamate (0.40 g, 1.14 mmol) and 3-chloro-5-isothiocyanatobenzonitrile (0.27 g, 1.14 mmol) in THF (10 mL) was added EDCI (0.44 g, 2.28 mmol) at ambient temperature. The reaction mixture was heated to 60° C. for 4 h. Completion of the reaction was confirmed by LCMS. The product was isolated and purified via standard methods to afford tert-butyl (2-(8-((3-chloro-5-(trifluoromethyl)phenyl)amino)-2-(cyclopentylamino)-9H-purin-9-yl)ethyl)(methyl)carbamate (0.25 g, 40%) as an off white solid. MS (ESI) m/z 554.1, 555.1[M, M+1]+

N8-(3-Chloro-5-(trifluoromethyl)phenyl)-N2-cyclopentyl-9-(2-(methylamino)ethyl)-9H-purine-2,8-diamine To a stirred solution of tert-butyl (2-(8-((3-chloro-5-(trifluoromethyl) phenyl)amino)-2-(cyclopentylamino)-9H-purin-9-yl)ethyl)(methyl)carbamate (0.24 g, 0.43 mmol) in methanol (2 mL) was added HCl in dioxane (3 mL) at 0° C. The reaction mixture was stirred at ambient temperature for 4 h. Completion of the reaction was confirmed by LCMS. The product was isolated and purified via standard methods to afford N8-(3-chloro-5-(trifluoromethyl)phenyl)-N2-cyclopentyl-9-(2-(methylamino)ethyl)-9H-purine-2,8-diamine (0.17 g, 90%) as an off white solid. MS (ESI) m/z 454.1, 455.1 [M, M+1]+; 1H NMR (400 MHz, CD3OD) δ 8.22 (s, 1H), 8.06 (s, 1H), 7.89 (s, 1H), 7.32 (s, 1H), 4.35-4.36 (m, 2H), 4.27-4.30 (m, 1H), 3.22-3.29 (m, 2H), 2.66 (s, 3H), 2.05-2.10 (m, 2H), 1.78-1.80 (m, 2H), 1.67-1.69 (m, 2H), 1.53-1.60 (m, 2H).

Example 29. 9-(3-Aminobutyl)-N2-(tert-butyl)-N8-(3-chloro-5-(trifluoromethyl)phenyl)-9H-purine-2,8-diamine

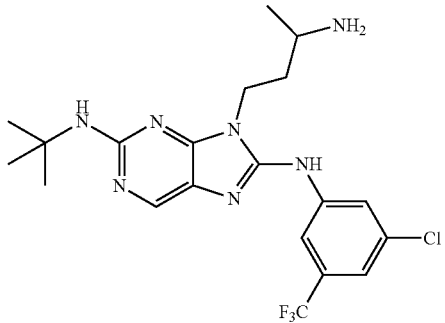 [SMILES: CC(N)CCn1c(Nc2cc(Cl)cc(C(F)(F)F)c2)nc2cnc(NC(C)(C)C)nc21]

tert-Butyl (4-((2-chloro-5-nitropyrimidin-4-yl)amino)butan-2-yl)carbamate

To a stirred solution of 2, 4-dichloro-5-nitropyrimidine (0.50 g, 2.57 mmol) and DIPEA (0.88 mL, 5.14 mmol) in IPA (10 mL) was added portionwise tert-butyl (4-aminobutan-2-yl)carbamate (0.48 g, 2.57 mmol) at 0° C. under nitrogen. The reaction mixture was slowly warm to ambient temperature and stirred for 1 h. Completion of the reaction was confirmed by UPLC. The product was isolated via standard methods to afford tert-butyl (4-((2-chloro-5-nitropyrimidin-4-yl)amino)butan-2-yl)carbamate (0.90 g) as pale yellow solid. MS (ESI) m/z 346.0, 347.1 [M, M+1]+.

tert-Butyl (4-((2-(tert-butylamino)-5-nitropyrimidin-4-yl)amino)butan-2-yl)carbamate To a stirred solution of tert-butyl (4-((2-chloro-5-nitropyrimidin-4-yl)amino)butan-2-yl) carbamate (0.90 g, 2.60 mmol), 2-methylpropan-2-amine (0.38 g, 5.20 mmol) in DMF (15 mL) was added sodium carbonate (0.41 g, 3.90 mmol) at ambient temperature. The reaction mixture was stirred at same temperature for 3 h. Completion of the reaction was confirmed by UPLC. The product was isolated and purified via standard methods to afford tert-butyl (4-((2-(tert-butylamino)-5-nitropyrimidin-4-yl)amino)butan-2-yl)carbamate (0.45 g, 46%) as a pale yellow solid. MS (ESI) m/z 383.2[M+1]+.

tert-Butyl (4-((5-amino-2-(tert-butylamino)pyrimidin-4-yl)amino)butan-2-yl)carbamate To a stirred solution of tert-butyl (4-((2-(tert-butylamino)-5-nitropyrimidin-4-yl)amino)butan-2-yl)carbamate (0.40 g, 1.04 mmol) in ethanol and water (10 mL, 4:1) was added iron powder (0.57 g, 10.40 mmol) and ammonium chloride (0.06 g, 1.04 mmol) at ambient temperature. The reaction mixture was heated to 80° C. for 4 h. Completion of the reaction was confirmed by LCMS. The resulting reaction mixture was filtered through a bed of celite, washed with ethyl acetate and concentrated to afford tert-butyl (4-((5-amino-2-(tert-butylamino)pyrimidin-4-yl)amino)butan-2-yl)carbamate (0.40 g) as a brown solid. MS (ESI) m/z 353.6[M+1]+.

tert-Butyl (4-(2-(tert-butylamino)-8-((3-chloro-5-(trifluoromethyl)phenyl)amino)-9H-purin-9-yl)butan-2-yl)carbamate To a stirred solution of tert-butyl (4-((5-amino-2-(tert-butylamino)pyrimidin-4-yl)amino)butan-2-yl)carbamate (0.40 g, 1.14 mmol) and 1-chloro-3-isothiocyanato-5-(trifluoromethyl)benzene (0.27 g, 1.14 mmol) in THF (10 mL) was added EDCI (0.43 g, 2.28 mmol) at ambient temperature. The reaction mixture was heated to 60° C. for 4 h. Completion of the reaction was confirmed by LCMS. The product was isolated and purified via standard methods to afford tert-butyl (4-(2-(tert-butylamino)-8-((3-chloro-5-(trifluoromethyl)phenyl)amino)-9H-purin-9-yl)butan-2-yl)carbamate (0.30 g, 47%) as a pale yellow solid. MS (ESI) m/z 556.3, 557.21[M, M+1]+.

9-(3-Aminobutyl)-N2-(tert-butyl)-N8-(3-chloro-5-(trifluoromethyl)phenyl)-9H-purine-2,8-diamine To a stirred solution of tert-butyl (4-(2-(tert-butylamino)-8-((3-chloro-5-(trifluoromethyl)phenyl)amino)-9H-purin-9-yl)butan-2-yl)carbamate (030 g, 0.54 mmol) in methanol (3 mL) was added HCl in 1,4-dioxane (3 mL) at 0° C. The reaction mixture was stirred at ambient temperature for 16 h. Completion of the reaction was confirmed by LCMS. The product was isolated and purified via standard methods to afford 9-(3-aminobutyl)-N2-(tert-butyl)-N8-(3-chloro-5-(trifluoromethyl)phenyl)-9H-purine-2,8-diamine (0.20 g, 81%) as an off white solid. MS (ESI) m/z 456.2, 457.2[M, M+1]+; $^1$H NMR (400 MHz, CD$_3$OD) δ 8.21 (brs, 1H), 8.07 (brs, 1H), 7.93 (brs, 1H), 7.31 (s, 1H), 4.26-4.37 (m, 2H), 3.31-3.35 (m, 1H), 2.09-2.20 (m, 2H), 1.50 (s, 9H), 1.42 (d, J=6.5 Hz, 3H).

Example 30. 9-(3-Aminobutyl)-N8-(3-chloro-5-(trifluoromethyl)phenyl)-N2-cyclopentyl-9H-purine-2,8-diamine

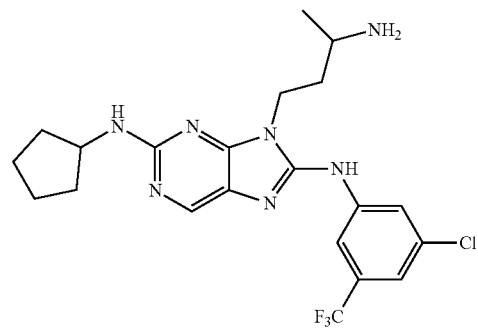 [SMILES: CC(N)CCn1c(Nc2cc(Cl)cc(C(F)(F)F)c2)nc2cnc(NC3CCCC3)nc21]

tert-Butyl (4-((2-chloro-5-nitropyrimidin-4-yl)amino)butan-2-yl)carbamate

To a stirred solution of 2, 4-dichloro-5-nitropyrimidine (1.50 g, 7.73 mmol) and DIPEA (2.64 mL, 15.46 mmol) in IPA (20 mL) was added portionwise tert-butyl (4-aminobutan-2-yl)carbamate (1.45 g, 7.73 mmol) at 0° C. under nitrogen. The reaction mixture was slowly warm to ambient temperature and stirred for 1 h. Completion of the reaction was confirmed by UPLC. The product was isolated via standard methods to afford tert-butyl (4-((2-chloro-5-nitropyrimidin-4-yl)amino)butan-2-yl)carbamate (0.90 g) as pale yellow solid. MS (ESI) m/z 346.4, 347.4[M, M+1]+.

tert-Butyl (4-((2-(cyclopentylamino)-5-nitropyrimidin-4-yl)amino)butan-2-yl)carbamate To a stirred solution of tert-butyl (4-((2-chloro-5-nitropyrimidin-4-yl) carbamate (0.90 g, 2.60 mmol), and cyclopentanamine (0.44 g, 5.20 mmol) in DMF (15 mL) was added sodium carbonate (0.41 g, 3.90 mmol) at ambient temperature. The reaction mixture was stirred at same temperature for 3 h. Completion of the reaction was confirmed by UPLC. The product was isolated and purified via standard methods to afford tert-butyl (4-((2-(cyclopentylamino)-5-nitropyrimidin-4-yl)amino)butan-2-yl)carbamate 0.60 g, 58%) as a pale yellow solid. MS (ESI) m/z 395.1[M+1]+.

tert-Butyl (4-((5-amino-2-(cyclopentylamino)pyrimidin-4-yl)amino)butan-2-yl) carbamate To a stirred solution of tert-butyl (4-((2-(cyclopentylamino)-5-nitropyrimidin-4-yl)amino)butan-2-yl)carbamate (0.60 g, 1.52 mmol) in ethanol and water (10 mL, 4:1) was added iron powder (0.85 g, 15.20 mmol) and ammonium chloride (0.08 g, 1.52 mmol) at ambient temperature. The reaction mixture was heated to 80° C. for 4 h. Completion of the reaction was confirmed by LCMS. The resulting reaction mixture was filtered through a bed of celite, washed with ethyl acetate and concentrated to afford tert-butyl (4-((5-amino-2-(cyclopentylamino)pyrimidin-4-yl)amino) butan-2-yl)carbamate (0.40 g) as a brown solid. MS (ESI) m/z 365.6[M+1]+ tert-Butyl (4-(8-((3-chloro-5-(trifluoromethyl)phenyl)amino)-2-(cyclopentylamino)-9H-purin-9-yl)butan-2-yl)carbamate To a stirred solution of tert-butyl (4-((5-amino-2-(cyclopentylamino)pyrimidin-4-yl)amino)butan-2-yl)carbamate (0.40 g, 1.09 mmol) and 1-chloro-3-isothiocyanato-5-(trifluoromethyl)benzene (0.26 g, 1.09 mmol) in THF (10 mL) was added EDCI (0.42 g, 2.18 mmol) at ambient temperature. The reaction mixture was heated to 60° C. for 4 h. Completion of the reaction was confirmed by LCMS. The product was isolated and purified via standard methods to afford tert-butyl (4-(8-((3-chloro-5-(trifluoromethyl) phenyl)amino)-2-(cyclopentylamino)-9H-purin-9-yl)butan-2-yl)carbamate (0.12 g, 19%) as a pale yellow solid. MS (ESI) m/z 568.1, 569.1[M, M+1]+.

9-(3-Aminobutyl)-N8-(3-chloro-5-(trifluoromethyl)phenyl)-N2-cyclopentyl-9H-purine-2,8-diamine To a stirred solution of tert-butyl (4-(8-((3-chloro-5-(trifluoromethyl)phenyl) amino)-2-(cyclopentylamino)-9H-purin-9-yl)butan-2-yl)carbamate (0.12 g, 0.21 mmol) in methanol (3 mL) was added HCl in dioxane (1 mL) at 0° C. The reaction mixture was stirred at ambient temperature for 16 h. Completion of the reaction was confirmed by LCMS. The product was isolated and purified via standard methods to afford 9-(3-aminobutyl)-N8-(3-chloro-5-(trifluoromethyl)phenyl)-N2-cyclopentyl-9H-purine-2,8-diamine (0.06 g, 78%) as an off white solid. MS (ESI) m/z 468.2, 469.2[M, M+1]+; $^1$H NMR (400 MHz, CD$_3$OD) δ 8.21 (s, 1H), 8.05 (s, 1H), 7.90 (brs, 1H), 7.29 (s, 1H), 4.26-4.29 (m, 3H), 3.05-3.06 (m, 1H), 2.08-2.09 (m, 3H), 1.94-1.95 (m, 1H), 1.79-1.80 (m, 2H), 1.66-1.67 (m, 2H), 1.55-1.56 (m, 2H), 1.31 (d, J=6.4 Hz, 3H).

Example 31. N8-(3-Chloro-5-(trifluoromethyl)phenyl)-N2-(1-methylcyclopentyl)-9-(piperidin-4-yl)-9H-purine-2,8-diamine

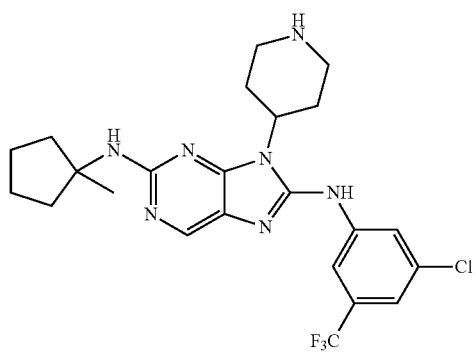 [SMILES: CC1(Nc2ncc3nc(Nc4cc(Cl)cc(C(F)(F)F)c4)n(C4CCNCC4)c3n2)CCCC1]

tert-Butyl 4-((2-((1-methylcyclopentyl)amino)-5-nitropyrimidin-4-yl)amino)piperidine-1-carboxylate To a stirred solution of tert-butyl 4-((2-chloro-5-nitropyrimidin-4-yl)amino) piperidine-1-carboxylate (1.40 g, 4 mmol) in DMF (10 mL) was added 1-methylcyclopentan-1-amine (0.40 g, 14 mmol) and sodium carbonate (0.90 g, 8 mmol) at ambient temperature. The reaction mixture was stirred at same temperature for 4 h. Completion of the reaction was confirmed by UPLC. The product was isolated and purified via standard methods to afford tert-butyl 4-((2-((1-methylcyclopentyl)amino)-5-nitropyrimidin-4-yl)amino)piperidine-1-carboxylate (1 g, 59%) as an off white solid. MS (ESI) m/z 421[M+1]+.

tert-Butyl 4-((5-amino-2-((1-methylcyclopentyl)amino)pyrimidin-4-yl)amino)piperidine-1-carboxylate To a stirred solution of tert-butyl 4-((2-((1-methylcyclopentyl)amino)-5-nitropyrimidin-4-yl)amino)piperidine-1-carboxylate (1.00 g, 2.40 mmol) in ethanol and water (20 mL, 3:1) was added iron powder (1.30 g, 24 mmol) and ammonium chloride (0.13 g, 2.40 mmol) at ambient temperature. The reaction mixture was heated to 85° C. for 4 h. Completion of the reaction was confirmed by UPLC. The resulting reaction mixture was filtered through a bed of celite, washed with ethyl acetate and concentrated to afford tert-butyl 4-((5-amino-2-((1-methylcyclopentyl)amino)pyrimidin-4-yl)amino)piperidine-1-carboxylate (0.90 g) as a brown solid. MS (ESI) m/z 391[M+1]+.

tert-Butyl 4-(8-((3-chloro-5-(trifluoromethyl)phenyl)amino)-2-((1-methylcyclopentyl) amino)-9H-purin-9-yl)piperidine-1-carboxylate To a stirred solution of tert-butyl 4-((5-amino-2-((1-methylcyclopentyl)amino)pyrimidin-4-yl)amino)piperidine-1-carboxylate (0.50 g, 1.30 mmol) and 1-chloro-3-isothiocyanato-5-(trifluoromethyl)benzene (0.30 g, 1.30 mmol) in THF was added EDCI (0.50 g, 2.60 mmol) at ambient temperature. The reaction mixture was heated to 60° C. for 4 h. Completion of the reaction was confirmed by UPLC. The product was isolated and purified via standard methods to afford tert-butyl 4-(8-((3-chloro-5-(trifluoromethyl)phenyl)amino)-2-((1-methylcyclopentyl)amino)-9H-purin-9-yl)piperidine-1-carboxylate (0.35 g; 46%) as an off white solid. MS (ESI) m/z 594, 595[M, M+1]+.

N8-(3-Chloro-5-(trifluoromethyl)phenyl)-N2-(1-methylcyclopentyl)-9-(piperidin-4-yl)-9H-purine-2,8-diamine To a stirred solution of tert-butyl 4-(8-((3-chloro-5-(trifluoromethyl) phenyl)amino)-2-((1-methylcyclopentyl) amino)-9H-purin-9-yl)piperidine-1-carboxylate (0.35 g, 0.59 mmol) in MeOH (10 mL) was added HCl in dioxane (5 mL) at 0° C. The reaction mixture was stirred at ambient temperature for 4 h. Completion of the reaction was confirmed by UPLC The product was isolated and purified via standard methods to afford N8-(3-chloro-5-(trifluoromethyl)phenyl)-N2-(1-methylcyclopentyl)-9-(piperidin-4-yl)-9H-purine-2, 8-diamine (0.18 g, 87%) as an off white solid. MS (ESI) m/z 494.2, 495.2[M, M+1]+; $^1$H NMR (400 MHz, CD$_3$OD) δ 8.27 (brs, 1H), 8.08 (brs, 1H), 7.90 (brs, 1H), 7.32 (s, 1H), 4.62-4.68 (m, 1H), 3.54-3.57 (m, 2H), 3.10-3.16 (m, 2H), 2.93-3.03 (m, 2H), 2.12-2.15 (m, 4H), 1.75-1.82 (m, 6H), 1.60 (s, 3H).

ANTI-MALARIAL In Vitro ASSAYS

*Plasmodium falciparum*: In Vitro [$^3$H]-Hypoxanthine Parasite Growth Inhibition Assay.
Preparation of Host Erythrocytes:
Human erythrocytes for parasite culture were prepared by drawing blood into heparin-treated tubes and washing several times in RPMI 1640 medium to separate the erythrocytes from the plasma and buffy coat. Separation was achieved by centrifuging the blood at 500×g for 5 minutes in a swing-out rotor. Leukocyte-free erythrocytes were typically stored at 50% hematocrit (i.e., 1 volume of malaria culture media for 1 volume of packed erythrocytes, corresponding to approximately 5×10^9 cells/mL).

Parasite Culture Conditions:

P. falciparum asexual blood stage parasites were propagated at 37° C. in malaria culture media at 3-5% hematocrit in a reduced oxygen environment (e.g., a custom mixture of 5% $CO_2$, 5% $O_2$ and 90% $N_2$). Lines were conveniently cultured in 6-24 well tissue culture plates in a modular chamber (Billups-Rothenberg, Del Mar, Calif., www.brincubator.com), with plates containing sterile water on the bottom to increase humidity and minimize desiccation. These chambers were suffused with the low $O_2$ gas and maintained at 37° C. in an incubator designed to minimize temperature fluctuations. Parasites could also be cultured in flasks that are individually gassed, or alternatively placed in flasks that permit gas exchange through the cap (in which case the incubator needs to be continuously infused with a low $O_2$ gas mixture). Parasites typically propagated 3-8 fold every 48 h, thus care was taken to avoid parasite cultures attaining too high a parasitemia (i.e., percentage of erythrocytes that are parasitized) for healthy growth. Optimal growth was at 0.5-4% parasitemia. Parasites were most suitable for assays when they are 2-5% parasitemia, and mostly ring stages with few or no gametocytes.

Preparation of Compounds for Assay:

The Purine Compounds were dissolved in 100% dimethyl sulfoxide (DMSO) and stored at −80° C. (or −20° C.). For the assay, serial compound dilutions (either 2× or customized) were made in low hypoxanthine medium (see above) and added to 96-well culture plates at 100 mL per well. Compounds were added to columns 3-12 (test samples), with columns 1 and 2 reserved for wells with low hypoxanthine medium without compound. Once completed, plates were placed into their own modular chamber, gassed and placed at 37° C. These plates were set up no more than three hours prior to addition of the parasites.

Assay Conditions:

Parasites were diluted to a 2× stock consisting of 0.6% to 0.9% parasitemia and 3.2% hematocrit in low hypoxanthine medium, and 100 mL were added per well already containing 100 mL of low hypoxanthine medium with or without compound (present at different concentrations). Plates were then incubated in a gassed modular chamber at 37° C. for 48 h. After this time, 100 mL of culture supernatant from each well was removed and replaced with 100 mL of low hypoxanthine medium containing a final concentration of 7.5 mCi/mL of [$^3$H]-hypoxanthine (1 mCi/mL stock, Amersham Biosciences). After a further 24 h, the plates were placed at −80° C. for at least 1 h to freeze the cells. Plates are then thawed and the cells were harvested onto glass fiber filters (Wallac, Turku, Finland). Filters were dried for 30 minutes at 80° C., placed in sample bags (Wallac), and immersed in scintillation fluid (Ecoscint A; National Diagnostic, Atlanta, Ga.). Radioactive emissions are counted in a 1205 Betaplate reader (Wallac). Mean counts per minute (cpm) were generally in the range 20,000-60,000, with an acceptable minimum of 10,000. Percentage reduction in [3H]-hypoxanthine uptake was equal to 100× ((geometric mean cpm of no compound samples)−(mean cpm of test samples))/(geometric mean cpm of no compound samples). Percentage reductions were used to plot percentage inhibition of growth as a function of compound concentrations. IC50 values were determined by linear regression analyses on the linear segments of the curves. (D. A. Fidock, P. J. Rosenthal, S. L. Croft, R. Brun, S. Nwaka, Nature Rev. Drug Discovery, 2004, 3, 509-520.)

Assay Data Analysis.

Assay data is analyzed using Graph pad prism ver.5 software. A variable sigmoid dose response curve is plotted keeping log concentrations at X-axis and % inhibition at Y-axis.

Activity Tables

Each of the compounds in Table 1 was tested in at least one of the malaria assays and was found to have activity therein, with all of the Purine Compounds of Formula (I) having an $IC_{50}$ below or at 1.2 µM in the assay, with some compounds having an $IC_{50}$ between 0.5 and 1.2 µM (activity level A), some having an $IC_{50}$ between 0.2 µM and 0.5 µM (activity level B), some having an $IC_{50}$ between 0.1 µM and 0.2 µM (activity level C), and some having $IC_{50}$ below 0.1 µM (activity level D).

TABLE 1

| Cpd # | Structure | Cmdp Name | MH+ | Act Class |
|---|---|---|---|---|
| 1 | [structure] | 9-(2-(1H-imidazol-1-yl)ethyl)-N2-tert-butyl-N8-(3-chlorophenyl)-9H-purine-2,8-diamine | 411.2 | B |

TABLE 1-continued
| Cpd # | Structure | Cmdp Name | MH+ | Act Class |
|---|---|---|---|---|
| 2 | 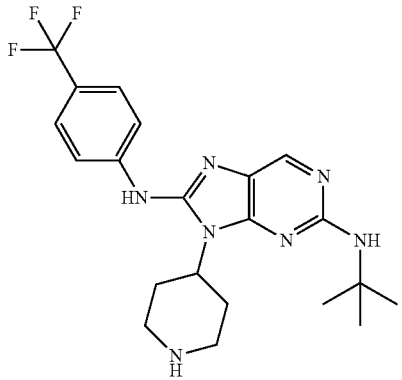 [SMILES: CC(C)(C)Nc1ncc2nc(Nc3ccc(C(F)(F)F)cc3)n(C3CCNCC3)c2n1] | N2-tert-butyl-9-(piperidin-4-yl)-N8-(4-(trifluoromethyl)phenyl)-9H-purine-2,8-diamine | 434.2 | B |
| 3 | 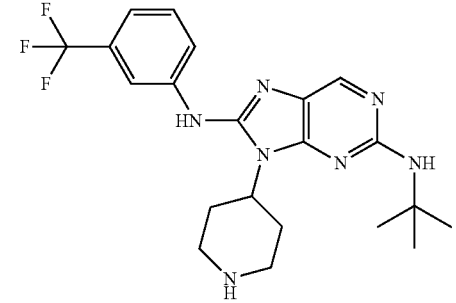 [SMILES: CC(C)(C)Nc1ncc2nc(Nc3cccc(C(F)(F)F)c3)n(C3CCNCC3)c2n1] | N2-tert-butyl-9-(piperidin-4-yl)-N8-(3-(trifluoromethyl)phenyl)-9H-purine-2,8-diamine | 434.2 | D |
| 4 | 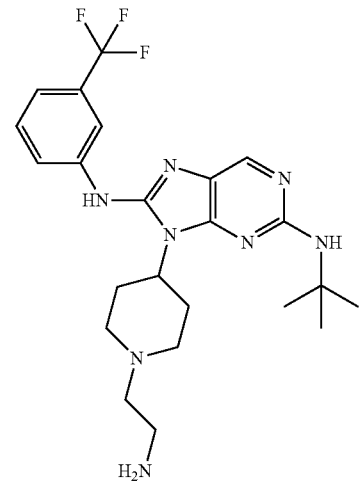 [SMILES: CC(C)(C)Nc1ncc2nc(Nc3cccc(C(F)(F)F)c3)n(C3CCN(CCN)CC3)c2n1] | 9-(1-(2-aminoethyl)piperidin-4-yl)-N2-tert-butyl-N8-(3-(trifluoromethyl)phenyl)-9H-purine-2,8-diamine | 477.2 | D |

TABLE 1-continued

| Cpd # | Structure | Cmdp Name | MH+ | Act Class |
|---|---|---|---|---|
| 5 | 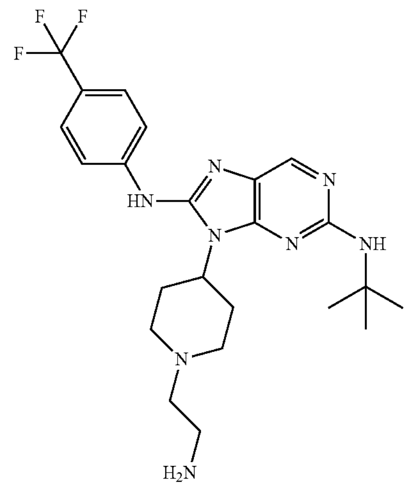 [SMILES: CC(C)(C)Nc1ncc2nc(Nc3ccc(C(F)(F)F)cc3)n(C3CCN(CCN)CC3)c2n1] | 9-(1-(2-aminoethyl)piperidin-4-yl)-N2-tert-butyl-N8-(4-(trifluoromethyl)phenyl)-9H-purine-2,8-diamine | 477.2 | C |
| 6 | 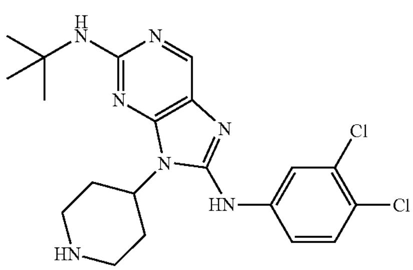 [SMILES: CC(C)(C)Nc1ncc2nc(Nc3ccc(Cl)c(Cl)c3)n(C3CCNCC3)c2n1] | N2-tert-butyl-N8-(3,4-dichlorophenyl)-9-(piperidin-4-yl)-9H-purine-2,8-diamine | 434 | D |
| 7 | 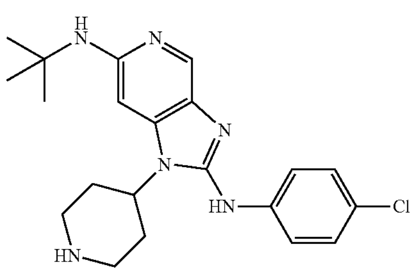 [SMILES: CC(C)(C)Nc1cc2c(cn1)nc(Nc1ccc(Cl)cc1)n2C1CCNCC1] | N2-tert-butyl-N8-(4-chlorophenyl)-9-(piperidin-4-yl)-9H-purine-2,8-diamine | 400 | C |
| 8 | 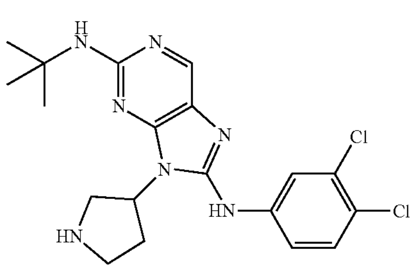 [SMILES: CC(C)(C)Nc1ncc2nc(Nc3ccc(Cl)c(Cl)c3)n(C3CCNC3)c2n1] | N2-tert-butyl-N8-(3,4-dichlorophenyl)-9-(pyrrolidin-3-yl)-9H-purine-2,8-diamine | 420 | C |

TABLE 1-continued

| Cpd # | Structure | Cmdp Name | MH+ | Act Class |
|---|---|---|---|---|
| 9 | 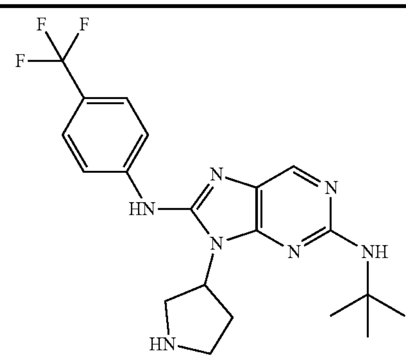 | N2-tert-butyl-9-(pyrrolidin-3-yl)-N8-(4-(trifluoromethyl)phenyl)-9H-purine-2,8-diamine | 420 | B |
| 10 | 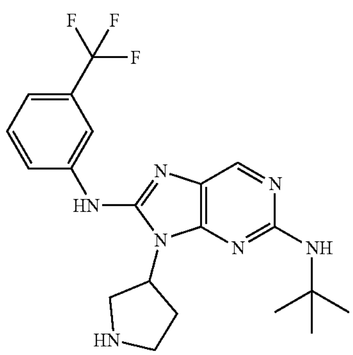 [SMILES: CC(C)(C)Nc1ncc2nc(Nc3cccc(C(F)(F)F)c3)n(C3CCNC3)c2n1] | N2-tert-butyl-9-(pyrrolidin-3-yl)-N8-(3-(trifluoromethyl)phenyl)-9H-purine-2,8-diamine | 420 | C |
| 11 | 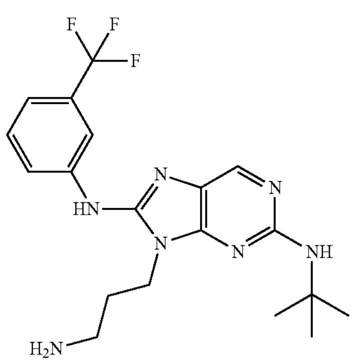 [SMILES: CC(C)(C)Nc1ncc2nc(Nc3cccc(C(F)(F)F)c3)n(CCCN)c2n1] | 9-(3-aminopropyl)-N2-tert-butyl-N8-(3-(trifluoromethyl)phenyl)-9H-purine-2,8-diamine | 408 | B |
| 12 | 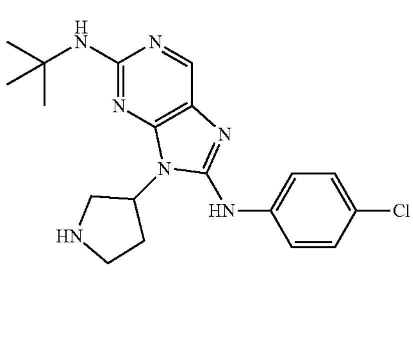 [SMILES: CC(C)(C)Nc1ncc2nc(Nc3ccc(Cl)cc3)n(C3CCNC3)c2n1] | N2-tert-butyl-N8-(4-chlorophenyl)-9-(pyrrolidin-3-yl)-9H-purine-2,8-diamine | 386 | A |

TABLE 1-continued

| Cpd # | Structure | Cmdp Name | MH+ | Act Class |
|---|---|---|---|---|
| 13 | 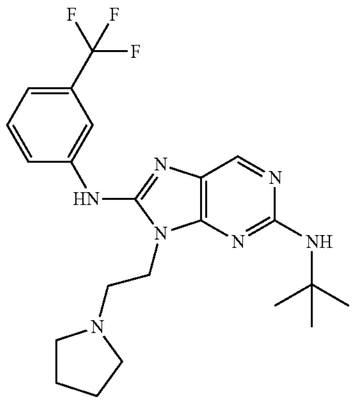 [SMILES: CC(C)(C)Nc1ncc2nc(Nc3cccc(C(F)(F)F)c3)n(CCN3CCCC3)c2n1] | N2-tert-butyl-9-(2-(pyrrolidin-1-yl)ethyl)-N8-(3-(trifluoromethyl)phenyl)-9H-purine-2,8-diamine | 448.2 | A |
| 14 | 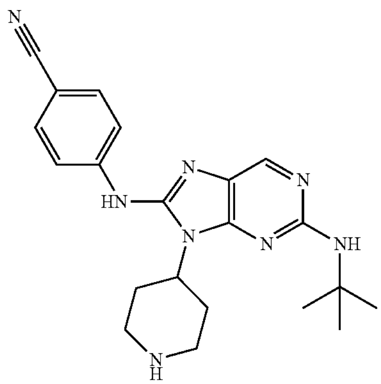 [SMILES: CC(C)(C)Nc1ncc2nc(Nc3ccc(C#N)cc3)n(C3CCNCC3)c2n1] | 4-(2-(tert-butylamino)-9-(piperidin-4-yl)-9H-purin-8-ylamino)benzonitrile | 391.2 | A |
| 15 | 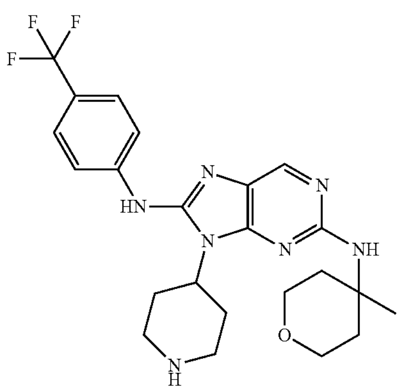 [SMILES: CC1(Nc2ncc3nc(Nc4ccc(C(F)(F)F)cc4)n(C4CCNCC4)c3n2)CCOCC1] | N2-(4-methyltetrahydro-2H-pyran-4-yl)-9-(piperidin-4-yl)-N8-(4-(trifluoromethyl)phenyl)-9H-purine-2,8-diamine | 476.2 | C |
| 16 | 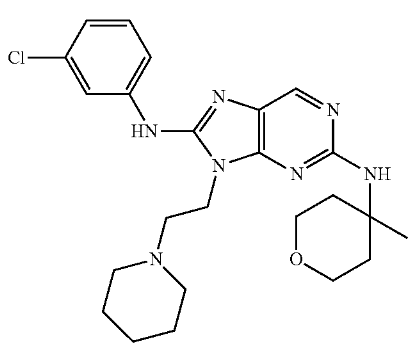 [SMILES: CC1(Nc2ncc3nc(Nc4cccc(Cl)c4)n(CCN4CCCCC4)c3n2)CCOCC1] | N8-(3-chlorophenyl)-N2-(4-methyltetrahydro-2H-pyran-4-yl)-9-(2-(piperidin-1-yl)ethyl)-9H-purine-2,8-diamine | 470.2 | A |

TABLE 1-continued

| Cpd # | Structure | Cmdp Name | MH+ | Act Class |
|---|---|---|---|---|
| 17 | 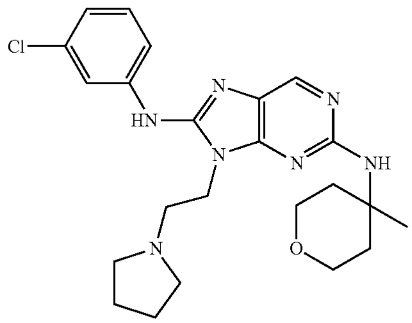 [SMILES: CC1(Nc2ncc3nc(Nc4cccc(Cl)c4)n(CCN4CCCC4)c3n2)CCOCC1] | N8-(3-chlorophenyl)-N2-(4-methyltetrahydro-2H-pyran-4-yl)-9-(2-(pyrrolidin-1-yl)ethyl)-9H-purine-2,8-diamine | 456.2 | A |
| 18 | 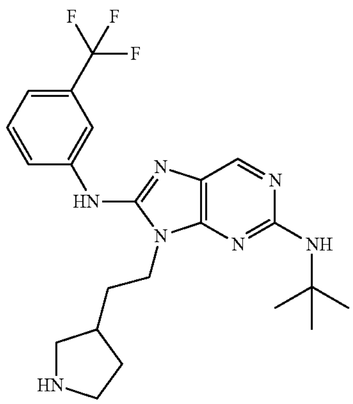 | N2-tert-butyl-9-(2-(pyrrolidin-3-yl)ethyl)-N8-(3-(trifluoromethyl)phenyl)-9H-purine-2,8-diamine | 448.2 | C |
| 19 | 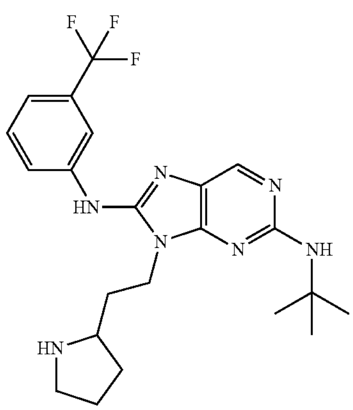 [SMILES: CC(C)(C)Nc1ncc2nc(Nc3cccc(C(F)(F)F)c3)n(CCC3CCCN3)c2n1] | N2-tert-butyl-9-(2-(pyrrolidin-2-yl)ethyl)-N8-(3-(trifluoromethyl)phenyl)-9H-purine-2,8-diamine | 448.2 | B |
| 20 | 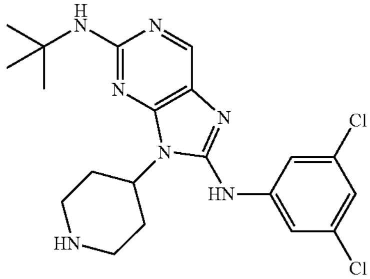 [SMILES: CC(C)(C)Nc1ncc2nc(Nc3cc(Cl)cc(Cl)c3)n(C3CCNCC3)c2n1] | N2-tert-butyl-N8-(3,5-dichlorophenyl)-9-(piperidin-4-yl)-9H-purine-2,8-diamine | 434.2 | D |

TABLE 1-continued

| Cpd # | Structure | Cmdp Name | MH+ | Act Class |
|---|---|---|---|---|
| 21 | 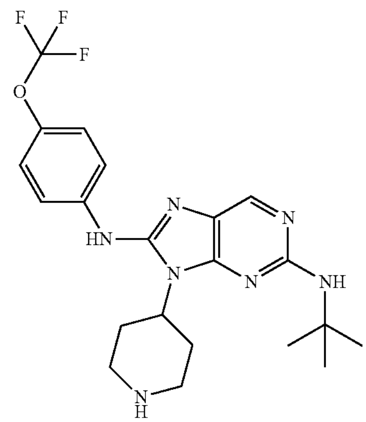 [SMILES: CC(C)(C)Nc1ncc2nc(Nc3ccc(OC(F)(F)F)cc3)n(C3CCNCC3)c2n1] | N2-tert-butyl-9-(piperidin-4-yl)-N8-(4-(trifluoromethoxy)phenyl)-9H-purine-2,8-diamine | 450.2 | C |
| 22 | 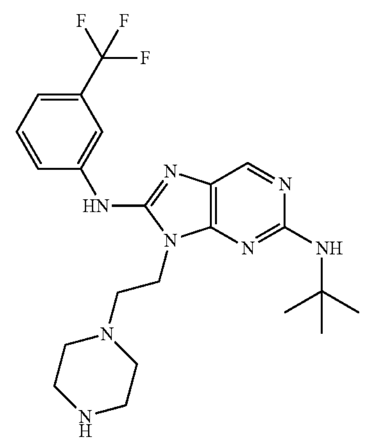 [SMILES: CC(C)(C)Nc1ncc2nc(Nc3cccc(C(F)(F)F)c3)n(CCN3CCNCC3)c2n1] | N2-tert-butyl-9-(2-(piperazin-1-yl)ethyl)-N8-(3-(trifluoromethyl)phenyl)-9H-purine-2,8-diamine | 463.2 | A |
| 23 | 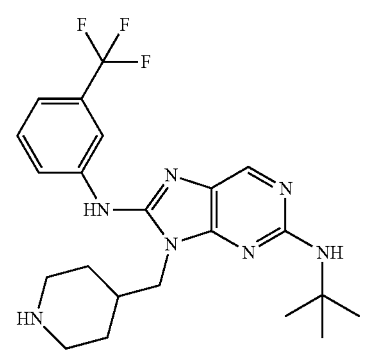 [SMILES: CC(C)(C)Nc1ncc2nc(Nc3cccc(C(F)(F)F)c3)n(CC3CCNCC3)c2n1] | N2-tert-butyl-9-(piperidin-4-ylmethyl)-N8-(3-(trifluoromethyl)phenyl)-9H-purine-2,8-diamine | 448.2 | A |
| 24 | 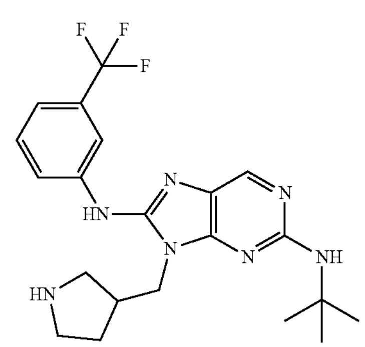 [SMILES: CC(C)(C)Nc1ncc2nc(Nc3cccc(C(F)(F)F)c3)n(CC3CCNC3)c2n1] | N2-tert-butyl-9-(pyrrolidin-3-ylmethyl)-N8-(3-(trifluoromethyl)phenyl)-9H-purine-2,8-diamine | 434.2 | B |

TABLE 1-continued

| Cpd # | Structure | Cmpd Name | MH+ | Act Class |
|---|---|---|---|---|
| 25 | 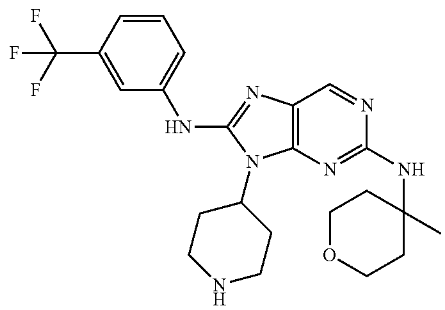 [SMILES: CC1(Nc2ncc3nc(Nc4cccc(C(F)(F)F)c4)n(C4CCNCC4)c3n2)CCOCC1] | N2-(4-methyltetrahydro-2H-pyran-4-yl)-9-(piperidin-4-yl)-N8-(3-(trifluoromethyl)phenyl)-9H-purine-2,8-diamine | 476.2 | A |
| 26 | 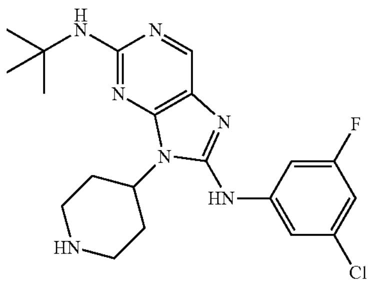 | N2-tert-butyl-N8-(3-chloro-5-fluorophenyl)-9-(piperidin-4-yl)-9H-purine-2,8-diamine | 418.2 | D |
| 27 | 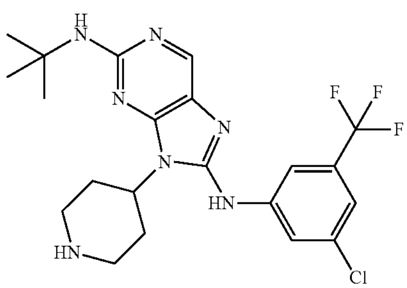 [SMILES: CC(C)(C)Nc1ncc2nc(Nc3cc(Cl)cc(C(F)(F)F)c3)n(C3CCNCC3)c2n1] | N2-tert-butyl-N8-(3-chloro-5-(trifluoromethyl)phenyl)-9-(piperidin-4-yl)-9H-purine-2,8-diamine | 468.2 | D |
| 28 | 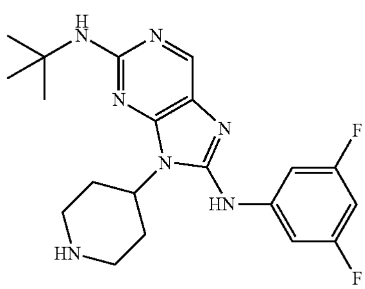 [SMILES: CC(C)(C)Nc1ncc2nc(Nc3cc(F)cc(F)c3)n(C3CCNCC3)c2n1] | N2-tert-butyl-N8-(3,5-difluorophenyl)-9-(piperidin-4-yl)-9H-purine-2,8-diamine | 402.2 | C |
| 29 | 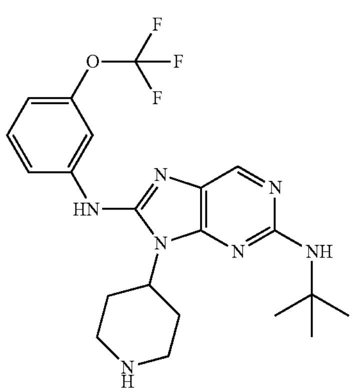 [SMILES: CC(C)(C)Nc1ncc2nc(Nc3cccc(OC(F)(F)F)c3)n(C3CCNCC3)c2n1] | N2-tert-butyl-9-(piperidin-4-yl)-N8-(3-(trifluoromethoxy)phenyl)-9H-purine-2,8-diamine | 450.2 | D |

TABLE 1-continued

| Cpd # | Structure | Cmdp Name | MH+ | Act Class |
|---|---|---|---|---|
| 30 | 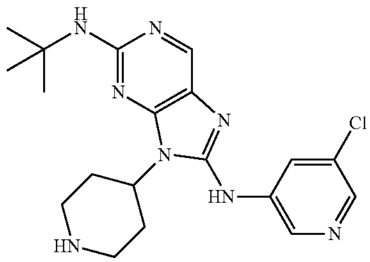 [SMILES: CC(C)(C)Nc1ncc2nc(Nc3cncc(Cl)c3)n(C3CCNCC3)c2n1] | N2-tert-butyl-N8-(5-chloropyridin-3-yl)-9-(piperidin-4-yl)-9H-purine-2,8-diamine | 401.2 | A |
| 31 | 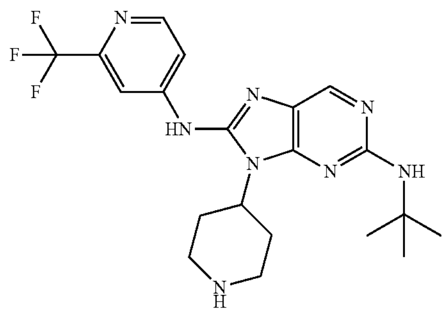 [SMILES: CC(C)(C)Nc1ncc2nc(Nc3ccnc(C(F)(F)F)c3)n(C3CCNCC3)c2n1] | N2-tert-butyl-9-(piperidin-4-yl)-N8-(2-(trifluoromethyl)pyridin-4-yl)-9H-purine-2,8-diamine | 435.2 | B |
| 32 | 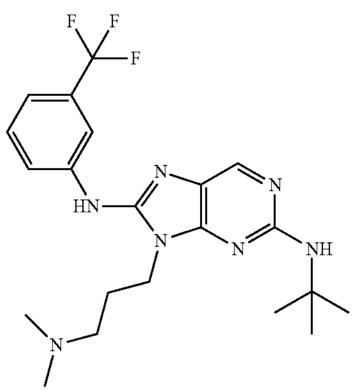 [SMILES: CN(C)CCCn1c(Nc2cccc(C(F)(F)F)c2)nc2cnc(NC(C)(C)C)nc21] | N2-tert-butyl-9-(3-(dimethylamino)propyl)-N8-(3-(trifluoromethyl)phenyl)-9H-purine-2,8-diamine | 436.2 | A |
| 33 | 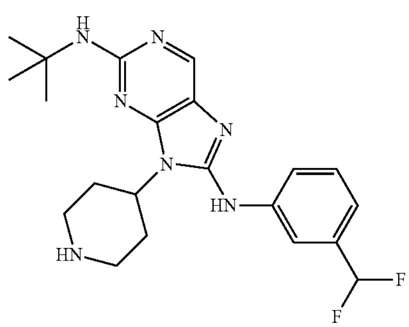 [SMILES: CC(C)(C)Nc1ncc2nc(Nc3cccc(C(F)F)c3)n(C3CCNCC3)c2n1] | N2-tert-butyl-N8-(3-(difluoromethyl)phenyl)-9-(piperidin-4-yl)-9H-purine-2,8-diamine | 416.2 | B |
| 34 | 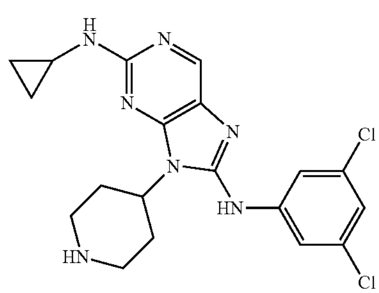 [SMILES: Clc1cc(Cl)cc(Nc2nc3cnc(NC4CC4)nc3n2C2CCNCC2)c1] | N2-cyclopropyl-N8-(3,5-dichlorophenyl)-9-(piperidin-4-yl)-9H-purine-2,8-diamine | 418.2 | B |

TABLE 1-continued

| Cpd # | Structure | Cmdp Name | MH+ | Act Class |
|---|---|---|---|---|
| 35 | 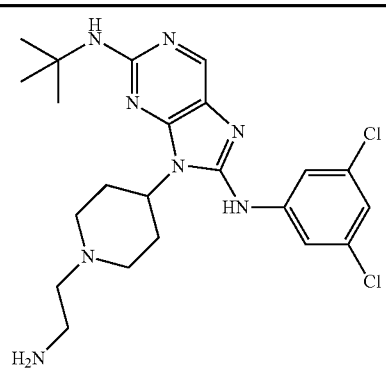 | 9-(1-(2-aminoethyl)piperidin-4-yl)-N2-tert-butyl-N8-(3,5-dichlorophenyl)-9H-purine-2,8-diamine | 477.2 | B |
| 36 | 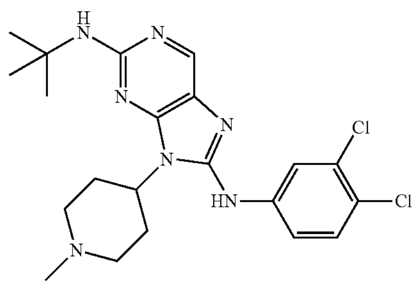 [SMILES: CN1CCC(n2c(Nc3ccc(Cl)c(Cl)c3)nc3cnc(NC(C)(C)C)nc32)CC1] | N2-tert-butyl-N8-(3,4-dichlorophenyl)-9-(1-methylpiperidin-4-yl)-9H-purine-2,8-diamine | 448.2 | D |
| 37 | 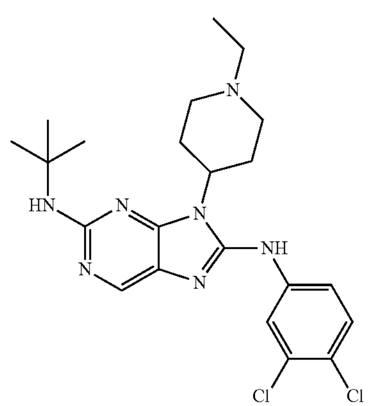 [SMILES: CCN1CCC(n2c(Nc3ccc(Cl)c(Cl)c3)nc3cnc(NC(C)(C)C)nc32)CC1] | N2-tert-butyl-N8-(3,4-dichlorophenyl)-9-(1-ethylpiperidin-4-yl)-9H-purine-2,8-diamine | 462.2 | D |
| 38 | 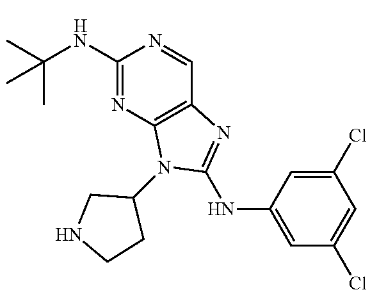 [SMILES: CC(C)(C)Nc1ncc2nc(Nc3cc(Cl)cc(Cl)c3)n(C3CCNC3)c2n1] | N2-tert-butyl-N8-(3,5-dichlorophenyl)-9-(pyrrolidin-3-yl)-9H-purine-2,8-diamine | 420.2 | C |

TABLE 1-continued

| Cpd # | Structure | Cmdp Name | MH+ | Act Class |
|---|---|---|---|---|
| 39 | 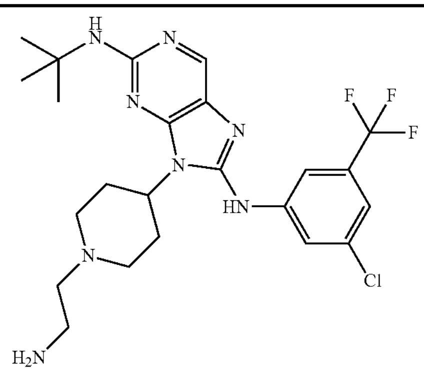 | 9-(1-(2-aminoethyl)piperidin-4-yl)-N2-tert-butyl-N8-(3-chloro-5-(trifluoromethyl)phenyl)-9H-purine-2,8-diamine | 511.2 | D |
| 40 | 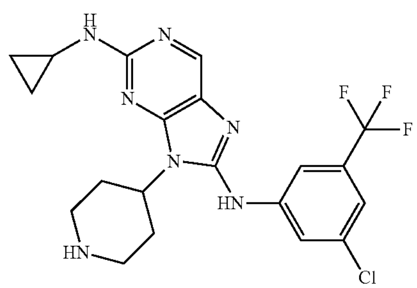 [SMILES: FC(F)(F)c1cc(Cl)cc(Nc2nc3cnc(NC4CC4)nc3n2C2CCNCC2)c1] | N8-(3-chloro-5-(trifluoromethyl)phenyl)-N2-cyclopropyl-9-(piperidin-4-yl)-9H-purine-2,8-diamine | 452.2 | D |
| 41 | 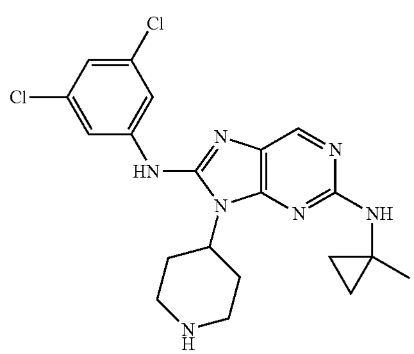 [SMILES: CC1(Nc2ncc3nc(Nc4cc(Cl)cc(Cl)c4)n(C4CCNCC4)c3n2)CC1] | N8-(3,5-dichlorophenyl)-N2-(1-methylcyclopropyl)-9-(piperidin-4-yl)-9H-purine-2,8-diamine | 432.2 | D |
| 42 | 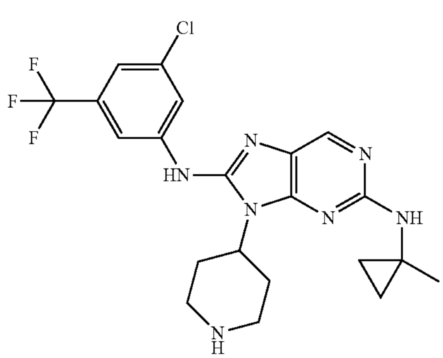 [SMILES: CC1(Nc2ncc3nc(Nc4cc(Cl)cc(C(F)(F)F)c4)n(C4CCNCC4)c3n2)CC1] | N8-(3-chloro-5-(trifluoromethyl)phenyl)-N2-(1-methylcyclopropyl)-9-(piperidin-4-yl)-9H-purine-2,8-diamine | 466.2 | D |

TABLE 1-continued

| Cpd # | Structure | Cmpd Name | MH+ | Act Class |
|---|---|---|---|---|
| 43 | 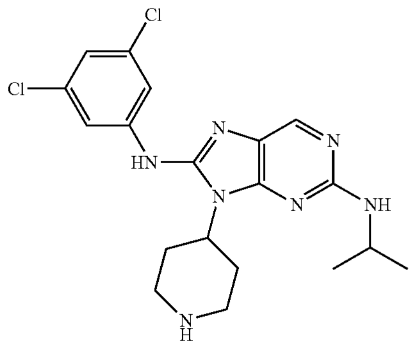 [SMILES: CC(C)Nc1ncc2nc(Nc3cc(Cl)cc(Cl)c3)n(C3CCNCC3)c2n1] | N8-(3,5-dichlorophenyl)-N2-isopropyl-9-(piperidin-4-yl)-9H-purine-2,8-diamine | 420.2 | D |
| 44 | 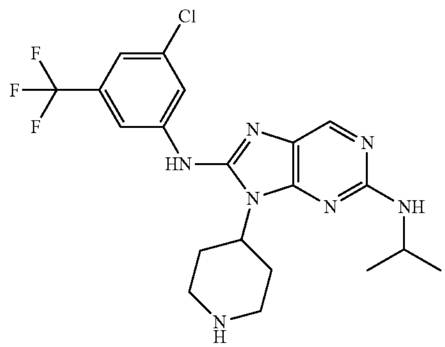 [SMILES: CC(C)Nc1ncc2nc(Nc3cc(Cl)cc(C(F)(F)F)c3)n(C3CCNCC3)c2n1] | N8-(3-chloro-5-(trifluoromethyl)phenyl)-N2-isopropyl-9-(piperidin-4-yl)-9H-purine-2,8-diamine | 454.2 | D |
| 45 | 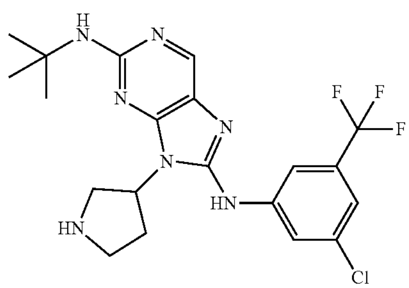 [SMILES: CC(C)(C)Nc1ncc2nc(Nc3cc(Cl)cc(C(F)(F)F)c3)n(C3CCNC3)c2n1] | N2-tert-butyl-N8-(3-chloro-5-(trifluoromethyl)phenyl)-9-(pyrrolidin-3-yl)-9H-purine-2,8-diamine | 454.2 | D |
| 46 | 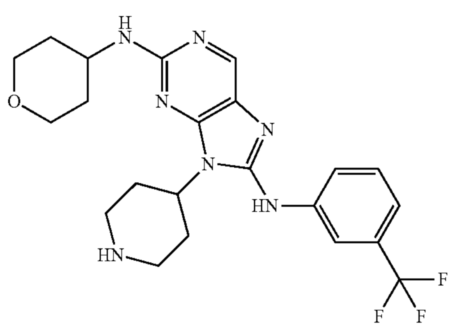 [SMILES: FC(F)(F)c1cccc(Nc2nc3cnc(NC4CCOCC4)nc3n2C2CCNCC2)c1] | 9-(piperidin-4-yl)-N2-(tetrahydro-2H-pyran-4-yl)-N8-(3-(trifluoromethyl)phenyl)-9H-purine-2,8-diamine | 462.2 | A |
| 47 | 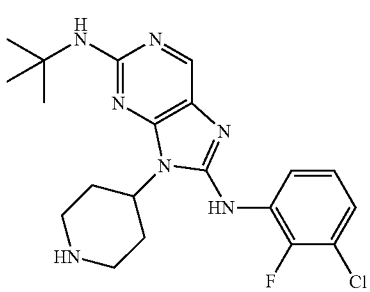 [SMILES: CC(C)(C)Nc1ncc2nc(Nc3cccc(Cl)c3F)n(C3CCNCC3)c2n1] | N2-tert-butyl-N8-(3-chloro-2-fluorophenyl)-9-(piperidin-4-yl)-9H-purine-2,8-diamine | 418.2 | A |

TABLE 1-continued

| Cpd # | Structure | Cmdp Name | MH+ | Act Class |
|---|---|---|---|---|
| 48 | 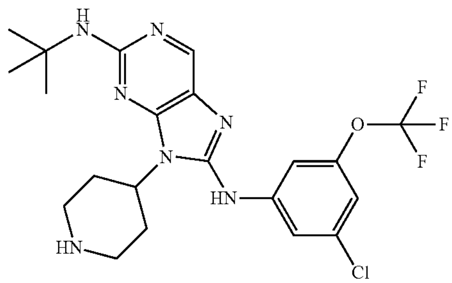 [SMILES: CC(C)(C)Nc1ncc2nc(Nc3cc(Cl)cc(OC(F)(F)F)c3)n(C3CCNCC3)c2n1] | N2-tert-butyl-N8-(3-chloro-5-(trifluoromethoxy)phenyl)-9-(piperidin-4-yl)-9H-purine-2,8-diamine | 484.2 | D |
| 49 | 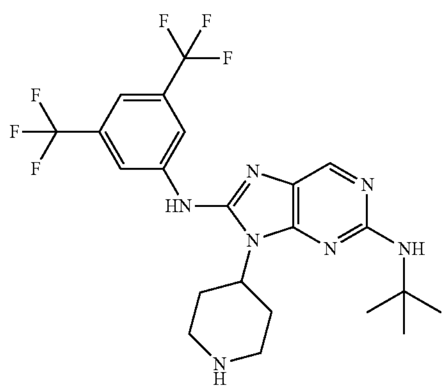 [SMILES: CC(C)(C)Nc1ncc2nc(Nc3cc(C(F)(F)F)cc(C(F)(F)F)c3)n(C3CCNCC3)c2n1] | N8-(3,5-bis(trifluoromethyl)phenyl)-N2-tert-butyl-9-(piperidin-4-yl)-9H-purine-2,8-diamine | 502.2 | D |
| 50 | 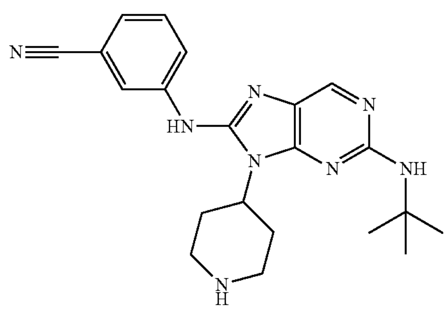 [SMILES: CC(C)(C)Nc1ncc2nc(Nc3cccc(C#N)c3)n(C3CCNCC3)c2n1] | 3-(2-(tert-butylamino)-9-(piperidin-4-yl)-9H-purin-8-ylamino)benzonitrile | 390.2 | B |
| 51 | 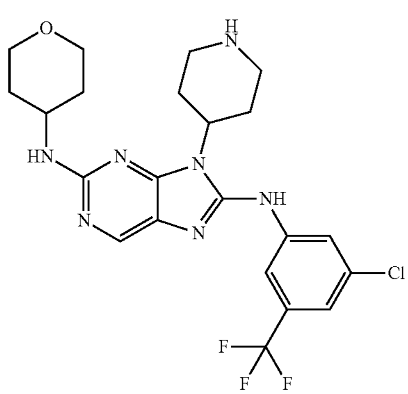 [SMILES: FC(F)(F)c1cc(Cl)cc(Nc2nc3cnc(NC4CCOCC4)nc3n2C2CCNCC2)c1] | N8-(3-chloro-5-(trifluoromethyl)phenyl)-9-(piperidin-4-yl)-N2-(tetrahydro-2H-pyran-4-yl)-9H-purine-2,8-diamine | 496.2 | C |

TABLE 1-continued

| Cpd # | Structure | Cmdp Name | MH+ | Act Class |
|---|---|---|---|---|
| 52 | 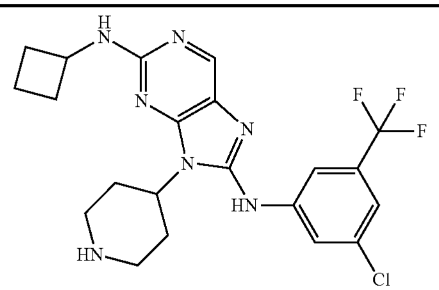 | N8-(3-chloro-5-(trifluoromethyl)phenyl)-N2-cyclobutyl-9-(piperidin-4-yl)-9H-purine-2,8-diamine | 466.2 | D |
| 53 | 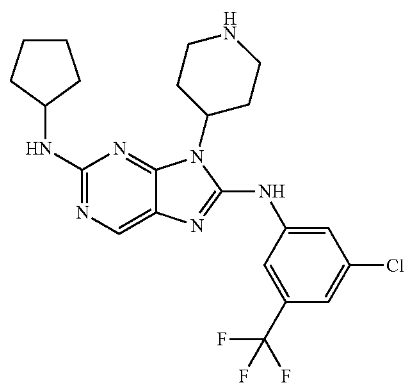 [SMILES: FC(F)(F)c1cc(Cl)cc(Nc2nc3cnc(NC4CCCC4)nc3n2C2CCNCC2)c1] | N8-(3-chloro-5-(trifluoromethyl)phenyl)-N2-cyclopentyl-9-(piperidin-4-yl)-9H-purine-2,8-diamine | 480.2 | D |
| 54 | 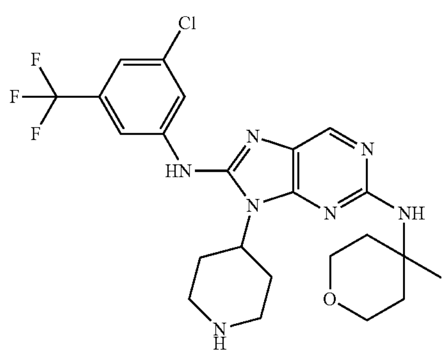 [SMILES: CC1(Nc2ncc3nc(Nc4cc(Cl)cc(C(F)(F)F)c4)n(C4CCNCC4)c3n2)CCOCC1] | N8-(3-chloro-5-(trifluoromethyl)phenyl)-N2-(4-methyltetrahydro-2H-pyran-4-yl)-9-(piperidin-4-yl)-9H-purine-2,8-diamine | 510.2 | D |
| 55 | 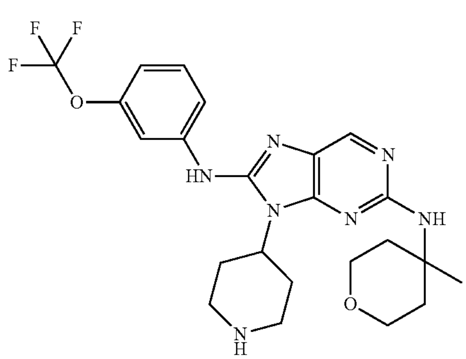 [SMILES: CC1(Nc2ncc3nc(Nc4cccc(OC(F)(F)F)c4)n(C4CCNCC4)c3n2)CCOCC1] | N2-(4-methyltetrahydro-2H-pyran-4-yl)-9-(piperidin-4-yl)-N8-(3-(trifluoromethoxy)phenyl)-9H-purine-2,8-diamine | 492.2 | C |

TABLE 1-continued

| Cpd # | Structure | Cmdp Name | MH+ | Act Class |
|---|---|---|---|---|
| 56 | 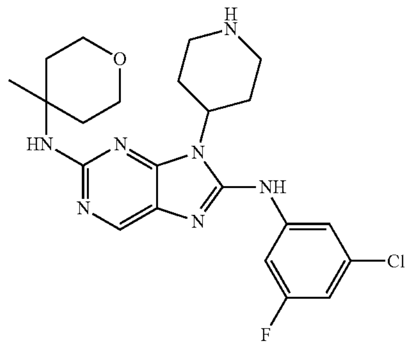 [SMILES: CC1(Nc2ncc3nc(Nc4cc(F)cc(Cl)c4)n(C4CCNCC4)c3n2)CCOCC1] | N8-(3-chloro-5-fluorophenyl)-N2-(4-methyltetrahydro-2H-pyran-4-yl)-9-(piperidin-4-yl)-9H-purine-2,8-diamine | 460.2 | D |
| 57 | 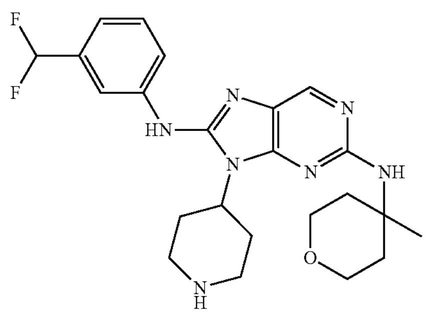 [SMILES: CC1(Nc2ncc3nc(Nc4cccc(C(F)F)c4)n(C4CCNCC4)c3n2)CCOCC1] | N8-(3-(difluoromethyl)phenyl)-N2-(4-methyltetrahydro-2H-pyran-4-yl)-9-(piperidin-4-yl)-9H-purine-2,8-diamine | 458.2 | A |
| 58 | 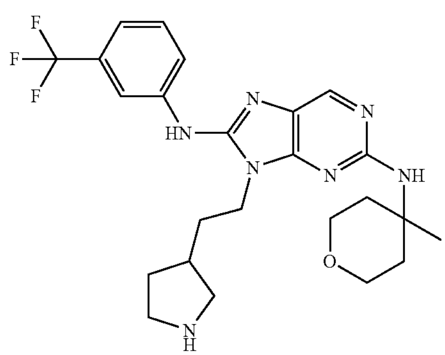 [SMILES: CC1(Nc2ncc3nc(Nc4cccc(C(F)(F)F)c4)n(CCC4CCNC4)c3n2)CCOCC1] | N2-(4-methyltetrahydro-2H-pyran-4-yl)-9-(2-(pyrrolidin-3-yl)ethyl)-N8-(3-(trifluoromethyl)phenyl)-9H-purine-2,8-diamine | 490.4 | B |
| 59 | 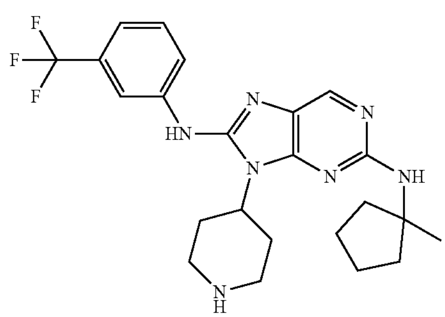 [SMILES: CC1(Nc2ncc3nc(Nc4cccc(C(F)(F)F)c4)n(C4CCNCC4)c3n2)CCCC1] | N2-(1-methylcyclopentyl)-9-(piperidin-4-yl)-N8-(3-(trifluoromethyl)phenyl)-9H-purine-2,8-diamine | 460.2 | D |

TABLE 1-continued
| Cpd # | Structure | Cmdp Name | MH+ | Act Class |
|---|---|---|---|---|
| 60 | 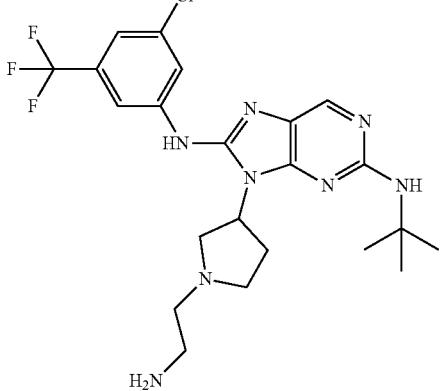 | 9-(1-(2-aminoethyl)pyrrolidin-3-yl)-N2-tert-butyl-N8-(3-chloro-5-(trifluoromethyl)phenyl)-9H-purine-2,8-diamine | 497.2 | B |
| 61 | 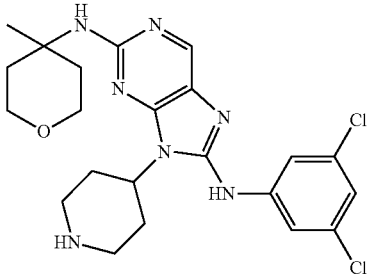 [SMILES: CC1(Nc2ncc3nc(Nc4cc(Cl)cc(Cl)c4)n(C4CCNCC4)c3n2)CCOCC1] | N8-(3,5-dichlorophenyl)-N2-(4-methyltetrahydro-2H-pyran-4-yl)-9-(piperidin-4-yl)-9H-purine-2,8-diamine | 476.2 | D |
| 62 | 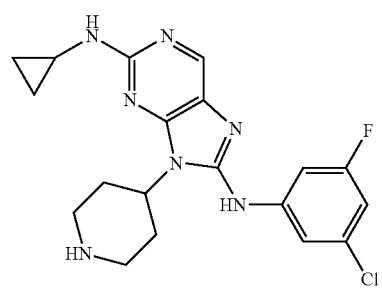 [SMILES: Fc1cc(Cl)cc(Nc2nc3cnc(NC4CC4)nc3n2C2CCNCC2)c1] | N8-(3-chloro-5-fluorophenyl)-N2-cyclopropyl-9-(piperidin-4-yl)-9H-purine-2,8-diamine | 402.2 | C |
| 63 | 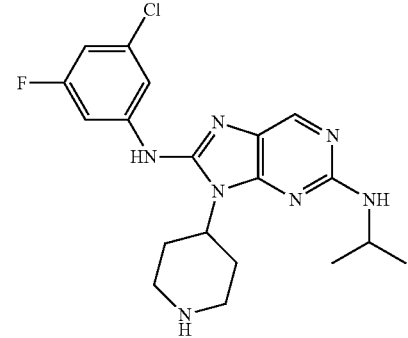 [SMILES: CC(C)Nc1ncc2nc(Nc3cc(F)cc(Cl)c3)n(C3CCNCC3)c2n1] | N8-(3-chloro-5-fluorophenyl)-N2-isopropyl-9-(piperidin-4-yl)-9H-purine-2,8-diamine | 404.2 | D |

TABLE 1-continued

| Cpd # | Structure | Cmdp Name | MH+ | Act Class |
|---|---|---|---|---|
| 64 | 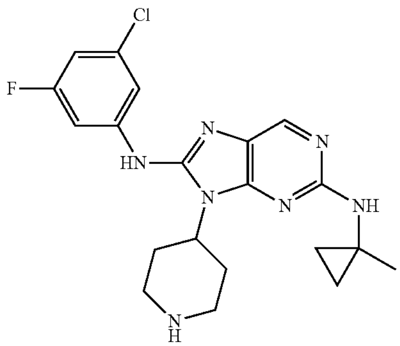 [SMILES: CC1(Nc2ncc3nc(Nc4cc(F)cc(Cl)c4)n(C4CCNCC4)c3n2)CC1] | N8-(3-chloro-5-fluorophenyl)-N2-(1-methylcyclopropyl)-9-(piperidin-4-yl)-9H-purine-2,8-diamine | 416.2 | D |
| 65 | 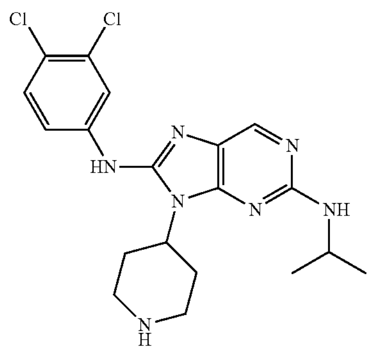 [SMILES: CC(C)Nc1ncc2nc(Nc3ccc(Cl)c(Cl)c3)n(C3CCNCC3)c2n1] | N8-(3,4-dichlorophenyl)-N2-isopropyl-9-(piperidin-4-yl)-9H-purine-2,8-diamine | 420.2 | D |
| 66 | 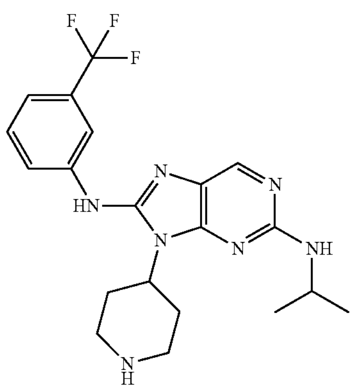 [SMILES: CC(C)Nc1ncc2nc(Nc3cccc(C(F)(F)F)c3)n(C3CCNCC3)c2n1] | N2-isopropyl-9-(piperidin-4-yl)-N8-(3-(trifluoromethyl)phenyl)-9H-purine-2,8-diamine | 420.2 | C |
| 67 | 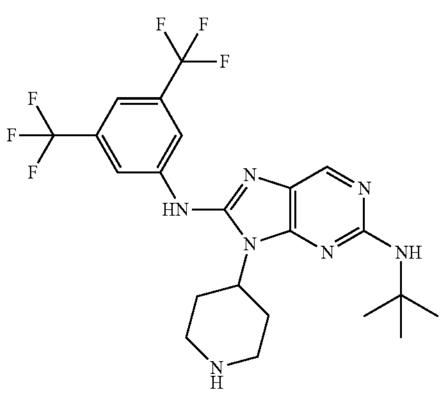 [SMILES: CC(C)(C)Nc1ncc2nc(Nc3cc(C(F)(F)F)cc(C(F)(F)F)c3)n(C3CCNCC3)c2n1] | N8-(3,5-bis(trifluoromethyl)phenyl)-N2-tert-butyl-9-(piperidin-4-yl)-9H-purine-2,8-diamine | 502.2 | D |

TABLE 1-continued

| Cpd # | Structure | Cmpd Name | MH+ | Act Class |
|---|---|---|---|---|
| 68 | 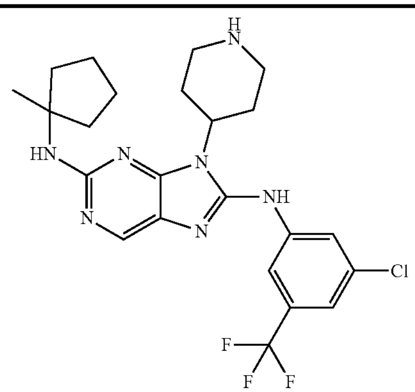 | N8-(3-chloro-5-(trifluoromethyl)phenyl)-N2-(1-methylcyclopentyl)-9-(piperidin-4-yl)-9H-purine-2,8-diamine | 494.2 | D |
| 69 | 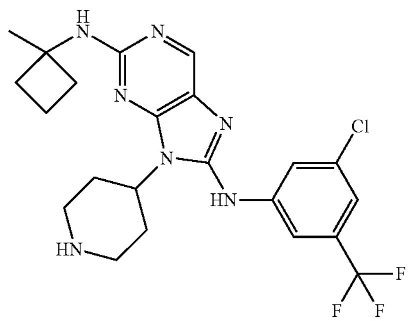 [SMILES: CC1(Nc2ncc3nc(Nc4cc(Cl)cc(C(F)(F)F)c4)n(C4CCNCC4)c3n2)CCC1] | N8-(3-chloro-5-(trifluoromethyl)phenyl)-N2-(1-methylcyclobutyl)-9-(piperidin-4-yl)-9H-purine-2,8-diamine | 480.2 | D |
| 70 | 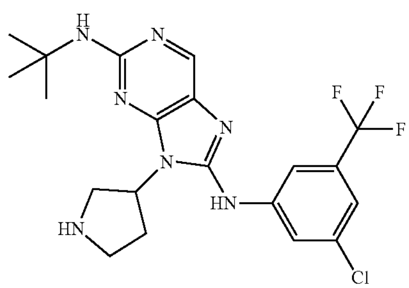 [SMILES: CC(C)(C)Nc1ncc2nc(Nc3cc(Cl)cc(C(F)(F)F)c3)n(C3CCNC3)c2n1] | (S)-N2-tert-butyl-N8-(3-chloro-5-(trifluoromethyl)phenyl)-9-(pyrrolidin-3-yl)-9H-purine-2,8-diamine | 454.2 | C |
| 71 | 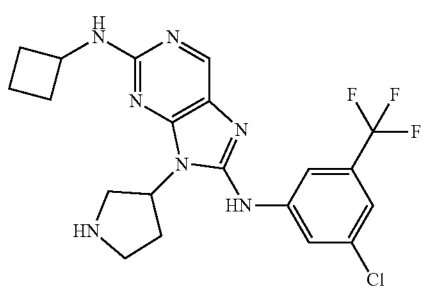 [SMILES: FC(F)(F)c1cc(Cl)cc(Nc2nc3cnc(NC4CCC4)nc3n2C2CCNC2)c1] | N8-(3-chloro-5-(trifluoromethyl)phenyl)-N2-cyclobutyl-9-(pyrrolidin-3-yl)-9H-purine-2,8-diamine | 452.2 | B |
| 72 | 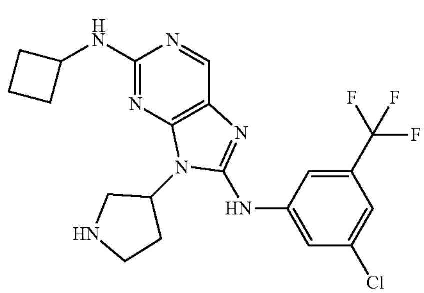 [SMILES: FC(F)(F)c1cc(Cl)cc(Nc2nc3cnc(NC4CCC4)nc3n2C2CCNC2)c1] | N8-(3-chloro-5-(trifluoromethyl)phenyl)-N2-cyclobutyl-9-(pyrrolidin-3-yl)-9H-purine-2,8-diamine | 452.2 | B |

TABLE 1-continued

| Cpd # | Structure | Cmdp Name | MH+ | Act Class |
|---|---|---|---|---|
| 73 | 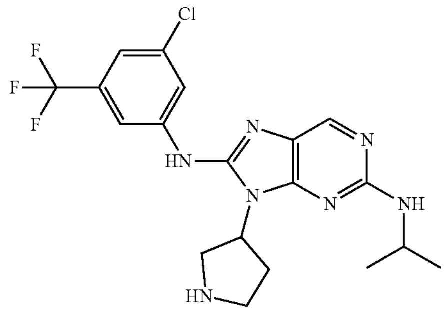 [SMILES: CC(C)Nc1ncc2nc(Nc3cc(Cl)cc(C(F)(F)F)c3)n(C3CCNC3)c2n1] | N8-(3-chloro-5-(trifluoromethyl)phenyl)-N2-isopropyl-9-(pyrrolidin-3-yl)-9H-purine-2,8-8-diamine | 440.2 | B |
| 74 | 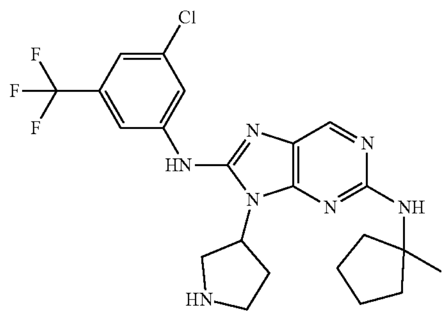 [SMILES: CC1(Nc2ncc3nc(Nc4cc(Cl)cc(C(F)(F)F)c4)n(C4CCNC4)c3n2)CCCC1] | N8-(3-chloro-5-(trifluoromethyl)phenyl)-N2-(1-methylcyclopentyl)-9-(pyrrolidin-3-yl)-9H-purine-2,8-diamine | 480.2 | C |
| 75 | 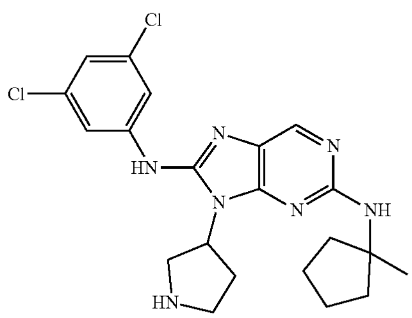 [SMILES: CC1(Nc2ncc3nc(Nc4cc(Cl)cc(Cl)c4)n(C4CCNC4)c3n2)CCCC1] | N8-(3,5-dichlorophenyl)-N2-(1-methylcyclopentyl)-9-(pyrrolidin-3-yl)-9H-purine-2,8-diamine | 447.2 | B |
| 76 | 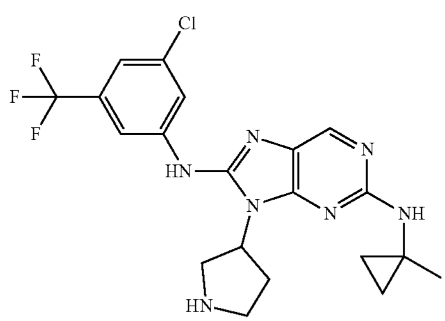 [SMILES: CC1(Nc2ncc3nc(Nc4cc(Cl)cc(C(F)(F)F)c4)n(C4CCNC4)c3n2)CC1] | N8-(3-chloro-5-(trifluoromethyl)phenyl)-N2-(1-methylcyclopropyl)-9-(pyrrolidin-3-yl)-9H-purine-2,8-diamine | 452.2 | C |
| 77 | 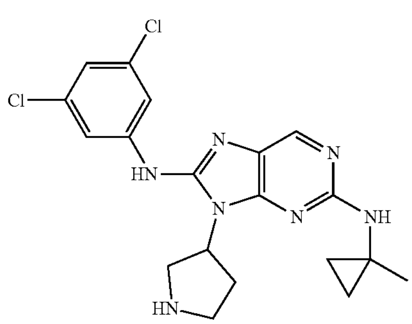 [SMILES: CC1(Nc2ncc3nc(Nc4cc(Cl)cc(Cl)c4)n(C4CCNC4)c3n2)CC1] | N8-(3,5-dichlorophenyl)-N2-(1-methylcyclopropyl)-9-(pyrrolidin-3-yl)-9H-purine-2,8-diamine | 419.2 | B |

TABLE 1-continued

| Cpd # | Structure | Cmdp Name | MH+ | Act Class |
|---|---|---|---|---|
| 78 | 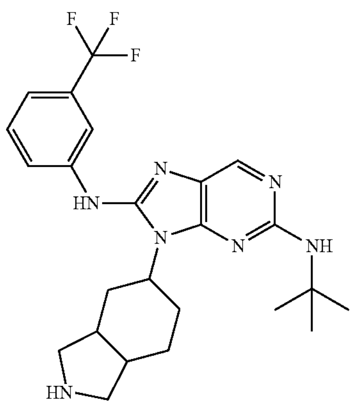 [SMILES: CC(C)(C)Nc1ncc2nc(Nc3cccc(C(F)(F)F)c3)n(C3CCC4CNCC4C3)c2n1] | N2-tert-butyl-9-(octahydro-1H-isoindol-5-yl)-N8-(3-(trifluoromethyl)phenyl)-9H-purine-2,8-diamine | 474.4 | A |
| 79 | 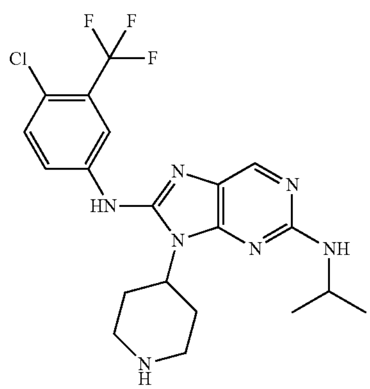 [SMILES: CC(C)Nc1ncc2nc(Nc3ccc(Cl)c(C(F)(F)F)c3)n(C3CCNCC3)c2n1] | N8-(4-chloro-3-(trifluoromethyl)phenyl)-N2-isopropyl-9-(piperidin-4-yl)-9H-purine-2,8-diamine | 454.2 | C |
| 80 | 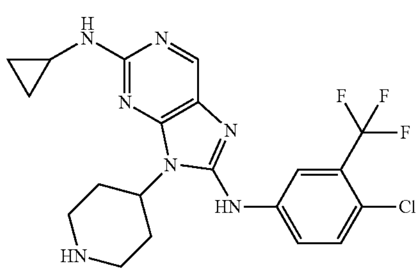 [SMILES: FC(F)(F)c1cc(Nc2nc3cnc(NC4CC4)nc3n2C2CCNCC2)ccc1Cl] | N8-(4-chloro-3-(trifluoromethyl)phenyl)-N2-cyclopropyl-9-(piperidin-4-yl)-9H-purine-2,8-diamine | 452.2 | B |
| 81 | 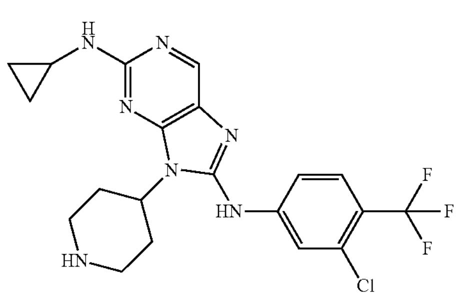 [SMILES: FC(F)(F)c1ccc(Nc2nc3cnc(NC4CC4)nc3n2C2CCNCC2)cc1Cl] | N8-(3-chloro-4-(trifluoromethyl)phenyl)-N2-cyclopropyl-9-(piperidin-4-yl)-9H-purine-2,8-diamine | 452.2 | B |

TABLE 1-continued

| Cpd # | Structure | Cmdp Name | MH+ | Act Class |
|---|---|---|---|---|
| 82 | 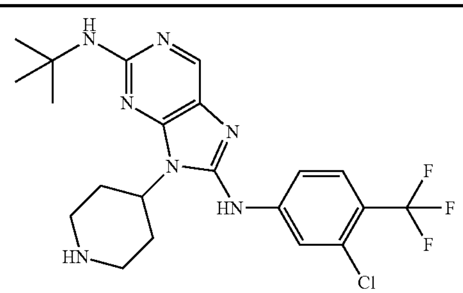 | N2-tert-butyl-N8-(3-chloro-4-(trifluoromethyl)phenyl)-9-(piperidin-4-yl)-9H-purine-2,8-diamine | 468.2 | B |
| 83 | 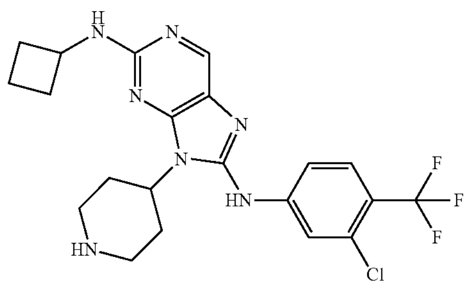 [SMILES: FC(F)(F)c1ccc(Nc2nc3cnc(NC4CCC4)nc3n2C2CCNCC2)cc1Cl] | N8-(3-chloro-4-(trifluoromethyl)phenyl)-N2-cyclobutyl-9-(piperidin-4-yl)-9H-purine-2,8-diamine | 466.2 | C |
| 84 | 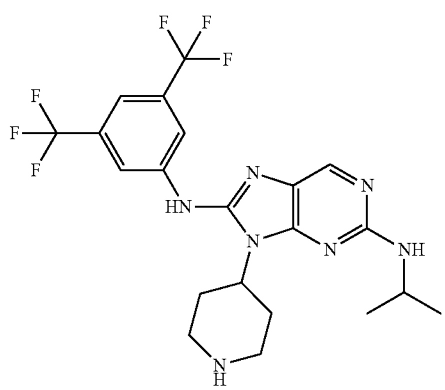 [SMILES: CC(C)Nc1ncc2nc(Nc3cc(C(F)(F)F)cc(C(F)(F)F)c3)n(C3CCNCC3)c2n1] | N8-(3,5-bis(trifluoromethyl)phenyl)-N2-isopropyl-9-(piperidin-4-yl)-9H-purine-2,8-diamine | 488.2 | D |
| 85 | 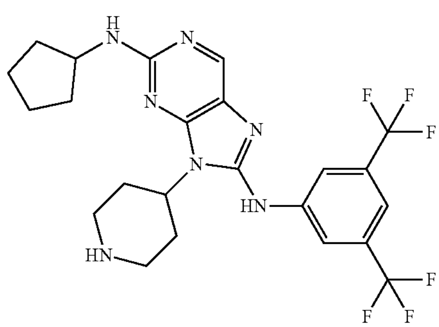 [SMILES: FC(F)(F)c1cc(Nc2nc3cnc(NC4CCCC4)nc3n2C2CCNCC2)cc(C(F)(F)F)c1] | N8-(3,5-bis(trifluoromethyl)phenyl)-N2-cyclopentyl-9-(piperidin-4-yl)-9H-purine-2,8-diamine | 514.2 | D |
| 86 | 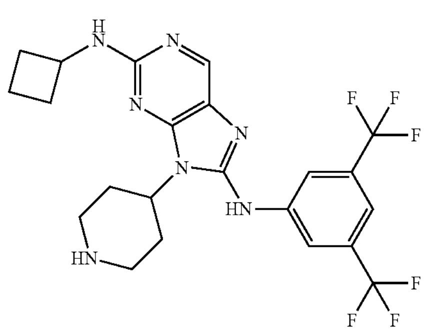 [SMILES: FC(F)(F)c1cc(Nc2nc3cnc(NC4CCC4)nc3n2C2CCNCC2)cc(C(F)(F)F)c1] | N8-(3,5-bis(trifluoromethyl)phenyl)-N2-cyclobutyl-9-(piperidin-4-yl)-9H-purine-2,8-diamine | 500.2 | C |

TABLE 1-continued

| Cpd # | Structure | Cmdp Name | MH+ | Act Class |
|---|---|---|---|---|
| 87 | 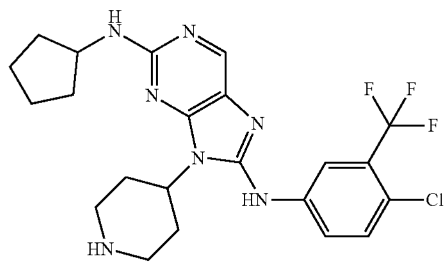 [SMILES: FC(F)(F)c1cc(Nc2nc3cnc(NC4CCCC4)nc3n2C2CCNCC2)ccc1Cl] | N8-(4-chloro-3-(trifluoromethyl)phenyl)-N2-cyclopentyl-9-(piperidin-4-yl)-9H-purine-2,8-diamine | 480.2 | C |
| 88 | 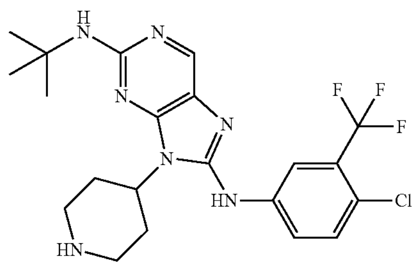 [SMILES: CC(C)(C)Nc1ncc2nc(Nc3ccc(Cl)c(C(F)(F)F)c3)n(C3CCNCC3)c2n1] | N2-tert-butyl-N8-(4-chloro-3-(trifluoromethyl)phenyl)-9-(piperidin-4-yl)-9H-purine-2,8-diamine | 468.2 | C |
| 89 | 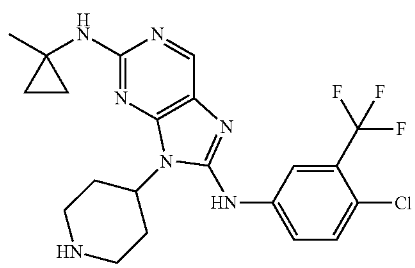 [SMILES: CC1(Nc2ncc3nc(Nc4ccc(Cl)c(C(F)(F)F)c4)n(C4CCNCC4)c3n2)CC1] | N8-(4-chloro-3-(trifluoromethyl)phenyl)-N2-(1-methylcyclopropyl)-9-(piperidin-4-yl)-9H-purine-2,8-diamine | 466.2 | B |
| 90 | 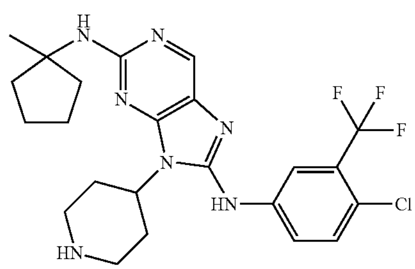 [SMILES: CC1(Nc2ncc3nc(Nc4ccc(Cl)c(C(F)(F)F)c4)n(C4CCNCC4)c3n2)CCCC1] | N8-(4-chloro-3-(trifluoromethyl)phenyl)-N2-(1-methylcyclopentyl)-9-(piperidin-4-yl)-9H-purine-2,8-diamine | 494.2 | C |
| 91 | 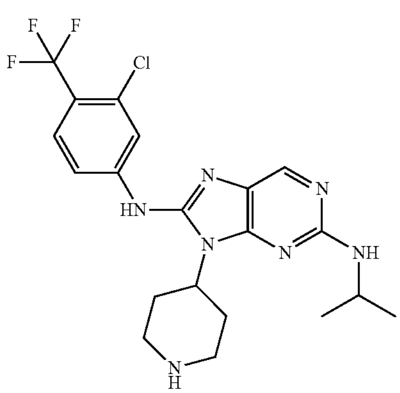 [SMILES: CC(C)Nc1ncc2nc(Nc3ccc(C(F)(F)F)c(Cl)c3)n(C3CCNCC3)c2n1] | N8-(3-chloro-4-(trifluoromethyl)phenyl)-N2-isopropyl-9-(piperidin-4-yl)-9H-purine-2,8-diamine | 454.2 | B |

TABLE 1-continued

| Cpd # | Structure | Cmdp Name | MH+ | Act Class |
|---|---|---|---|---|
| 92 | 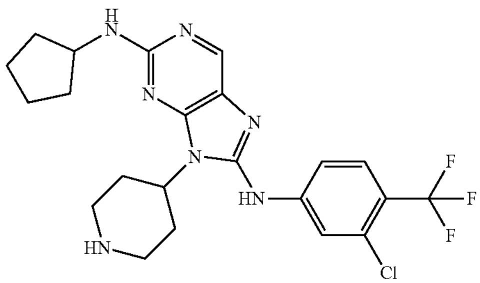 [SMILES: FC(F)(F)c1ccc(Nc2nc3cnc(NC4CCCC4)nc3n2C2CCNCC2)cc1Cl] | N8-(3-chloro-4-(trifluoromethyl)phenyl)-N2-cyclopentyl-9-(piperidin-4-yl)-9H-purine-2,8-diamine | 480.2 | B |
| 93 | 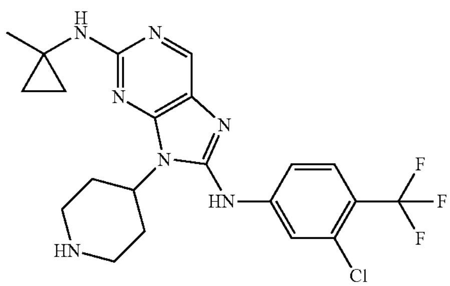 [SMILES: CC1(Nc2ncc3nc(Nc4ccc(C(F)(F)F)c(Cl)c4)n(C4CCNCC4)c3n2)CC1] | N8-(3-chloro-4-(trifluoromethyl)phenyl)-N2-(1-methylcyclopropyl)-9-(piperidin-4-yl)-9H-purine-2,8-diamine | 466.2 | B |
| 94 | 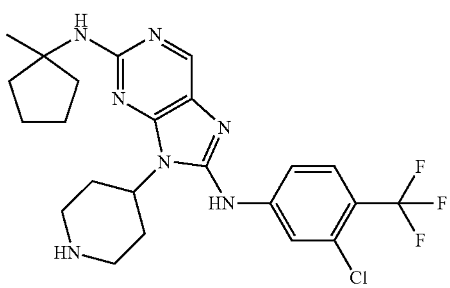 [SMILES: CC1(Nc2ncc3nc(Nc4ccc(C(F)(F)F)c(Cl)c4)n(C4CCNCC4)c3n2)CCCC1] | N8-(3-chloro-4-(trifluoromethyl)phenyl)-N2-(1-methylcyclopentyl)-9-(piperidin-4-yl)-9H-purine-2,8-diamine | 494.2 | C |
| 95 | 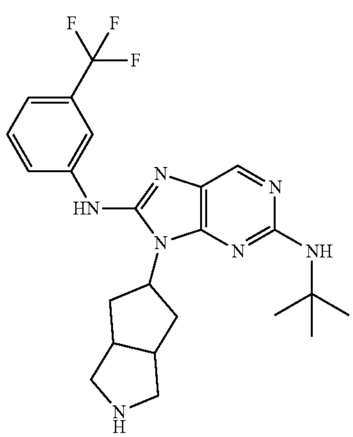 [SMILES: CC(C)(C)Nc1ncc2nc(Nc3cccc(C(F)(F)F)c3)n(C3CC4CNCC4C3)c2n1] | N2-tert-butyl-9-(octahydrocyclopenta[c]pyrrol-5-yl)-N8-(3-(trifluoromethyl)phenyl)-9H-purine-2,8-diamine | 460.2 | B |

TABLE 1-continued

| Cpd # | Structure | Cmdp Name | MH+ | Act Class |
|---|---|---|---|---|
| 96 | 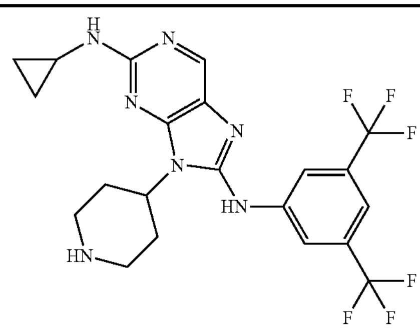 | N8-(3,5-bis(trifluoromethyl)phenyl)-N2-cyclopropyl-9-(piperidin-4-yl)-9H-purine-2,8-diamine | 486.2 | C |
| 97 | 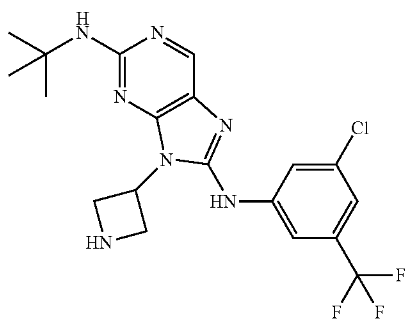 [SMILES: CC(C)(C)Nc1ncc2nc(Nc3cc(Cl)cc(C(F)(F)F)c3)n(C3CNC3)c2n1] | 9-(azetidin-3-yl)-N2-tert-butyl-N8-(3-chloro-5-(trifluoromethyl)phenyl)-9H-purine-2,8-diamine | 440.2 | B |
| 98 | 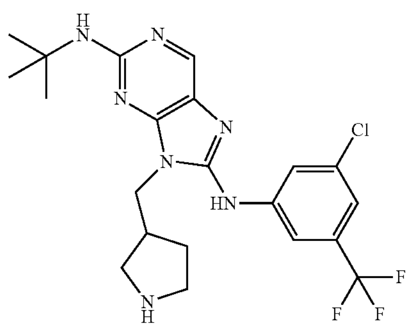 [SMILES: CC(C)(C)Nc1ncc2nc(Nc3cc(Cl)cc(C(F)(F)F)c3)n(CC3CCNC3)c2n1] | N2-tert-butyl-N8-(3-chloro-5-(trifluoromethyl)phenyl)-9-(pyrrolidin-3-ylmethyl)-9H-purine-2,8-diamine | 468.2 | B |
| 99 | 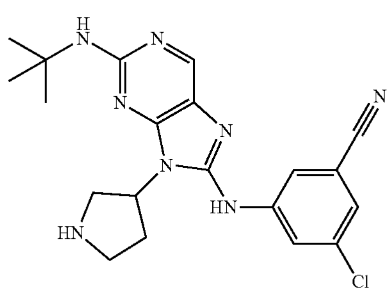 [SMILES: CC(C)(C)Nc1ncc2nc(Nc3cc(Cl)cc(C#N)c3)n(C3CCNC3)c2n1] | 3-(2-(tert-butylamino)-9-(pyrrolidin-3-yl)-9H-purin-8-ylamino)-5-chlorobenzonitrile | 409.2 | B |
| 100 | 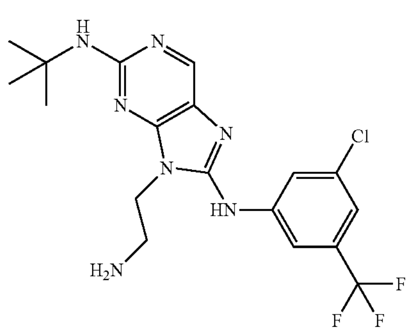 [SMILES: CC(C)(C)Nc1ncc2nc(Nc3cc(Cl)cc(C(F)(F)F)c3)n(CCN)c2n1] | 9-(2-aminoethyl)-N2-tert-butyl-N8-(3-chloro-5-(trifluoromethyl)phenyl)-9H-purine-2,8-diamine | 428.1 | A |

TABLE 1-continued

| Cpd # | Structure | Cmdp Name | MH+ | Act Class |
|---|---|---|---|---|
| 101 | 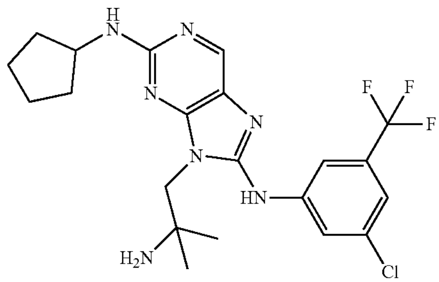 [SMILES: CC(C)(N)Cn1c(Nc2cc(Cl)cc(C(F)(F)F)c2)nc2cnc(NC3CCCC3)nc21] | 9-(2-amino-2-methylpropyl)-N8-(3-chloro-5-(trifluoromethyl)phenyl)-N2-cyclopentyl-9H-purine-2,8-diamine | 468.2 | B |
| 102 | 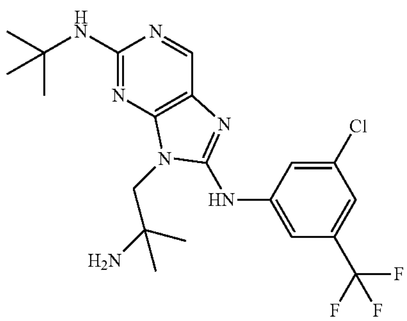 [SMILES: CC(C)(N)Cn1c(Nc2cc(Cl)cc(C(F)(F)F)c2)nc2cnc(NC(C)(C)C)nc21] | 9-(2-amino-2-methylpropyl)-N2-tert-butyl-N8-(3-chloro-5-(trifluoromethyl)phenyl)-9H-purine-2,8-diamine | 456.2 | A |
| 103 | 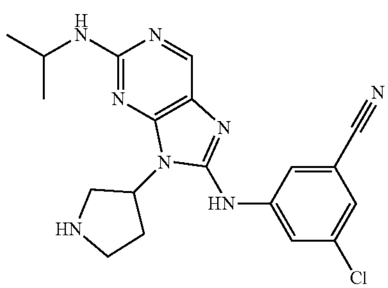 [SMILES: CC(C)Nc1ncc2nc(Nc3cc(Cl)cc(C#N)c3)n(C3CCNC3)c2n1] | 3-chloro-5-(2-(isopropylamino)-9-(pyrrolidin-3-yl)-9H-purin-8-ylamino)benzonitrile | 397.1 | B |
| 104 | 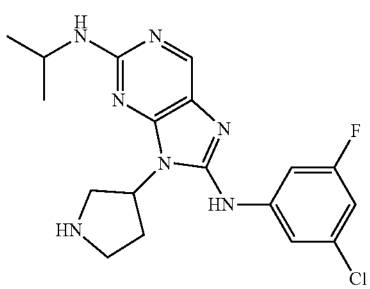 [SMILES: CC(C)Nc1ncc2nc(Nc3cc(F)cc(Cl)c3)n(C3CCNC3)c2n1] | N8-(3-chloro-5-fluorophenyl)-N2-isopropyl-9-(pyrrolidin-3-yl)-9H-purine-2,8-diamine | 390.1 | A |
| 105 | 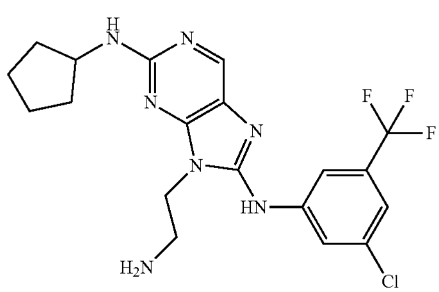 [SMILES: NCCn1c(Nc2cc(Cl)cc(C(F)(F)F)c2)nc2cnc(NC3CCCC3)nc21] | 9-(2-aminoethyl)-N8-(3-chloro-5-(trifluoromethyl)phenyl)-N2-cyclopentyl-9H-purine-2,8-diamine | 440.1 | A |

TABLE 1-continued

| Cpd # | Structure | Cmdp Name | MH+ | Act Class |
|---|---|---|---|---|
| 106 | 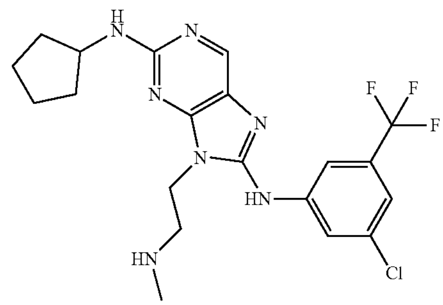 [SMILES: CNCCn1c(Nc2cc(Cl)cc(C(F)(F)F)c2)nc2cnc(NC3CCCC3)nc21] | N8-(3-chloro-5-(trifluoromethyl)phenyl)-N2-cyclopentyl-9-(2-(methylamino)ethyl)-9H-purine-2,8-diamine | 454.1 | B |
| 107 | 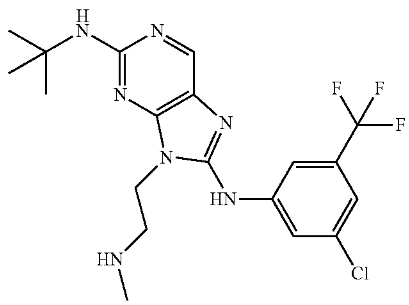 [SMILES: CNCCn1c(Nc2cc(Cl)cc(C(F)(F)F)c2)nc2cnc(NC(C)(C)C)nc21] | N2-tert-butyl-N8-(3-chloro-5-(trifluoromethyl)phenyl)-9-(2-(methylamino)ethyl)-9H-purine-2,8-diamine | 442.2 | A |
| 108 | 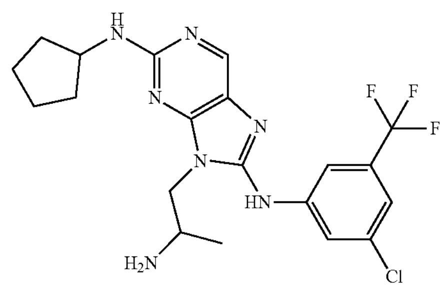 [SMILES: CC(N)Cn1c(Nc2cc(Cl)cc(C(F)(F)F)c2)nc2cnc(NC3CCCC3)nc21] | 9-(2-aminopropyl)-N8-(3-chloro-5-(trifluoromethyl)phenyl)-N2-cyclopentyl-9H-purine-2,8-diamine | 454.1 | B |
| 109 | 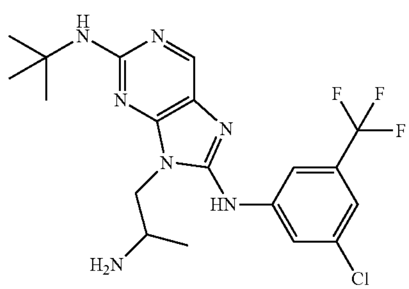 [SMILES: CC(N)Cn1c(Nc2cc(Cl)cc(C(F)(F)F)c2)nc2cnc(NC(C)(C)C)nc21] | 9-(2-aminopropyl)-N2-tert-butyl-N8-(3-chloro-5-(trifluoromethyl)phenyl)-9H-purine-2,8-diamine | 442.1 | A |
| 110 | 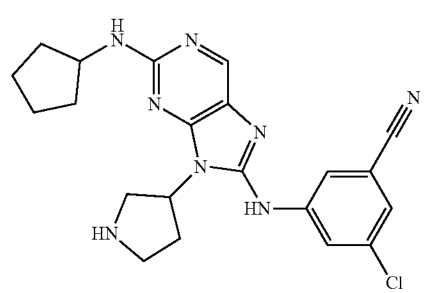 [SMILES: N#Cc1cc(Cl)cc(Nc2nc3cnc(NC4CCCC4)nc3n2C2CCNC2)c1] | 3-chloro-5-(2-(cyclopentylamino)-9-(pyrrolidin-3-yl)-9H-purin-8-ylamino)benzonitrile | 423.1 | A |

TABLE 1-continued

| Cpd # | Structure | Cmdp Name | MH+ | Act Class |
|---|---|---|---|---|
| 111 | 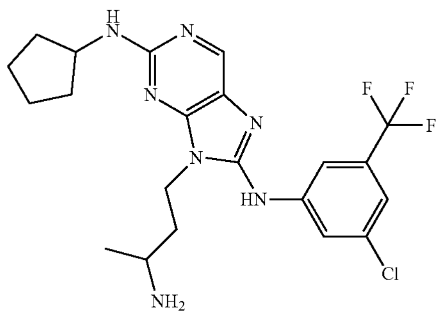 [SMILES: CC(N)CCn1c(Nc2cc(Cl)cc(C(F)(F)F)c2)nc2cnc(NC3CCCC3)nc21] | 9-(3-aminobutyl)-N8-(3-chloro-5-(trifluoromethyl)phenyl)-N2-cyclopentyl-9H-purine-2,8-diamine | 468.2 | C |
| 112 | 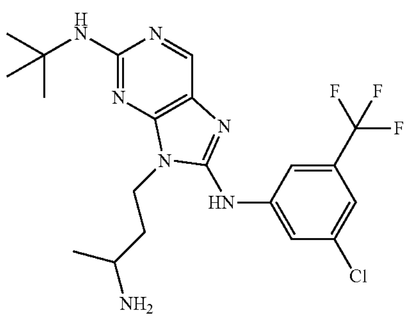 [SMILES: CC(N)CCn1c(Nc2cc(Cl)cc(C(F)(F)F)c2)nc2cnc(NC(C)(C)C)nc21] | 9-(3-aminobutyl)-N2-tert-butyl-N8-(3-chloro-5-(trifluoromethyl)phenyl)-9H-purine-2,8-diamine | 456.1 | B |
| 113 | 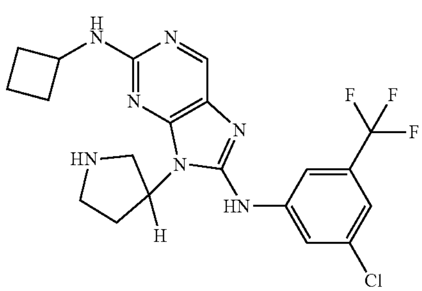 [SMILES: FC(F)(F)c1cc(Cl)cc(Nc2nc3cnc(NC4CCC4)nc3n2C2CCNC2)c1] | (S)-N8-(3-chloro-5-(trifluoromethyl)phenyl)-N2-cyclobutyl-9-(pyrrolidin-3-yl)-9H-purine-2,8-diamine | 452.2 | C |
| 114 | 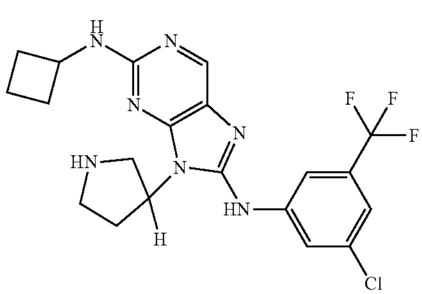 [SMILES: FC(F)(F)c1cc(Cl)cc(Nc2nc3cnc(NC4CCC4)nc3n2C2CCNC2)c1] | (R)-N8-(3-chloro-5-(trifluoromethyl)phenyl)-N2-cyclobutyl-9-(pyrrolidin-3-yl)-9H-purine-2,8-diamine | 452.1 | B |

What is claimed is:

1. A method of treating malaria, comprising administering to a subject having malaria an effective amount of a compound of formula (I),

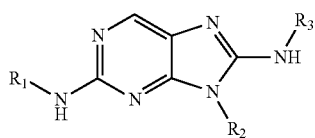

or a pharmaceutically acceptable salt, tautomer, isotopologue, or stereoisomer thereof, wherein
$R^1$ is $CR^{1a}R^{1b}R^{1c}$, wherein $R^{1a}$ and $R^{1b}$ are $(C_{1-4})$alkyl and $R^{1c}$ is H or $(C_{1-4})$alkyl; or $R^{1a}$ and $R^{1b}$ form a 3-6 membered cycloalkyl or 3-6 membered heterocyclyl, and $R^{1c}$ is H or $(C_{1-4})$alkyl;
$R^2$ is L-$R^{2a}$ or L-$R^{2b}$,
L is a bond or $(C_{1-2}$ alkyl);
$R^{2a}$ is 3-6 membered N-containing heterocyclyl or heteroaryl, each optionally substituted with one or more $(C_{1-4})$alkyl, or $(C_{1-4})$alkyl-$NR_2$;
$R^{2b}$ is $(C_{1-4}$ branched or unbranched alkyl)-$NR_2$,
$R^3$ is phenyl or pyridyl, substituted with at least one halogen, CN, $(C_{1-4})$alkyl, or $O(C_{1-4})$alkyl, wherein the alkyl is optionally fluorinated; and
R is H or $(C_{1-4})$ alkyl.

2. The method of claim 1, wherein $R^1$ is $CR^{1a}R^{1b}R^{1c}$, wherein $R^{1a}$ and $R^{1b}$ are $(C_{1-2})$alkyl and $R^{1c}$ is H or $(C_{1-4})$ alkyl.

3. The method of claim 2, wherein $R^1$ is isopropyl or t-butyl.

4. The method of claim 1, wherein $R^1$ is $CR^{1a}R^{1b}R^{1c}$, and $R^{1a}$ and $R^{1b}$ form a 3-6 membered cycloalkyl or 3-6 membered heterocyclyl, and $R^{1c}$ is H or $(C_{1-2})$alkyl.

5. The method of claim 4, wherein $R^{1a}$ and $R^{1b}$ form a cyclopropyl, cyclobutyl, cyclopentyl or tetrahydropyranyl.

6. The method of claim 4, wherein $R^{1c}$ is H or $CH_3$.

7. The method of claim 4, wherein $R^1$ is cyclopropyl, cyclobutyl, cyclopentyl, tetrahydropyranyl, 1-methyl-cyclopropyl, 1-methyl-cyclobutyl, 1-methyl-cylopentyl, 1-methyl-tetrahydropyranyl or 4-methyl-tetrahydropyranyl.

8. The method of claim 1, wherein $R^2$ is L-$R^{2a}$ and $R^{2a}$ is selected from azetidyl, pyrolidinyl, piperidyl, piperazinyl, imidazolyl, octahydrocyclopenta[c]pyrrolyl, or octahydro-1H-isoindolyl.

9. The method of claim 8, wherein L is a bond, —$CH_2$— or —$CH_2CH_2$—.

10. The method of claim 8, wherein $R^2$ is substituted with $CH_3$, $CH_2CH_3$, or $CH_2CH_2NH_2$.

11. The method of claim 8, wherein $R^2$ is azetidyl, piperidyl, pyrrolidyl, octahydrocyclopenta[c]pyrrolyl, octahydro-1H-isoindolyl, $CH_2$-pyrrolidyl, $CH_2CH_2$-pyrrolidyl, $CH_2$-piperidyl, $CH_2CH_2$-piperidyl, $CH_2CH_2$-imidazolyl, or $CH_2CH_2$-piperazinyl.

12. The method of claim 1, wherein $R^2$ is L-$R^{2b}$ and $R^{2b}$ is $CH_2NR_2$, $CH_2CH_2NR_2$, $CH(CH_3)NR_2$, or $C(CH_3)_2NR_2$.

13. The method of claim 12, wherein L is a bond, —$CH_2$— or —$CH_2CH_2$—.

14. The method of claim 12, wherein $R^2$ is $CH_2CH_2NH_2$, $CH_2CH_2NH(CH_3)$, $CH_2CH_2CH_2NH_2$, $CH_2CH_2CH_2N(CH_3)_2$, $CH_2CH(CH_3)NH_2$, or $CH_2C(CH_3)_2NH_2$.

15. The method of claim 1, wherein $R^3$ is phenyl substituted with at least one halogen, CN, fluorinated $(C_{1-2})$alkyl, or O-fluorinated$(C_{1-2})$alkyl.

16. The method of claim 15, wherein $R^3$ is substituted with at least one F, Cl, CN, $CHF_2$, $CF_3$, or $OCF_3$.

17. The method of claim 15, wherein $R^3$ is meta-substituted phenyl.

18. The method of claim 1, wherein $R^3$ is pyridyl, substituted with at least one halogen, fluorinated $(C_{1-2})$alkyl, or O-fluorinated$(C_1\ 2)$alkyl.

19. The method of claim 18, wherein $R^3$ is substituted with at least one Cl, or $CF_3$.

20. The method of claim 1, wherein the compound is:
9-(2-(1H-imidazol-1-yl)ethyl)-N2-tert-butyl-N8-(3-chlorophenyl)-9H-purine-2,8-diamine,
N2-tert-butyl-9-(piperidin-4-yl)-N8-(4-(trifluoromethyl)phenyl)-9H-purine-2,8-diamine,
N2-tert-butyl-9-(piperidin-4-yl)-N8-(3-(trifluoromethyl)phenyl)-9H-purine-2,8-diamine,
9-(1-(2-aminoethyl)piperidin-4-yl)-N2-tert-butyl-N8-(3-(trifluoromethyl)phenyl)-9H-purine-2,8-diamine,
9-(1-(2-aminoethyl)piperidin-4-yl)-N2-tert-butyl-N8-(4-(trifluoromethyl)phenyl)-9H-purine-2,8-diamine,
N2-tert-butyl-N8-(3,4-dichlorophenyl)-9-(piperidin-4-yl)-9H-purine-2,8-diamine,
N2-tert-butyl-N8-(4-chlorophenyl)-9-(piperidin-4-yl)-9H-purine-2,8-diamine,
N2-tert-butyl-N8-(3,4-dichlorophenyl)-9-(pyrrolidin-3-yl)-9H-purine-2,8-diamine,
N2-tert-butyl-9-(pyrrolidin-3-yl)-N8-(4-(trifluoromethyl)phenyl)-9H-purine-2,8-diamine,
N2-tert-butyl-9-(pyrrolidin-3-yl)-N8-(3-(trifluoromethyl)phenyl)-9H-purine-2,8-diamine,
9-(3-aminopropyl)-N2-tert-butyl-N8-(3-(trifluoromethyl)phenyl)-9H-purine-2,8-diamine,
N2-tert-butyl-N8-(4-chlorophenyl)-9-(pyrrolidin-3-yl)-9H-purine-2,8-diamine,
N2-tert-butyl-9-(2-(pyrrolidin-1-yl)ethyl)-N8-(3-(trifluoromethyl)phenyl)-9H-purine-2,8-diamine,
4-(2-(tert-butylamino)-9-(piperidin-4-yl)-9H-purin-8-ylamino)benzonitrile,
N2-(4-methyltetrahydro-2H-pyran-4-yl)-9-(piperidin-4-yl)-N8-(4-(trifluoromethyl)phenyl)-9H-purine-2,8-diamine,
N8-(3-chlorophenyl)-N2-(4-methyltetrahydro-2H-pyran-4-yl)-9-(2-(piperidin-1-yl)ethyl)-9H-purine-2,8-diamine,
N8-(3-chlorophenyl)-N2-(4-methyltetrahydro-2H-pyran-4-yl)-9-(2-(pyrrolidin-1-yl)ethyl)-9H-purine-2,8-diamine,
N2-tert-butyl-9-(2-(pyrrolidin-3-yl)ethyl)-N8-(3-(trifluoromethyl)phenyl)-9H-purine-2,8-diamine,
N2-tert-butyl-9-(2-(pyrrolidin-2-yl)ethyl)-N8-(3-(trifluoromethyl)phenyl)-9H-purine-2,8-diamine,
N2-tert-butyl-N8-(3,5-dichlorophenyl)-9-(piperidin-4-yl)-9H-purine-2,8-diamine,
N2-tert-butyl-9-(piperidin-4-yl)-N8-(4-(trifluoromethoxy)phenyl)-9H-purine-2,8-diamine,
N2-tert-butyl-9-(2-(piperazin-1-yl)ethyl)-N8-(3-(trifluoromethyl)phenyl)-9H-purine-2,8-diamine,
N2-tert-butyl-9-(piperidin-4-ylmethyl)-N8-(3-(trifluoromethyl)phenyl)-9H-purine-2,8-diamine,
N2-tert-butyl-9-(pyrrolidin-3-ylmethyl)-N8-(3-(trifluoromethyl)phenyl)-9H-purine-2,8-diamine,
N2-(4-methyltetrahydro-2H-pyran-4-yl)-9-(piperidin-4-yl)-N8-(3-(trifluoromethyl)phenyl)-9H-purine-2,8-diamine, N2-tert-butyl-N8-(3-chloro-5-fluorophenyl)-9-(piperidin-4-yl)-9H-purine-2,8-diamine,
N2-tert-butyl-N8-(3-chloro-5-(trifluoromethyl)phenyl)-9-(piperidin-4-yl)-9H-purine-2,8-diamine,
N2-tert-butyl-N8-(3,5-difluorophenyl)-9-(piperidin-4-yl)-9H-purine-2,8-diamine,
N2-tert-butyl-9-(piperidin-4-yl)-N8-(3-(trifluoromethoxy)phenyl)-9H-purine-2,8-diamine,
N2-tert-butyl-N8-(5-chloropyridin-3-yl)-9-(piperidin-4-yl)-9H-purine-2,8-diamine,
N2-tert-butyl-9-(piperidin-4-yl)-N8-(2-(trifluoromethyl)pyridin-4-yl)-9H-purine-2,8-diamine,
N2-tert-butyl-9-(3-(dimethylamino)propyl)-N8-(3-(trifluoromethyl)phenyl)-9H-purine-2,8-diamine,
N2-tert-butyl-N8-(3-(difluoromethyl)phenyl)-9-(piperidin-4-yl)-9H-purine-2,8-diamine,
N2-cyclopropyl-N8-(3,5-dichlorophenyl)-9-(piperidin-4-yl)-9H-purine-2,8-diamine,
9-(1-(2-aminoethyl)piperidin-4-yl)-N2-tert-butyl-N8-(3,5-dichlorophenyl)-9H-purine-2,8-diamine,
N2-tert-butyl-N8-(3,4-dichlorophenyl)-9-(1-methylpiperidin-4-yl)-9H-purine-2,8-diamine,
N2-tert-butyl-N8-(3,4-dichlorophenyl)-9-(1-ethylpiperidin-4-yl)-9H-purine-2,8-diamine,
N2-tert-butyl-N8-(3,5-dichlorophenyl)-9-(pyrrolidin-3-yl)-9H-purine-2,8-diamine,
9-(1-(2-aminoethyl)piperidin-4-yl)-N2-tert-butyl-N8-(3-chloro-5-(trifluoromethyl)phenyl)-9H-purine-2,8-diamine,
N8-(3-chloro-5-(trifluoromethyl)phenyl)-N2-cyclopropyl-9-(piperidin-4-yl)-9H-purine-2,8-diamine,
N8-(3,5-dichlorophenyl)-N2-(1-methylcyclopropyl)-9-(piperidin-4-yl)-9H-purine-2,8-diamine,
N8-(3-chloro-5-(trifluoromethyl)phenyl)-N2-(1-methylcyclopropyl)-9-(piperidin-4-yl)-9H-purine-2,8-diamine,
N8-(3,5-dichlorophenyl)-N2-isopropyl-9-(piperidin-4-yl)-9H-purine-2,8-diamine,
N8-(3-chloro-5-(trifluoromethyl)phenyl)-N2-isopropyl-9-(piperidin-4-yl)-9H-purine-2,8-diamine,
N2-tert-butyl-N8-(3-chloro-5-(trifluoromethyl)phenyl)-9-(pyrrolidin-3-yl)-9H-purine-2,8-diamine,
9-(piperidin-4-yl)-N2-(tetrahydro-2H-pyran-4-yl)-N8-(3-(trifluoromethyl)phenyl)-9H-purine-2,8-diamine,
N2-tert-butyl-N8-(3-chloro-2-fluorophenyl)-9-(piperidin-4-yl)-9H-purine-2,8-diamine,
N2-tert-butyl-N8-(3-chloro-5-(trifluoromethoxy)phenyl)-9-(piperidin-4-yl)-9H-purine-2,8-diamine,
N8-(3,5-bis(trifluoromethyl)phenyl)-N2-tert-butyl-9-(piperidin-4-yl)-9H-purine-2,8-diamine,
3-(2-(tert-butylamino)-9-(piperidin-4-yl)-9H-purin-8-ylamino)benzonitrile,
N8-(3-chloro-5-(trifluoromethyl)phenyl)-9-(piperidin-4-yl)-N2-(tetrahydro-2H-pyran-4-yl)-9H-purine-2,8-diamine,
N8-(3-chloro-5-(trifluoromethyl)phenyl)-N2-cyclobutyl-9-(piperidin-4-yl)-9H-purine-2,8-diamine,
N8-(3-chloro-5-(trifluoromethyl)phenyl)-N2-cyclopentyl-9-(piperidin-4-yl)-9H-purine-2,8-diamine,
N8-(3-chloro-5-(trifluoromethyl)phenyl)-N2-(4-methyltetrahydro-2H-pyran-4-yl)-9-(piperidin-4-yl)-9H-purine-2,8-diamine,
N2-(4-methyltetrahydro-2H-pyran-4-yl)-9-(piperidin-4-yl)-N8-(3-(trifluoromethoxy)phenyl)-9H-purine-2,8-diamine,
N8-(3-chloro-5-fluorophenyl)-N2-(4-methyltetrahydro-2H-pyran-4-yl)-9-(piperidin-4-yl)-9H-purine-2,8-diamine,
N8-(3-(difluoromethyl)phenyl)-N2-(4-methyltetrahydro-2H-pyran-4-yl)-9-(piperidin-4-yl)-9H-purine-2,8-diamine,
N2-(4-methyltetrahydro-2H-pyran-4-yl)-9-(2-(pyrrolidin-3-yl)ethyl)-N8-(3-(trifluoromethyl)phenyl)-9H-purine-2,8-diamine,
N2-(1-methylcyclopentyl)-9-(piperidin-4-yl)-N8-(3-(trifluoromethyl)phenyl)-9H-purine-2,8-diamine,
9-(1-(2-aminoethyl)pyrrolidin-3-yl)-N2-tert-butyl-N8-(3-chloro-5-(trifluoromethyl)phenyl)-9H-purine-2,8-diamine,
N8-(3,5-dichlorophenyl)-N2-(4-methyltetrahydro-2H-pyran-4-yl)-9-(piperidin-4-yl)-9H-purine-2,8-diamine,
N8-(3-chloro-5-fluorophenyl)-N2-cyclopropyl-9-(piperidin-4-yl)-9H-purine-2,8-diamine,
N8-(3-chloro-5-fluorophenyl)-N2-isopropyl-9-(piperidin-4-yl)-9H-purine-2,8-diamine,
N8-(3-chloro-5-fluorophenyl)-N2-(1-methylcyclopropyl)-9-(piperidin-4-yl)-9H-purine-2,8-diamine,
N8-(3,4-dichlorophenyl)-N2-isopropyl-9-(piperidin-4-yl)-9H-purine-2,8-diamine,
N2-isopropyl-9-(piperidin-4-yl)-N8-(3-(trifluoromethyl)phenyl)-9H-purine-2,8-diamine,
N8-(3-chloro-5-(trifluoromethyl)phenyl)-N2-(1-methylcyclobutyl)-9-(piperidin-4-yl)-9H-purine-2,8-diamine,
(S)—N2-tert-butyl-N8-(3-chloro-5-(trifluoromethyl)phenyl)-9-(pyrrolidin-3-yl)-9H-purine-2,8-diamine,
N8-(3-chloro-5-(trifluoromethyl)phenyl)-N2-cyclobutyl-9-(pyrrolidin-3-yl)-9H-purine-2,8-diamine,
N8-(3-chloro-5-(trifluoromethyl)phenyl)-N2-cyclobutyl-9-(pyrrolidin-3-yl)-9H-purine-2,8-diamine,
N8-(3-chloro-5-(trifluoromethyl)phenyl)-N2-isopropyl-9-(pyrrolidin-3-yl)-9H-purine-2,8-diamine,
N8-(3-chloro-5-(trifluoromethyl)phenyl)-N2-(1-methylcyclopentyl)-9-(pyrrolidin-3-yl)-9H-purine-2,8-diamine,
N8-(3,5-dichlorophenyl)-N2-(1-methylcyclopentyl)-9-(pyrrolidin-3-yl)-9H-purine-2,8-diamine,
N8-(3-chloro-5-(trifluoromethyl)phenyl)-N2-(1-methylcyclopropyl)-9-(pyrrolidin-3-yl)-9H-purine-2,8-diamine,
N8-(3,5-dichlorophenyl)-N2-(1-methylcyclopropyl)-9-(pyrrolidin-3-yl)-9H-purine-2,8-diamine,
N2-tert-butyl-9-(octahydro-1H-isoindol-5-yl)-N8-(3-(trifluoromethyl)phenyl)-9H-purine-2,8-diamine,
N8-(4-chloro-3-(trifluoromethyl)phenyl)-N2-isopropyl-9-(piperidin-4-yl)-9H-purine-2,8-diamine,
N8-(4-chloro-3-(trifluoromethyl)phenyl)-N2-cyclopropyl-9-(piperidin-4-yl)-9H-purine-2,8-diamine,
N8-(3-chloro-4-(trifluoromethyl)phenyl)-N2-cyclopropyl-9-(piperidin-4-yl)-9H-purine-2,8-diamine,
N2-tert-butyl-N8-(3-chloro-4-(trifluoromethyl)phenyl)-9-(piperidin-4-yl)-9H-purine-2,8-diamine,
N8-(3-chloro-4-(trifluoromethyl)phenyl)-N2-cyclobutyl-9-(piperidin-4-yl)-9H-purine-2,8-diamine,
N8-(3,5-bis(trifluoromethyl)phenyl)-N2-isopropyl-9-(piperidin-4-yl)-9H-purine-2,8-diamine,
N8-(3,5-bis(trifluoromethyl)phenyl)-N2-cyclopentyl-9-(piperidin-4-yl)-9H-purine-2,8-diamine,
N8-(3,5-bis(trifluoromethyl)phenyl)-N2-cyclobutyl-9-(piperidin-4-yl)-9H-purine-2,8-diamine,
N8-(4-chloro-3-(trifluoromethyl)phenyl)-N2-cyclopentyl-9-(piperidin-4-yl)-9H-purine-2,8-diamine, N2-tert-butyl-N8-(4-chloro-3-(trifluoromethyl)phenyl)-9-(piperidin-4-yl)-9H-purine-2,8-diamine,
N8-(4-chloro-3-(trifluoromethyl)phenyl)-N2-(1-methylcyclopropyl)-9-(piperidin-4-yl)-9H-purine-2,8-diamine,
N8-(4-chloro-3-(trifluoromethyl)phenyl)-N2-(1-methylcyclopentyl)-9-(piperidin-4-yl)-9H-purine-2,8-diamine,
N8-(3-chloro-4-(trifluoromethyl)phenyl)-N2-isopropyl-9-(piperidin-4-yl)-9H-purine-2,8-diamine,
N8-(3-chloro-4-(trifluoromethyl)phenyl)-N2-cyclopentyl-9-(piperidin-4-yl)-9H-purine-2,8-diamine,
N8-(3-chloro-4-(trifluoromethyl)phenyl)-N2-(1-methylcyclopropyl)-9-(piperidin-4-yl)-9H-purine-2,8-diamine,
N8-(3-chloro-4-(trifluoromethyl)phenyl)-N2-(1-methylcyclopentyl)-9-(piperidin-4-yl)-9H-purine-2,8-diamine,
N2-tert-butyl-9-(octahydrocyclopenta[c]pyrrol-5-yl)-N8-(3-(trifluoromethyl)phenyl)-9H-purine-2,8-diamine,
N8-(3,5-bis(trifluoromethyl)phenyl)-N2-cyclopropyl-9-(piperidin-4-yl)-9H-purine-2,8-diamine,
9-(azetidin-3-yl)-N2-tert-butyl-N8-(3-chloro-5-(trifluoromethyl)phenyl)-9H-purine-2,8-diamine,
N2-tert-butyl-N8-(3-chloro-5-(trifluoromethyl)phenyl)-9-(pyrrolidin-3-ylmethyl)-9H-purine-2,8-diamine,
3-(2-(tert-butylamino)-9-(pyrrolidin-3-yl)-9H-purin-8-ylamino)-5-chlorobenzonitrile,
9-(2-aminoethyl)-N2-tert-butyl-N8-(3-chloro-5-(trifluoromethyl)phenyl)-9H-purine-2,8-diamine,
9-(2-amino-2-methylpropyl)-N8-(3-chloro-5-(trifluoromethyl)phenyl)-N2-cyclopentyl-9H-purine-2,8-diamine,
9-(2-amino-2-methylpropyl)-N2-tert-butyl-N8-(3-chloro-5-(trifluoromethyl)phenyl)-9H-purine-2,8-diamine,
3-chloro-5-(2-(isopropylamino)-9-(pyrrolidin-3-yl)-9H-purin-8-ylamino)benzonitrile,
N8-(3-chloro-5-fluorophenyl)-N2-isopropyl-9-(pyrrolidin-3-yl)-9H-purine-2,8-diamine,
9-(2-aminoethyl)-N8-(3-chloro-5-(trifluoromethyl)phenyl)-N2-cyclopentyl-9H-purine-2,8-diamine,
N8-(3-chloro-5-(trifluoromethyl)phenyl)-N2-cyclopentyl-9-(2-(methylamino)ethyl)-9H-purine-2,8-diamine,
N2-tert-butyl-N8-(3-chloro-5-(trifluoromethyl)phenyl)-9-(2-(methylamino)ethyl)-9H-purine-2,8-diamine,
9-(2-aminopropyl)-N8-(3-chloro-5-(trifluoromethyl)phenyl)-N2-cyclopentyl-9H-purine-2,8-diamine,
9-(2-aminopropyl)-N2-tert-butyl-N8-(3-chloro-5-(trifluoromethyl)phenyl)-9H-purine-2,8-diamine,
3-chloro-5-(2-(cyclopentylamino)-9-(pyrrolidin-3-yl)-9H-purin-8-ylamino)benzonitrile,
9-(3-aminobutyl)-N8-(3-chloro-5-(trifluoromethyl)phenyl)-N2-cyclopentyl-9H-purine-2,8-diamine,
9-(3-aminobutyl)-N2-tert-butyl-N8-(3-chloro-5-(trifluoromethyl)phenyl)-9H-purine-2,8-diamine,
(S)—N8-(3-chloro-5-(trifluoromethyl)phenyl)-N2-cyclobutyl-9-(pyrrolidin-3-yl)-9H-purine-2,8-diamine, or
(R)—N8-(3-chloro-5-(trifluoromethyl)phenyl)-N2-cyclobutyl-9-(pyrrolidin-3-yl)-9H-purine-2,8-diamine,
or a pharmaceutically acceptable salt, tautomer, isotopologue, or stereoisomer thereof.

21. The method of claim 1, wherein the malaria is caused by *Plasmodium falciparum, Plasmodium vivax, Plasmodium ovale, Plasmodium knowlesi* or *Plasmodium malariae*.

22. The method of claim 21, further comprising administering an effective amount of chloroquine, quinine, quinidine, mefloquine, atovaquone, proguanil, doxycycline, artesunate, artemether, artemisinin, lumefantrine, amodiaquine, hydroxychloroquine, halofantrine, pyrimethamine, sulfadoxine, or primaquine.

* * * * *